(12) United States Patent
Richter et al.

(10) Patent No.: US 7,141,312 B2
(45) Date of Patent: Nov. 28, 2006

(54) ORGANIC ELECTROLUMINESCENT DEVICE BASED ON 2,5-DIAMINOTEREPHTHALIC ACID DERIVATIVES

(75) Inventors: Andreas Richter, Plöessnitz (DE); Jens Schöenewerk, Grimma (DE); Gerhard Diener, Köethen (DE)

(73) Assignee: Sensient Imaging Technologies GmbH, Wolfen (DE)

( * ) Notice: Subject to any disclaimer, the term of this patent is extended or adjusted under 35 U.S.C. 154(b) by 0 days.

(21) Appl. No.: 10/784,149

(22) Filed: Feb. 20, 2004

(65) Prior Publication Data

US 2005/0025992 A1 Feb. 3, 2005

Related U.S. Application Data

(63) Continuation of application No. PCT/DE02/03110, filed on Aug. 21, 2002.

(30) Foreign Application Priority Data

Aug. 21, 2001 (DE) ................ 101 41 266

(51) Int. Cl.
*H01L 51/54* (2006.01)
*H05B 33/14* (2006.01)
*C09K 11/06* (2006.01)

(52) U.S. Cl. ............... 428/690; 428/917; 313/504
(58) Field of Classification Search ............... 428/690, 428/917; 313/504, 506; 546/184, 186, 190, 546/191, 230, 233; 548/518, 523, 524, 560, 548/565, 566, 567, 571, 572, 577
See application file for complete search history.

(56) References Cited

U.S. PATENT DOCUMENTS

| | | | |
|---|---|---|---|
| 3,153,667 A | 10/1964 | Smith | |
| 3,671,451 A * | 6/1972 | Butterfield | 252/301.35 |
| 4,124,768 A | 11/1978 | Kirsch et al. | 560/19 |
| 4,208,328 A | 6/1980 | Lavallee et al. | 548/180 |
| 5,281,489 A * | 1/1994 | Mori et al. | 428/690 |
| 5,409,783 A | 4/1995 | Tang et al. | 428/690 |
| 5,616,779 A | 4/1997 | Arndt | 560/48 |
| 6,288,232 B1 | 9/2001 | Shershukov et al. | 546/52 |
| 6,329,086 B1 | 12/2001 | Shi et al. | 428/690 |
| 6,458,476 B1 | 10/2002 | Suzuki et al. | 428/690 |
| 6,534,201 B1 | 3/2003 | Kim et al. | 428/690 |
| 6,579,633 B1 | 6/2003 | Kim et al. | 428/690 |
| 6,613,458 B1 | 9/2003 | Lee et al. | 428/690 |
| 2001/0012905 A1 | 8/2001 | Shershukov et al | 562/446 |
| 2002/0028351 A1 | 3/2002 | Wang et al. | 428/690 |
| 2002/0043656 A1 | 4/2002 | Shershukov et al. | 252/586 |
| 2002/0045065 A1 | 4/2002 | Kim et al. | 428/690 |
| 2002/0114973 A1 | 8/2002 | Hotta et al. | 428/690 |
| 2003/0082403 A1 | 5/2003 | Lee et al. | 428/690 |
| 2003/0096137 A1 | 5/2003 | Son et al. | 428/690 |
| 2003/0099861 A1 | 5/2003 | Lee et al. | 428/690 |
| 2003/0165711 A1 | 9/2003 | Kim et al. | 428/690 |

FOREIGN PATENT DOCUMENTS

| | | |
|---|---|---|
| GB | 868361 | 5/1961 |
| GB | 918511 | 2/1963 |
| WO | WO 03/076390 A1 * | 9/2003 |
| WO | WO 2004/026809 A1 * | 4/2004 |

OTHER PUBLICATIONS

Machine-assisted translation of JP 10-284250 (Oct. 1998).*
Japanese Patent Abstract of 10-294178, Nov. 4, 1998.
Japanese Patent Abstract of 10-284250, Oct. 23, 1998.
Moore et al., "Poly(amine esters) Derived from Diethyl 1,4-Cyclohexanedione-2,5-dicarboxylate", *Macromolecules*, vol. 8, 1975, (pp. 121-127).
Ulbricht et al., "Synthese und π-Elektronenstruktur von 2,5-Bis-alkylamino-terephthalsäurediethylestern", Journal f. prakt. Chemie. Band 321, Heft 6, 1979, (S. 905-912).

* cited by examiner

*Primary Examiner*—Marie Yamnitzky
(74) *Attorney, Agent, or Firm*—Michael Best & Friedrich LLP

(57) ABSTRACT

The application relates to an organic electroluminescent device which contains 2,5 diaminoterephthalic acid derivatives of formula 1a as emitter substances in one or several emitter layers in a pure or doped manner. The ring A is a triple unsaturated benzene ring wherein $R^{4'}$ and $R^{8'}$ are equal to zero or ring A is a double unsaturated ring respectively provided with a double bond in the 1,2 position and 4,5-position, and wherein $R^{10}$ is a nitrile radical —CN or a radical $C(=X^1)$—$X^2R^1$; $R^{11}$ is a nitrile radical —CN or a radical —$C(=X^3)$—$X^4R^5$, $X^1$ and $X^3$ are oxygen, sulphur or imino, $X^2$ and $X^4$ are oxygen, sulphur or optionally substituted amino, $R^1$ to $R^8$, $R^{4'}$ and $R^{8'}$ are H, C1–C20-alkyl, aryl, heteroaryl, $R^4$ and $R^8$ can also be halogen, nitro, cyanogen or amino, $R^2$ to $R^4$, $R^6$–$R^8$, $R^{4'}$ and $R^{8'}$ can also be trifluoromethyl or pentafluorophenyl, wherein certain radicals can form a saturated or unsaturated ring. The novel devices are characterized by narrow emission bands, low driver voltages, high photometric efficiency and high thermal stability within a broad spectral range.

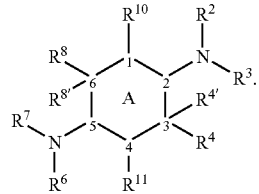

1a

18 Claims, 1 Drawing Sheet

Figure 1:
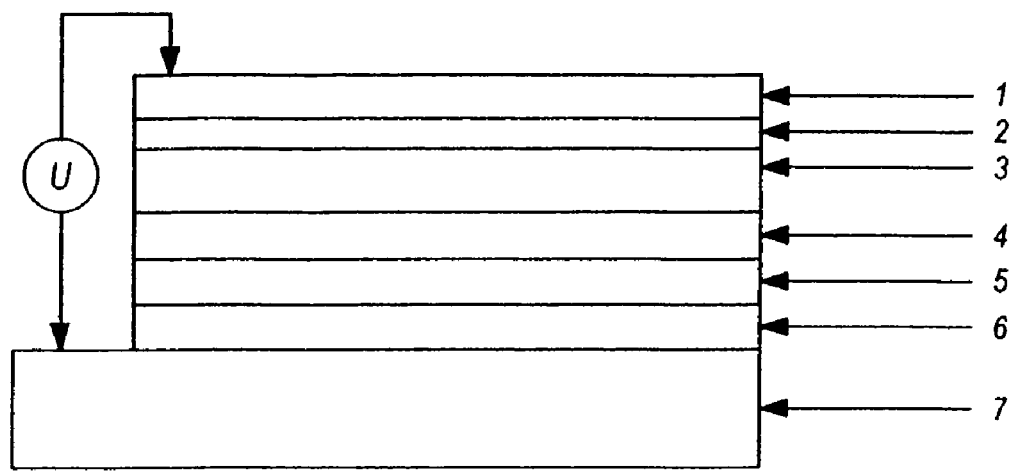

ORGANIC ELECTROLUMINESCENT DEVICE BASED ON 2,5-DIAMINOTEREPHTHALIC ACID DERIVATIVES

CROSS-REFERENCE TO RELATED APPLICATIONS

This application is a continuation of and claims priority to International Application No. PCT/DE02/03110 filed on Aug. 21, 2002, which claims priority to German Application No. 10141266.5 filed on Aug. 21, 2001. This application claims the priority of each of these applications and patents and fully incorporates the subject matter thereof.

The present application relates to a new organic electroluminescent device based on 2,5-diaminoterephthalic acid derivatives. Said derivatives are emitter substances for organic light-emitting diodes (OLED). Organic light-emitting diodes, which have long been known, use the electroluminescence of certain organic compounds. An OLED's structure and the tasks of its individual layers are exemplified in FIG. 1. A layer sequence of organic substances is arranged between two electrodes, of which at least one must be translucent, each organic substance having a specific function within the device.

The cathode consists of a base metal or an alloy (e.g. aluminium or calcium) and has the function of injecting electrons;

The buffer layer consists of certain metal salts or the oxides thereof, e.g. LiF, and has the function of improving the electron injection into the layer 3;

The electron conductor can e.g. consist of Alq3 (tris-(8-hydroxychinolinato)-aluminium) and conducts the electrons from the cathode to the emitting layer or the hole conductor inside the device;

The hole conductor mainly consists of triphenylamine derivatives; several hole conductor layers can be provided whose characteristics are adapted to the device and whose function is to transport the holes to the emitting layer;

The anode consists of ITO which injects the holes into the hole transport layer;

The substrate consists of a transparent material, e.g. glass.

An arrangement of the type described above emits green light generated due to the excitation of Alq3 by the excitons formed from the holes and electrons.

However, such a simple arrangement has several drawbacks:
1. Alq3 only emits light in the green spectral range;
2. The emission band of Alq3 is too broad.

Said drawbacks can in part be eliminated by doping. This means that one or more substances are co-evaporated during the diode's production process. In general, these substances are contained in the Alq3 layer in an amount ranging up to a few percent. Said co-evaporation process is difficult to control.

This application relates to new emitter substances which eliminate the known drawbacks of Alq3 both as an emitter substance and a host material for dopants. As a consequence, Alq3 is generally required as an electron conductor only. The new emitter substances are characterized by:

1. narrower emission bands;
2. the devices cover a broad spectral range due to the fact that different substances are used, either in layers separated from one another or in mixed layers;
3. low driver voltages;
4. high photometric efficiency (low power consumption);
5. high luminance (emission intensity);
6. high thermal stability.

Figure 2:
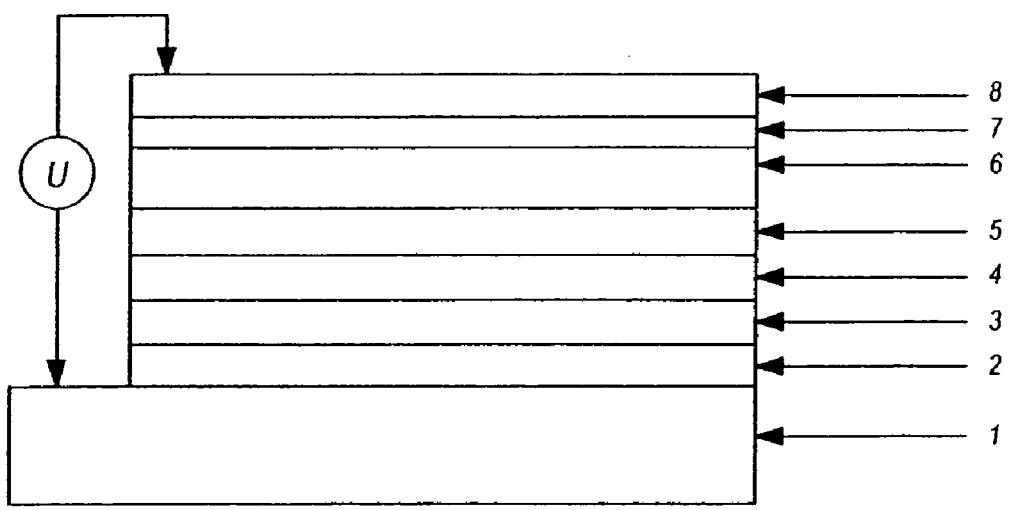

For the purposes of this application, the term "device" relates to an arrangement in which the substrate and layers are arranged on top of one another according to FIG. 1 or 2, but which has not yet been incorporated into a light-emitting diode. Such a device can in principle have the structure shown in FIG. 1 or 2. In said devices, the 2,5-diaminoterephthalic acid derivatives can be co-evaporated either alone or conjointly with other compounds, optionally even with known compounds, to obtain emitters. These emitters are used in combination with known hole conductors.

The present application provides new organic electroluminescent devices using improved emitter substances. According to one embodiment, the organic electroluminescent device contains 2,5-diaminoterephthalic acid derivatives of the following formula 1a in one or several emitter layers in a pure or doped form in a device

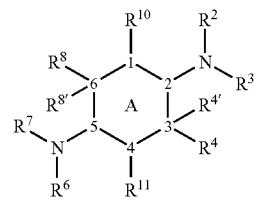

1a wherein the ring A is a triply unsaturated benzene ring wherein $R^{4'}$ and $R^{8'}$ are omitted, or the ring A is a doubly unsaturated ring having a double bond in the 1,2-position and in the 4,5-position, and wherein $R^{10}$ represents a nitrile radical —CN or a radical —C(=X$^1$)—X$^2$R$^1$, $R^{11}$ is a nitrile radical —CN or a radical —C(=X$^3$)—X$^4$R$^5$, wherein $X^1$ and $X^3$ can be the same or different atoms or groups, such as oxygen, sulphur, imino, preferably oxygen;

$X^2$ and $X^4$ can be the same or different atoms or groups, such as oxygen, sulphur, amino, wherein the amino nitrogen can be substituted with alkyl having 1 to 20 C-atoms, preferably C1 to C8, or with aryl, e.g. phenyl, naphthyl, or with heteroaryl, e.g. cumaryl, pyridyl, chinolyl, indolyl, carbazolyl, imidazolyl, thienyl, thiazolyl, furyl, oxazolyl;

$R^1$ to $R^8$, $R^{4'}$ and $R^{8'}$ can be the same or different substituents, such as hydrogen, alkyl having 1 to 20 atoms, preferably C1 to C8; aryl, e.g. phenyl, naphthyl, as well as heteroaryl, e.g. cumaryl, pyridyl, chinolyl, indolyl, carbazolyl, imidazolyl, thienyl, thiazolyl, furyl, oxazolyl, and the aforesaid radicals can be substituted singly or doubly with atoms or groups, e.g. di-C1–C3-amino or alkoxy with alkyl radicals C1 to C10, preferably C1–C4;
C1–C4 alkyl, cyano, fluorine, chlorine, bromine or iodine
as well as phenyl;

$R^4$ and $R^8$ can also be the same or different substituents, such
as halogen, nitro, cyano or amino;

$R^2$ to $R^4$, $R^6$ to $R^8$, $R^{4'}$ and $R^{8'}$ can also be trifluoromethyl or
pentafluorophenyl, and wherein the following radicals can
form a saturated or unsaturated ring $X^1$ and $X^2$, $R^1$ and $R^2$, $R^2$ and $X^2$, $R^2$ and $R^3$, $R^3$ and $R^4$, $R^4$
and $X^3$, $X^3$ and $X^4$, $R^5$ and $X^4$, $R^6$ and $X^4$, $R^6$ and $R^7$, $R^7$ and $R^8$, $R^8$ and $X^1$, $R^3$ and $R^{4'}$, $R^7$ and $R^{8'}$,
$R^4$ and $R^{4'}$, and $R^8$ and $R^{8'}$, to which rings further rings
can be fused.

It is preferred that $R^2$, $R^3$, $R^6$ and $R^7$ be trifluoromethyl or
pentafluorophenyl, $R^4$ and $R^8$ be halogen, nitro, cyano or
amino, and the other substituents have the meaning indicated above. It is particularly preferred that $R^4$ and $R^8$ be
trifluoromethyl or pentafluorophenyl, and the other substituents have the meaning indicated above.

As regards spelling in the following text, $R^{1-8}$ means $R^1$
to $R^8$; $X^{2,4}$ means $X^2$ and $X^4$; $R^{4',8'}$ means $R^{4'}$ and $R^{8'}$.

The application also relates to new 2,5-diaminoterephthalic acid derivatives of the formula 19

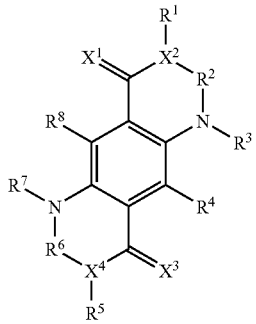

19 wherein $X^1$ is O and $X^2$ is O or N; $R^2$ and $R^6$ are methylene
(—$CH_2$—) which can be substituted with trifluoromethyl,
$R^3$ and $R^7$ are the same or different, H, C1–C8 alkyl, aryl or
heteroaryl, and $R^4$ and $R^8$ are the same or different, H, alkyl,
aryl or trifluoromethyl.

It is particularly preferred that alkyl be C1–C4 alkyl, aryl
be phenyl or naphthyl, and heteroaryl be pyridyl, thienyl or
furyl.

In general, it is preferred that substituents arranged opposite one another, such as $X^1$ and $X^3$, $X^2$ and $X^4$, $R^1$ and $R^5$,
$R^2$ and $R^6$, $R^3$ and $R^7$, $R^4$ and $R^8$, $R^{4'}$ and $R^{8'}$, $R^{10}$ and $R^{11}$,
are the same, i.e. not different, in the structures described
herein. The electroluminescent devices according to one
embodiment preferably contain 2 to 3 different substances
which are mixed with one another in one device.

Now, preferred structures will be listed, wherein in the
structures 1

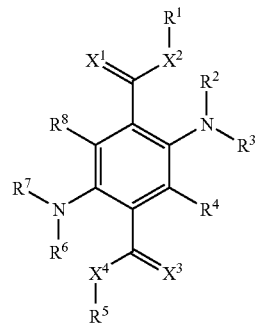

1

$X^1$ and $X^2$ can be members of a ring
provided $X^1 = N$ and there is no substituent
$R^1$ in case $X^2 \neq N$;

$X^1$ and $R^2$ can be members of a ring
provided $X^2 = N$;

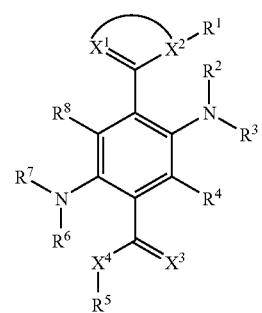

5

$X^1$ and $R^2$ can be members of a ring
provided $X^2 = N$;

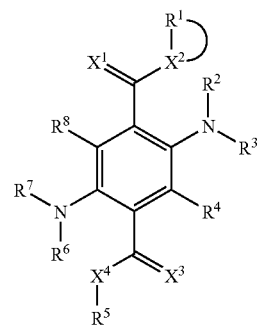

6

$R^2$ and $R^3$ can be members of a ring;

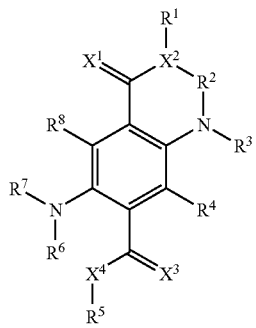

7

$R^3$ and $R^4$ can be members of a ring;

-continued

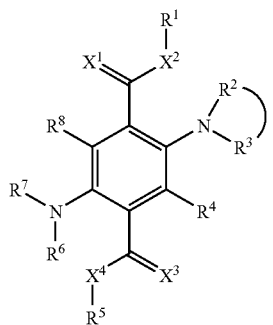

8

R⁴ and R³ can be members of a ring
provided X³ = N;

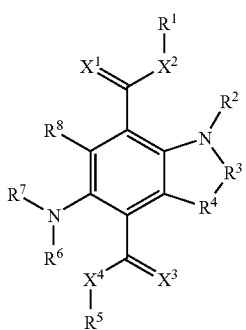

9

X³ and X⁴ can be members of a ring
provided X³ = N and there is no substituent
R¹ in case X⁴ ≠ N;

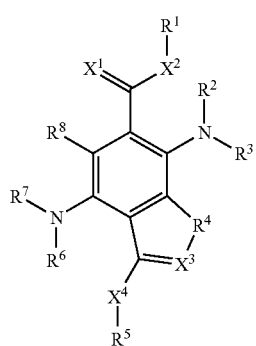

10

X⁴ and R⁵ can be members of a ring
provided X⁴ = N;

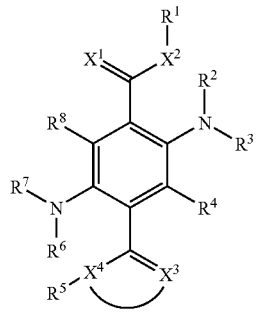

11

X⁴ and R⁶ can be members of a ring
provided X⁴ = N;

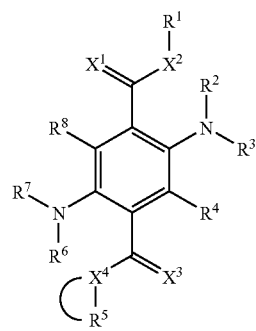

12

R⁶ and R⁷ can be members of a ring;

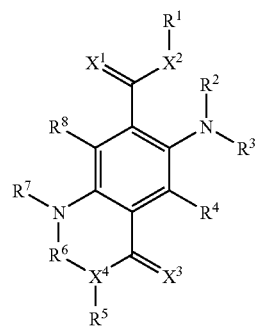

13

R⁷ and R⁸ can be members of a ring;

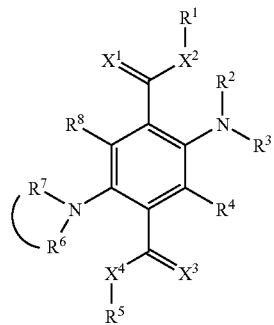

14

R⁸ and X¹ can be members of a ring
provided X¹ = N;
wherein symmetric combinations of the aforesaid structural types are preferred

15

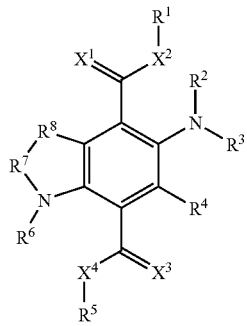

$X^1$ and $X^2$ as well as $X^3$ and $X^4$ can be members of a ring provided $X^{1,3} = N$ and there is no substituent $R^{1,5}$ in case $X^{2,4} \neq N$;

16

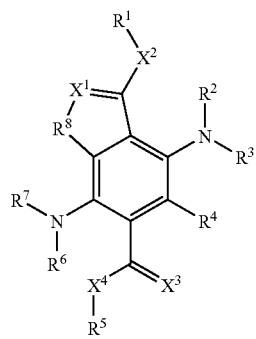

$X^2$ and $R^1$ can be members of a ring provided $X^{2,4} = N$;

17

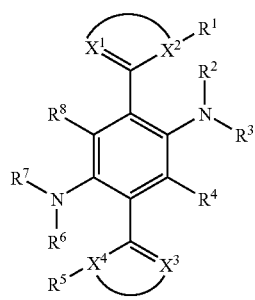

$X^2$ and $R^2$ as well as $X^4$ and $R^6$ can be members of a ring provided $X^{2,4} = N$;

18

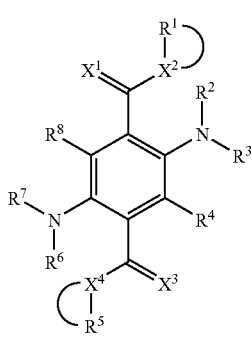

$R^2$ and $R^3$ as well as $R^6$ and $R^7$ can be members of a ring;

19

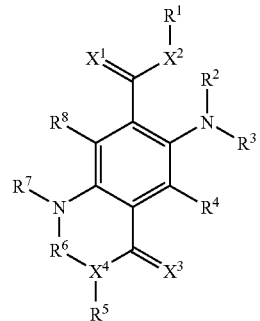

$R^3$ and $R^4$ as well as $R^7$ and $R^8$ can be members of a ring;

20

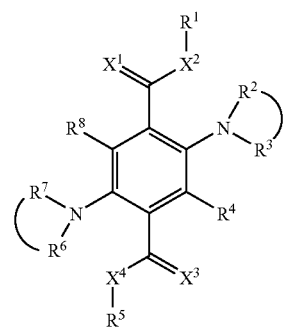

$R^4$ and $X^3$ as well as $R^8$ and $X^1$ can be members of a ring provided $X^{1,3} = N$;

21

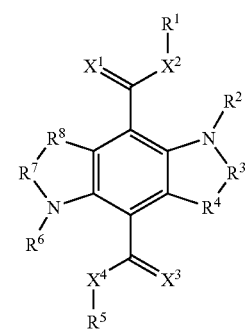

and wherein in the structures 2

22

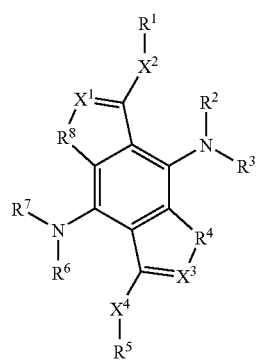

-continued

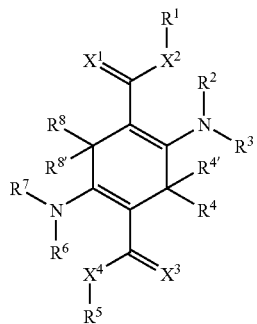
2

$X^1$ and $X^2$ can be members of a ring provided $X^1 = N$ and there is no substituent $R^1$ in case $X^2 \neq N$;

$X^2$ and $R^1$ can be members of a ring provided $X^2 = N$;

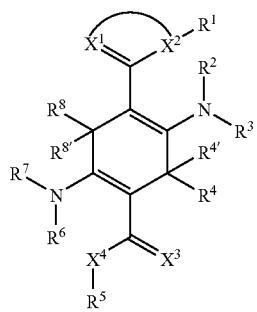
23

$X^2$ and $R^2$ can be members of a ring provided $X^2 = N$;

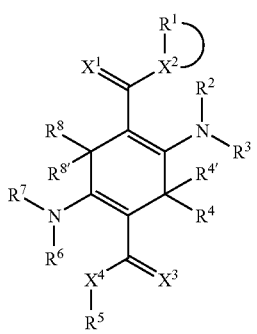
24

$R^2$ and $R^3$ can be members of a ring;

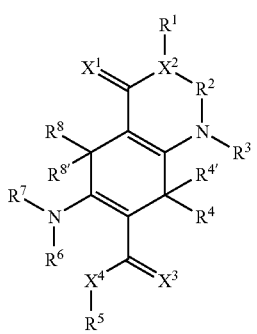
25

$R^3$ and $R^4$ can be members of a ring;

-continued

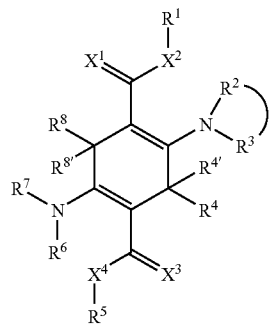
26

$R^4$ and $R^{4'}$ can be members of a ring;

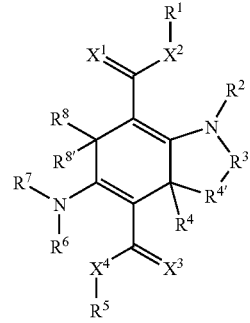
27

$R^4$ and $X^3$ can be members of a ring provided $X^3 = N$;

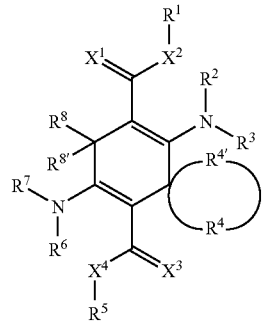
28

$X^3$ and $X^4$ can be members of a ring provided $X^3 = N$ and there is no substituent $R^5$ in case $X^4 \neq N$;

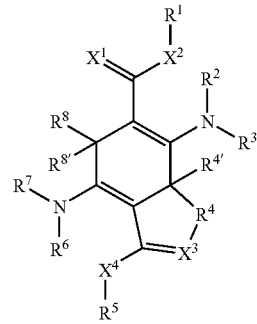
29

$X^4$ and $R^5$ can be members of a ring provided $X^4 = N$;

30

X⁴ and R⁶ can be members of a ring provided X⁴ = N;

31

R⁶ and R⁷ can be members of a ring;

32

R⁷ and R⁸ can be members of a ring;

33

R⁸ and R⁸' can be members of a ring;

34

R⁸ and X¹ can be members of a ring provided X¹ = N;

wherein symmetric combinations of the aforesaid structural types are preferred

35

X¹ and X² as well as X³ and X⁴ can be members of a ring provided X¹,³ = N and there is no substituent R¹,⁵ in case X²,⁴ ≠ N;

36

X² and R¹ can be members of a ring provided X²,⁴ = N;

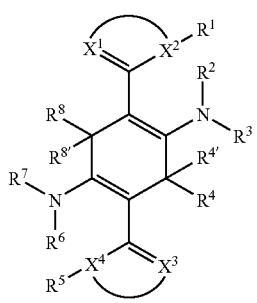

37

$X^2$ and $R^2$ as well as $X^4$ and $R^6$ can be members of a ring provided there is no substituent $R^{1,5}$ in case $X^{2,4} \neq N$;

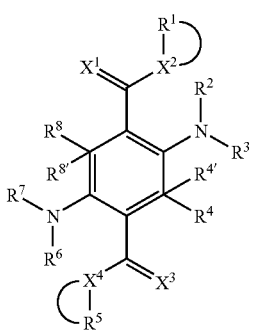

38

$R^2$ and $R^3$ as well as $R^6$ and $R^7$ can be members of a ring;

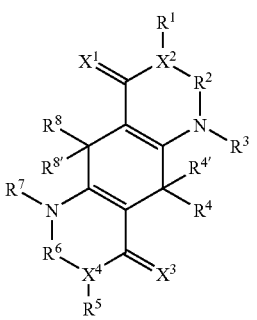

39

$R^3$ and $R^4$ as well as $R^7$ and $R^8$ can be members of a ring;

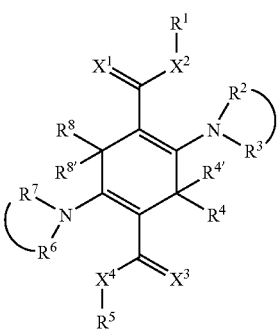

40

$R^4$ and $R^{4'}$ as well as $R^8$ and $R^{8'}$ can be members of a ring;

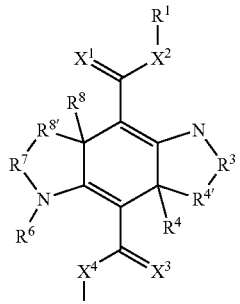

41

$R^4$ and $X^3$ as well as $R^8$ and $X^1$ can be members of a ring provided $X^{1,3} = N$;

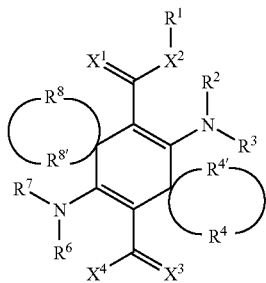

42

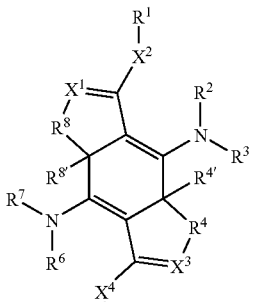

43 and wherein in the structures 3

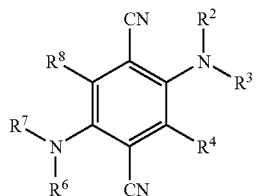

3

$R^2$ and $R^3$ can be members of a ring;
$R^3$ and $R^4$ can be members of a ring;

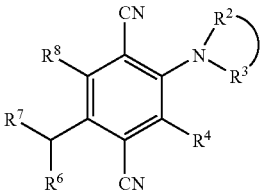

44

$R^6$ and $R^7$ can be members of a ring;

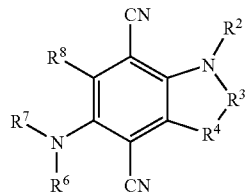

$R^7$ and $R^8$ can be members of a ring;

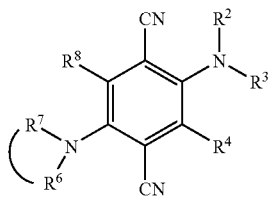

$R^2$ and $R^3$ as well as $R^6$ and $R^7$ can be members of a ring;

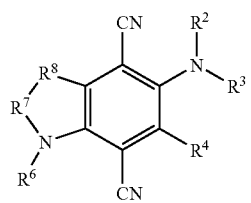

$R^3$ and $R^4$ as well as $R^7$ and $R^8$ can be members of a ring;

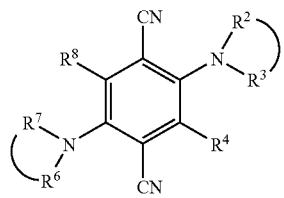

and wherein in the structures 4

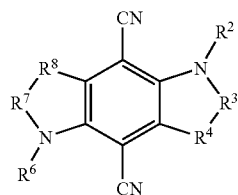

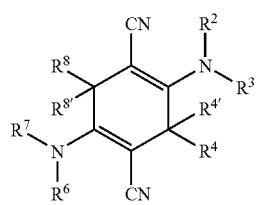

$R^2$ and $R^3$ can be members of a ring;

$R^3$ and $R^4$ can be members of a ring;

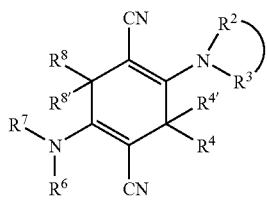

$R^4$ and $R^{4'}$ can be members of a ring;

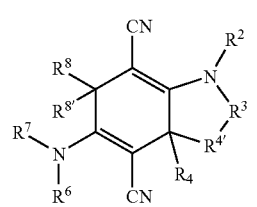

$R^6$ and $R^7$ can be members of a ring;

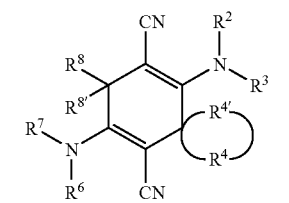

$R^7$ and $R^8$ can be members of a ring;

$R^8$ and $R^{8'}$ can be members of a ring;

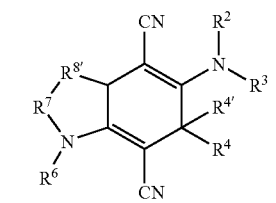

$R^2$ and $R^3$ as well as $R^6$ and $R^7$ can be members of a ring;

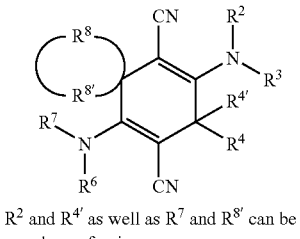

$R^2$ and $R^{4'}$ as well as $R^7$ and $R^{8'}$ can be members of a ring;

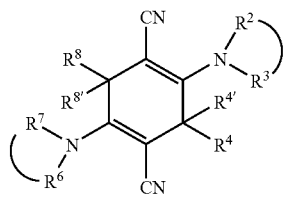

R⁴ and R⁴' as well as R⁸ and R⁸' can be members of a ring;

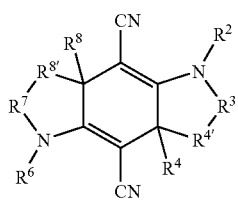

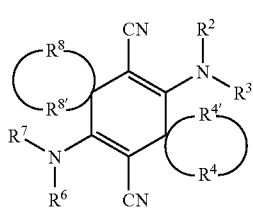

The emitter substances of formula 1, i.e. derivatives of 2,5-diaminoterephthalic acid, can be obtained by reacting esters of cyclohexane-2,5-dione-1,4-dicarboxylic acid with primary anilines or amines, subsequent oxidation and, optionally, further modification. Said derivatives can be processed into cyclized derivatives in a manner known per se, as shown e.g. in Formula Diagrams I and II.

Formula Diagram I: Synthesis of the open compounds

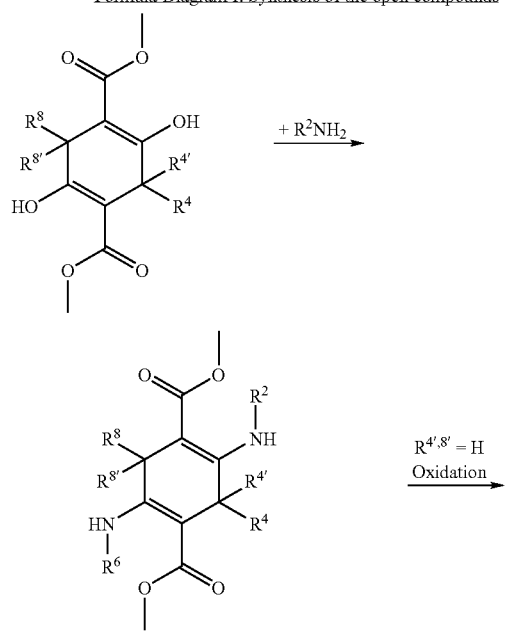

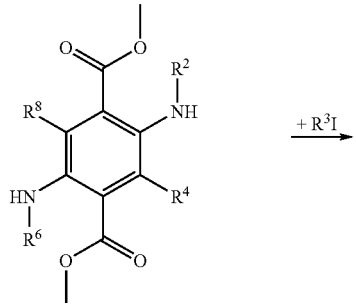

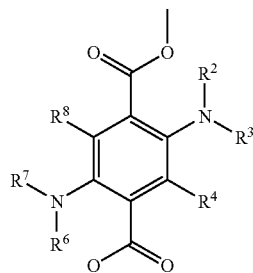

Formula Diagram II: Synthesis of the cyclized compounds

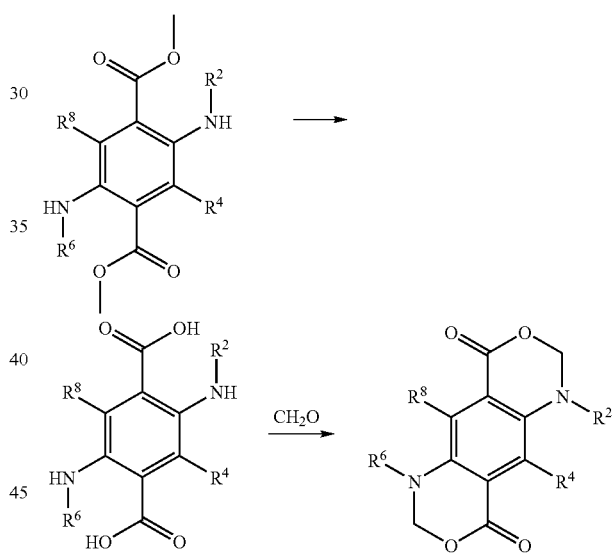

The compounds of formula 3 can be produced by reacting the respective 2,5-diaminoterephthalic acid amides with dehydrating agents.

In order to produce the compounds of formula 4, wherein R⁴ and R⁸ as well as R⁴' and R⁸' are not H, the esters of 2,5-diaminocyclohexane-1,4-dicarboxylic acid are converted into hydrazides and reacted with potassium hexacyanoferrate(III) in order to obtain aldehydes. These 2,5-diaminocyclohexane-1,4-dicarbaldehydes can be converted into oximes which are reacted with formic acid in order to obtain the compounds of formula 4.

Examples of the new emitters according to formula 1 are listed in Table 1 below.

The new emitters are used in a device comprising or not comprising an electron transport layer, wherein the layers in a device can be arranged as shown in FIG. 2:

1. The substrate consists of a transparent material, e.g. glass;

2. The anode consists of ITO which injects the holes into the hole transport layer;

3./4. The hole conductor mainly consists of triphenylamine derivatives; several hole conductor layers can be provided whose characteristics are adapted to the device;

5. Between the hole conductor and the electron conductor, one or more emitter layers are arranged;

6. The electron conductor can e.g. consist of Alq3 and conducts the electrons from the cathode to the emitting layer or the hole conductor inside the device;

7. The buffer layer consists of certain metal salts or the oxides thereof, e.g. LiF, and improves the electron injection into the layer 6;

8. The cathode consists of a base metal or an alloy (e.g. aluminium or calcium).

Typically, the emitter layers are 3–10 nm thick, preferably 4–6 nm. The emission wavelengths depend on the chemical structure in a characteristic manner, i.e. electronic and steric factors of the molecules obviously influence the wavelength of the emitted light and the performance achieved. The wavelengths of the examples listed in Table 2 range between 538 nm and 618 nm.

In order to achieve mixed colours, the new emitters of formulas 1.0–58.0 can be arranged on top of one another, either in the form of several layers each of which consists of an emitter material in its pure form (FIG. 2) or in the form of one or several layer(s) in which the emitter materials are provided in a mixed form.

The layers comprising the new emitters of formulas 1.0–58.0 can be doped with known emitter materials, as shown in FIG. 1.

The new emitters of formulas 1.0–58.0 can be used in devices comprising hole conductors known per se (59 and 60) and other components. Typical examples are shown in FIGS. 1 and 2.

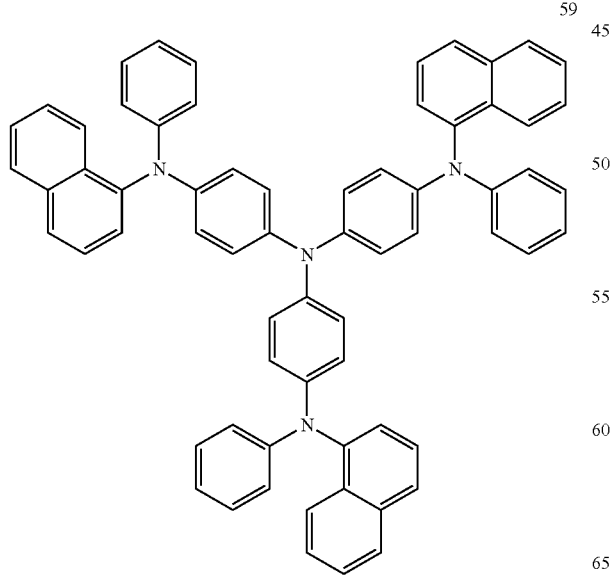

4,4',4''-tris(N-(α-naphthyl)-N-phenylamino)-triphenylamine (1-NAPHDATA)

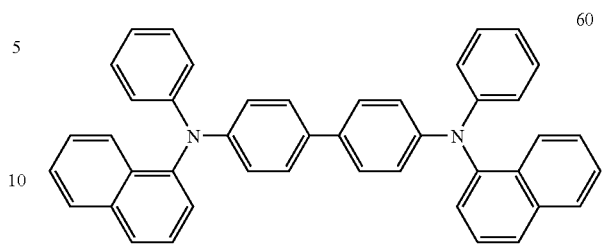

N,N'-di(α-naphthyl)-N,N'-diphenylbenzidine (α-NPD)

The devices based on the new emitters can be produced in a manner known per se, i.e. by vacuum deposition at between 1 and $10^{-9}$ torrs.

Alternatively, the devices can be produced by solution coating, e.g. web coating or spin coating. Here, the new emitters of formulas 1.0–58.0 can be applied either as the pure substance or as a dopant contained in a suitable polymer.

Surprisingly, it has been found that particularly efficient devices can be produced using substances of the formula 1.0 which have been substituted with fluorine. A remarkably high photometric efficiency is observed in these cases. Using the substance 1.2, a device emitting a spectrally nearly pure green is obtained. Experimental part The following examples are intended to illustrate the present invention in more detail, but do by no means limit the same.

EXAMPLE 1

(Substances 2.1, 2.3–2.5)

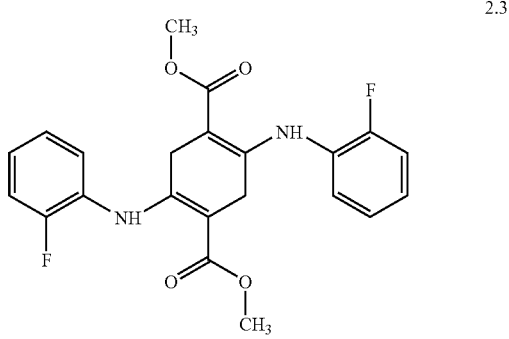

0.06 mol cyclohexane-2,5-dione-1,4-dicarboxylic acid diester is suspended in a mixture of 200 ml glacial acetic acid and 200 ml alcohol (corresponding to the ester component). In a nitrogen atmosphere, 0.135 mol of a primary amine or aniline is speedily added. The reaction mixture is refluxed for 5–8 hours while stirring thoroughly. Anilines which have been substituted with an acceptor require longer reaction times.

In the case of anilines, the crude product can be isolated by sucking off the cooled-down reaction mixture, thoroughly washing it with methanol and drying. Aliphatic amines form highly soluble products, i.e. the solvent must be separated almost completely using a rotary evaporator. The crude product is added into methanol, thoroughly cooled, sucked off and dried.

EXAMPLE 2

(Substances 1.1, 1.3–1.5)

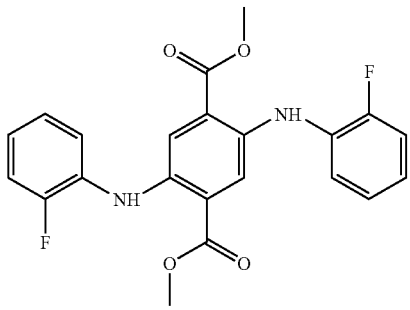

1.3

The esters of dihydroterephthalic acid obtained in Example 1 are oxidized. Yields of up to 95% are achieved during isolation. In order to purify the separated crude product, it can be recrystallized from DMF, toluene, chloroform or methanol. The substances obtained are sublimable.

EXAMPLE 3

(Substances 19.1–19.4)

The esters obtained according to Example 2 are saponified in mixtures of n-propanol and water. 0.01 mol terephthalic acid diester is suspended in approx. 50 ml n-propanol, and 50 ml water containing 0.03 mol potassium hydroxide is added. The suspension is refluxed until a clear solution is obtained. Once another 2 hours have passed, the liquid is sucked off. In order to neutralize the solution, approx. 5 ml glacial acetic acid is added dropwise. The acid obtained is washed with methanol and dried.

In order to produce the substances 19.1–19.4, 0.01 mol of the terephthalic acid obtained is refluxed for 2 hours in 100 ml glacial acetic acid to which 15 ml formaldehyde solution (37%) has been added. The reaction products are separated and washed with methanol. They are recrystallized from acetonitrile or chloroform. The substances obtained can be purified by sublimation.

EXAMPLE 4

(Substance 1.2)

In order to obtain compounds of this type, the respective terephthalic acid ester (Example 2) can be alkylated. 0.05 mol terephthalic acid ester is suspended in 350 ml anhydrous DMSO, and 18.63 g (0.131 mol) methyl iodide is added. 6.1 g (0.152 mol) 60% sodium hydride in paraffin is added in portions at a temperature ranging between 20 and 23° C. and while stirring thoroughly. Once a reaction time of approx. 5 hours has passed, the colour of the solid constituents has changed from orange to pure yellow. Now, approx. 200 ml methanol is added to the mixture, thereby considerably improving filterability.

The separated yellow reaction product is thoroughly washed with methanol and dried. A pure product is obtained by recrystallization from toluene.

EXAMPLE 5

(Device: Substance 19.4)

A 55 nm thick layer of 4,4', 4"-tris(N-(α-naphthyl)-N-phenylamino)-triphenylamine and another 5 nm thick layer of N,N'-di(α-naphthyl)-N,N'-diphenylbenzidine were deposited onto a structured ITO glass substrate measuring 50×50 mm$^2$. Onto these hole transport layers, 5 nm 1,6-bis (2,4-dimethoxyphenyl)-benzo[1,2-d; 4,5-d']-1,2,6,7-tetrahydro-bis[1,3]oxazine-4,9-dione (19.4) is deposited.

In addition, a 30 nm thick layer of tris-(8-hydroxychinolinato)-aluminium is now applied onto this emitter layer, followed by a very thin buffer layer (0.5 nm) of lithium fluoride and finally aluminium. The arrangement was tested applying an adjustable voltage between 0 and 15 V. The device emits a wavelength of 578 nm (yellow). A luminance (emission intensity) of 100 cd/m$^2$ was achieved at 5.0 V. The maximum luminance (emission intensity) achieved was 11,400 cd/m$^2$.

EXAMPLE 6

(Device: Substance 1.21)

A device was produced according to Example 5, into which a 5 nm thick layer of 2,5-bis-(N-(2,4-dimethoxyphenyl)amino)terephthalic acid diethyl ester was incorporated as emitter substance between the hole conductor and the electron conductor. The device was also tested applying an adjustable voltage between 0 and 15 V. The device emits a wavelength of 618 nm (red). A luminance (emission intensity) of 100 cd/m$^2$ was achieved at 9.5 V. The maximum luminance (emission intensity) achieved was 644 cd/m$^2$.

EXAMPLE 7

(Device: Substance 1.5)

The device has the same structure as those of Examples 5 and 6. The emitter substance used was 2,5-bis-(N-phenylamino)-terephthalic acid diethyl ester. Once again, the device was tested applying an adjustable voltage between 0 and 15 V. The device emits a yellow light (578 nm). A luminance (emission intensity) of 100 cd/m$^2$ was achieved at 5.6 V. The maximum luminance (emission intensity) recorded was 5,300 cd/m$^2$.

EXAMPLE 8

(Device: Substance 1.2)

Analogously to Examples 5–7 and according to the same structural principle, a 5 run thick layer of N,N'-dimethyl-2, 5-bis-(N-(2-fluorophenyl)-amino)terephthalic acid dimethyl ester was deposited onto the hole transport layers. The arrangement (FIG. 2) was tested applying an adjustable voltage between 0 and 15 V. The device emits a green light ($\lambda_{max}$=547 nm). A luminance (emission intensity) of 100 cd/m$^2$ was achieved at 5.4 V. The maximum luminance (emission intensity) achieved was 17,700 cd/m$^2$.

1. The substrate consists of glass;
2. The anode consists of ITO;

3. 1-Naphdata is applied as hole conductor;
4. Another hole conductor layer consists of α-NPD;
5. One or several emitter layers are arranged between the hole conductor and the electron conductor;
6. The electron conductor can e.g. consist of Alq3;
7. The buffer layer consists of LiF;
8. The cathode consists of a base metal or an alloy (e.g. aluminium or calcium).

Typically, the emitter layers are 3–10 nm thick, preferably 4–6 nm.

TABLE 2

Photometric parameters of selected emitter substances

| | 1)V | 2)nm | Colour | 3)cd/m² | 4)cd/A | 5)lm/W |
|---|---|---|---|---|---|---|
| 1.21 | 9.2 | 629 | red-white | 1980 | 0.12 | 0.07 |
| 1.16*) | 9.3 | 634 | red-white | 3990 | 0.14 | 0.10 |
| 1.16 | 14.0 | 618 | red | 144 | 0.09 | 0.07 |
| 1.30 | 5.6 | 612 | orange-red | 12100 | 2.17 | 2.27 |
| 19.4 | 5.0 | 578 | yellow | 11400 | 2.04 | 1.72 |
| 1.5 | 5.6 | 578 | yellow | 5300 | 1.59 | 1.42 |
| 1.4 | 8.0 | 577 | yellow | 1410 | 0.81 | 0.37 |
| 19.3 | 6.5 | 565 | yellow-green | 4530 | 0.72 | 0.49 |
| 1.3 | 8.1 | 577 | yellow-green | 4330 | 2.77 | 1.52 |
| 19.7 | 10.2 | | yellow-green | 474 | 0.26 | 0.10 |
| 1.34 | 3.5 | 550 | green | 36500 | 1.00 | 9.21 |
| 1.36 | 5.7 | 546 | green | 18100 | 6.60 | 4.34 |
| 1.2 | 5.4 | 547 | green | 17700 | 7.70 | 4.93 |
| 1.38 | 6.4 | 546 | green | 11300 | 4.62 | 2.47 |
| 19.2 | 6.6 | 564 | green | 6010 | 0.89 | 0.66 |
| 19.1 | 6.7 | 540 | green | 4680 | 3.05 | 1.70 |
| 19.6 | 8.6 | 545 | green | 2610 | 0.52 | 0.36 |
| 1.29 | 11.1 | 564 | green | 1330 | 1.59 | 0.47 |
| 1.1 | 7.1 | 538 | green | 1300 | 0.48 | 0.22 |
| 1.33 | 10.3 | 563 | green | 1100 | 1.53 | 0.54 |
| 1.31 | 10.8 | 566 | green | 754 | 1.60 | 0.53 |
| 19.8 | 13.4 | | green | 273 | 1.20 | 0.70 |
| 19.11 | 14.4 | 532 | green | 144 | 0.03 | 0.01 |
| 19.5 | >20.0 | 540 | green | 8 | 0.30 | 0.28 |
| 19.9 | >15.0 | 544 | green | 64 | 0.58 | 0.13 |

1)voltage at 100 cd/m²
2)λ$_{max}$ of electroluminescence
3)max. luminance (emission intensity)
4)max. photometric efficiency
5)max. performance efficiency

TABLE 3

Absorption and emission maxima of selected emitter substances

| | λ$_{max}$ (solid) | λ$_{em}$ (solid) | | λ$_{max}$ (solid) | λ$_{em}$ (solid) | | λ$_{max}$ (solid) | λ$_{em}$ (solid) |
|---|---|---|---|---|---|---|---|---|
| 1.6 | | 614 | 1.19 | 435 | 531 | 1.6 | | 623 |
| 1.7 | | 597 | 1.4 | | 599 | 19.6 | | 592 |
| 1.8 | | 604 | 1.20 | | 596 | 1.28 | | 588 |
| 1.10 | | 626 | 19.1 | 475 | 564 | 1.3 | | 595 |
| 1.11 | | 596 | 19.4 | 460 | 598 | 1.24 | | 612 |
| 1.12 | | 586 | 1.5 | 465 | 582 | 19.8 | 453 | 583 |
| 1.1 | | 547 | 1.21 | 495 | 625 | 1.2 | | 558 |
| 1.13 | | 559 | 19.5 | | 612 | .5 | 496 | 622 |
| 1.14 | | 543 | 1.23 | | 573 | | | |
| 1.15 | | 605 | 1.24 | | 564 | | | |
| 1.16 | 500 | 635 | 1.25 | | 605 | | | |
| 1.17 | | 596 | 1.26 | | 602 | | | |
| 1.18 | | 617 | 19.3 | | 582 | | | |

λ$_{max}$: absorption maximum
λ$_{em}$: emission maximum
λ$_{ell}$: maximum of electroluminescence

TABLE 4

Absorbance coefficients ε of selected emitter substances

| # | λ$_{max}$ (nm) | ε (l · mol⁻¹ cm⁻¹) | Solvent |
|---|---|---|---|
| 1.16 | 489 | 6000 | CHCl₃ |
| 1.5 | 469 | 6640 | CHCl₃ |
| 1.34 | 403 | 4744 | NMP |
| 19.6 | 452 | 5250 | CHCl₃ |
| 19.5 | 474 | 4670 | CHCl₃ |
| 19.7 | 433 | 5450 | NMP |
| 1.17 | 472 | 6410 | CHCl₃ |
| 1.15 | 486 | 5930 | CHCl₃ |
| 1.12 | 460 | 5930 | CHCl₃ |
| 1.11 | 481 | 6840 | CHCl₃ |
| 1.8 | 472 | 6450 | CHCl₃ |
| 1.7 | 474 | 6550 | CHCl₃ |
| 19.1 | 434 | 4700 | NMP |
| 1.30 | 493 | 5450 | NMP |
| 1.27 | 482 | 6800 | CHCl₃ |

TABLE 5

Absorption maxima of selected emitter substances in solution

| | λ$_{max}$ (NMP) | | λ$_{max}$ (NMP) | | λ$_{max}$ (NMP) |
|---|---|---|---|---|---|
| 1.6 | 482 | 1.19 | 417 | 1.6 | 481 |
| 1.7 | 476 | 1.4 | 468 | 19.6 | 452 |
| 1.8 | 463 | 1.20 | 461 | 1.28 | 473 |
| 1.9 | 652 | 19.1 | 435 | 1.3 | 451 |
| 1.10 | 509 | 19.4 | 458 | 1.24 | 480 |
| 1.11 | 475 | 1.5 | 451 | 1.30 | 493 |
| 1.12 | 445 | 1.21 | 479 | 1.34 | 403 |
| 1.1 | 413 | 1.22 | 505 | .5 | 461 |
| 1.13 | 427 | 19.5 | 472 | 1.43 | 496 |
| 1.14 | 428 | 1.23 | 432 | | |
| 1.15 | 482 | 1.24 | 446 | | |
| 1.16 | 494 | 1.25 | 487 | | |
| 1.17 | 464 | 1.26 | 482 | | |
| 1.18 | 464 | 19.3 | 447 | | |

TABLE 6

DSC values of selected emitter substances

| # | DSC peak in ° C. |
|---|---|
| 19.3 | 260.0 |
| 1.6 | 269.1 |
| 1.7 | 171.3 |
| 1.8 | 227.8 |
| 1.11 | 192.1 |
| 1.12 | 172.2 |
| 1.15 | 232.0 |
| 1.17 | 166.5 |
| 19.1 | 325.7 |
| 1.16 | 183.3 |
| 1.34 | 254.7 |
| 19.1 | 325.7 |
| 1.27 | 182.5 |

Preparation and Measuring Conditions a) Substrate: 125 nm ITO, approx. 13 Ω/sq and 85% tranmission, 50×50 mm² glass substrate (1.1 mm thick polished soda-lime float glass with $SiO_2$ layer and 8 individual ITO anodes (active surface area: 2×2 mm²))

Purified 2×20 min in an ultrasonic bath with Aceton selectopur and Methanol selectopur, 3×snow jet cleaning ($CO_2$ ice crystals)

$O_2$ plasma treatment (5 min at 450 W and 0.12 mbar)

b) Pressure $(2-4) \times 10^{-5}$ mbar during deposition

Aluminium oxide ceramic crucible

Deposition rate: 0.06 nm/s

Layer thickness checked using a piezoelectric microbalance measuring device

Change of mask and intermediate aeration of the deposition chamber, first with nitrogen and then with air Cathodes, 0.5 nm lithium fluoride (insulating) and 100 nm aluminium each c) The device according to FIG. 2 was introduced in a glove box, the active OLED surface was positioned above calibrated $V_\lambda$ silicon photodiodes in a darkened measuring device, and the anode (ITO-) and cathode (Al—) contacts were brought in contact with gilded spring electrodes.

Programmable voltage supply (SMU) and digital multimeter for recording and processing the OLED curve in a PC via GPIB-BUS and LabView program Voltage pulse operation (pulses lasting 1s) between −10 V and +15 V (0.5 V increments): current density-voltage curve and luminance (emission intensity)-voltage curve as well as the calculated photometric efficiency values (in cd/A) and performance efficiency values (in lm/W) as a function of U d) Wavelength of maximum by recording the electroluminescence spectrum using an Xdap diode array spectrometer

TABLE 1

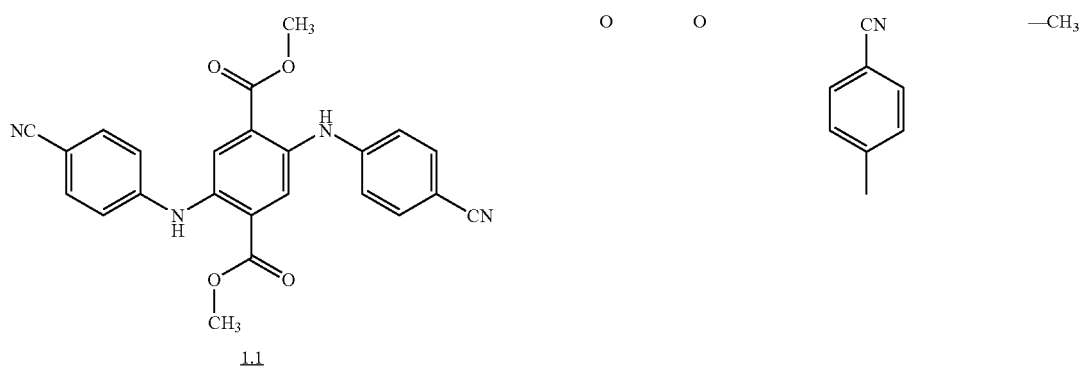

TABLE 1-continued
2,5-diaminoterephthalic acid derivatives
| | | | |
|---|---|---|---|
| 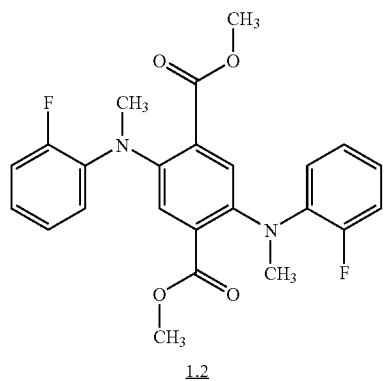<br>1.2 | O | O | 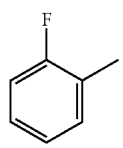 | —CH₃ |
| 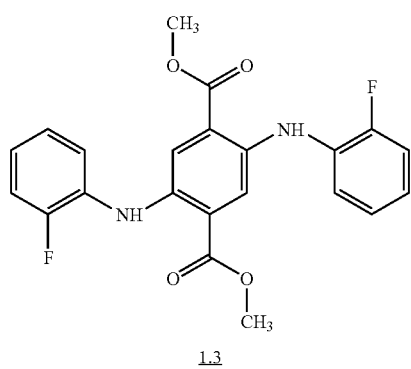<br>1.3 | O | O | 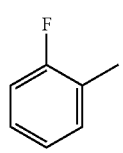 | —CH₃ |
| 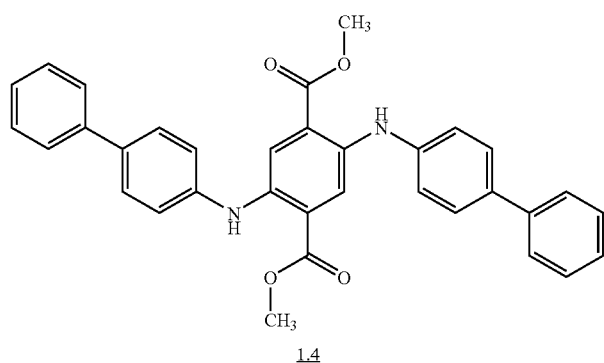<br>1.4 | O | O | 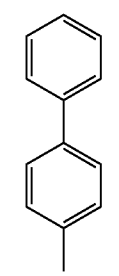 | —CH₃ |
| 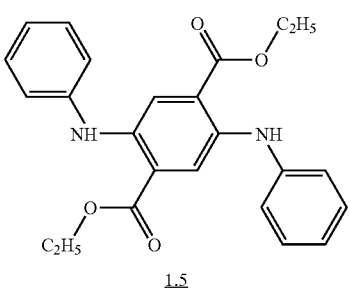<br>1.5 | O | O | 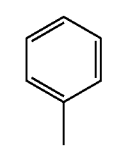 | —C₂H₅ |

TABLE 1-continued
2,5-diaminoterephthalic acid derivatives
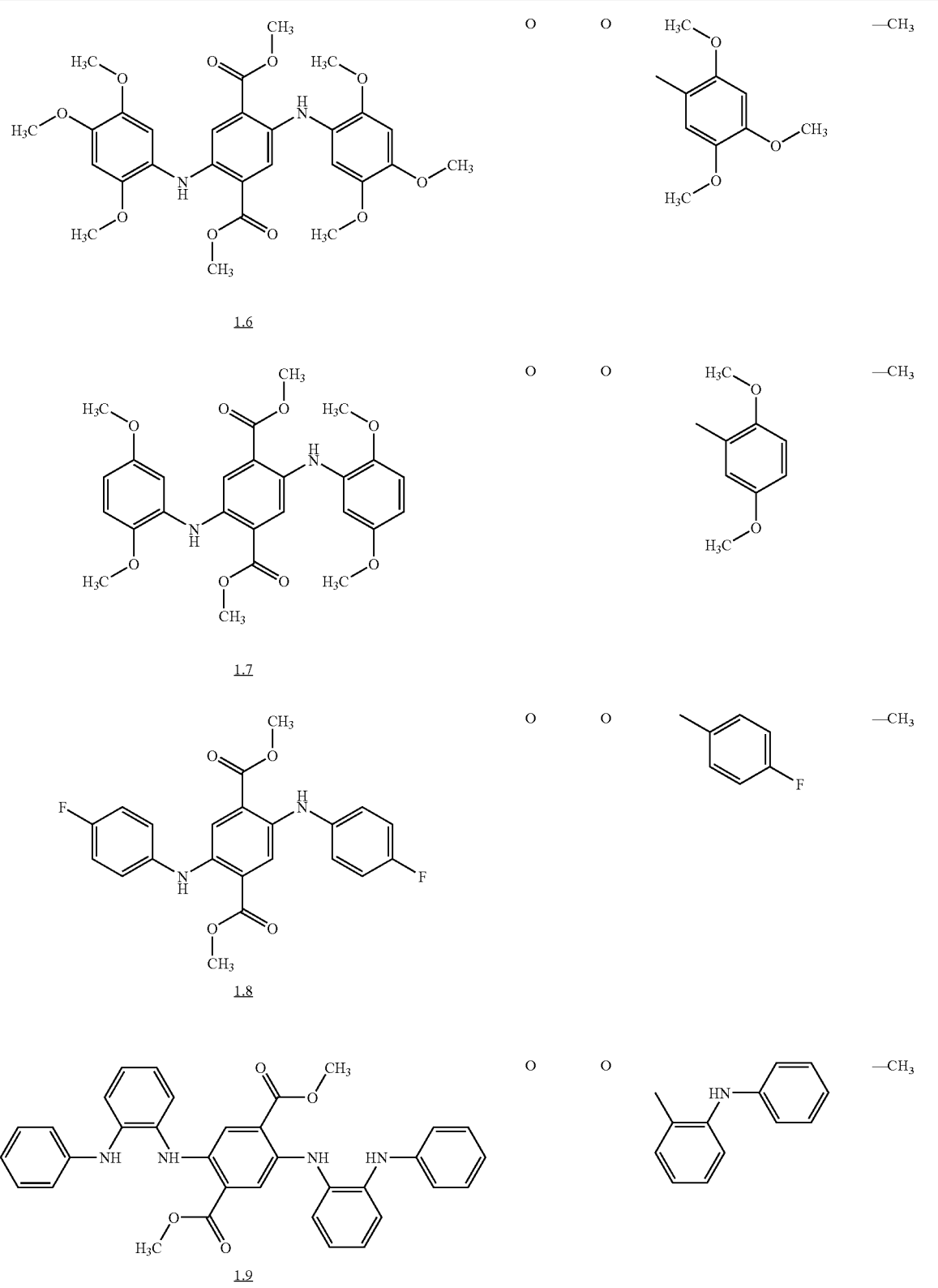

TABLE 1-continued
2,5-diaminoterephthalic acid derivatives
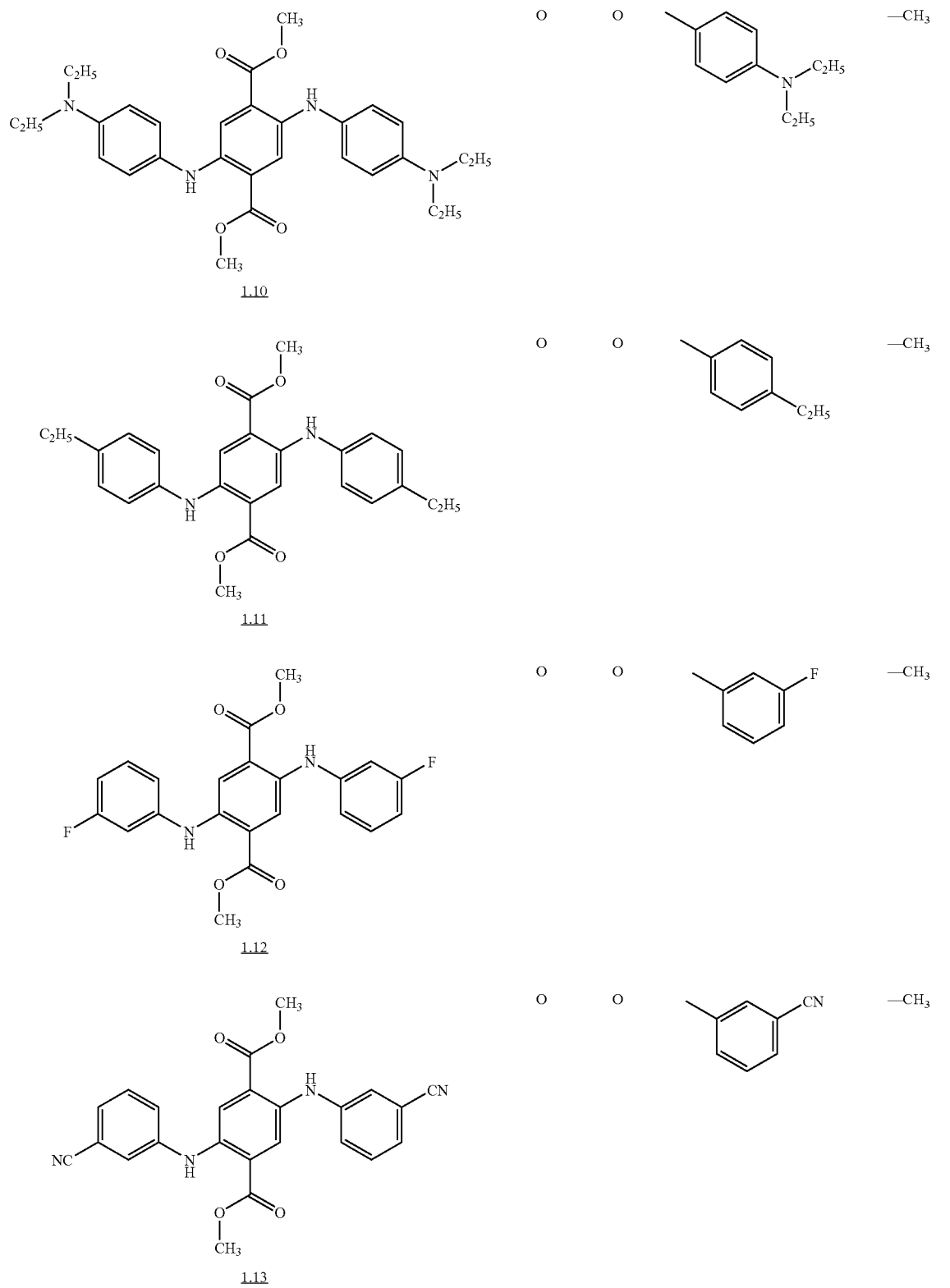

TABLE 1-continued
2,5-diaminoterephthalic acid derivatives
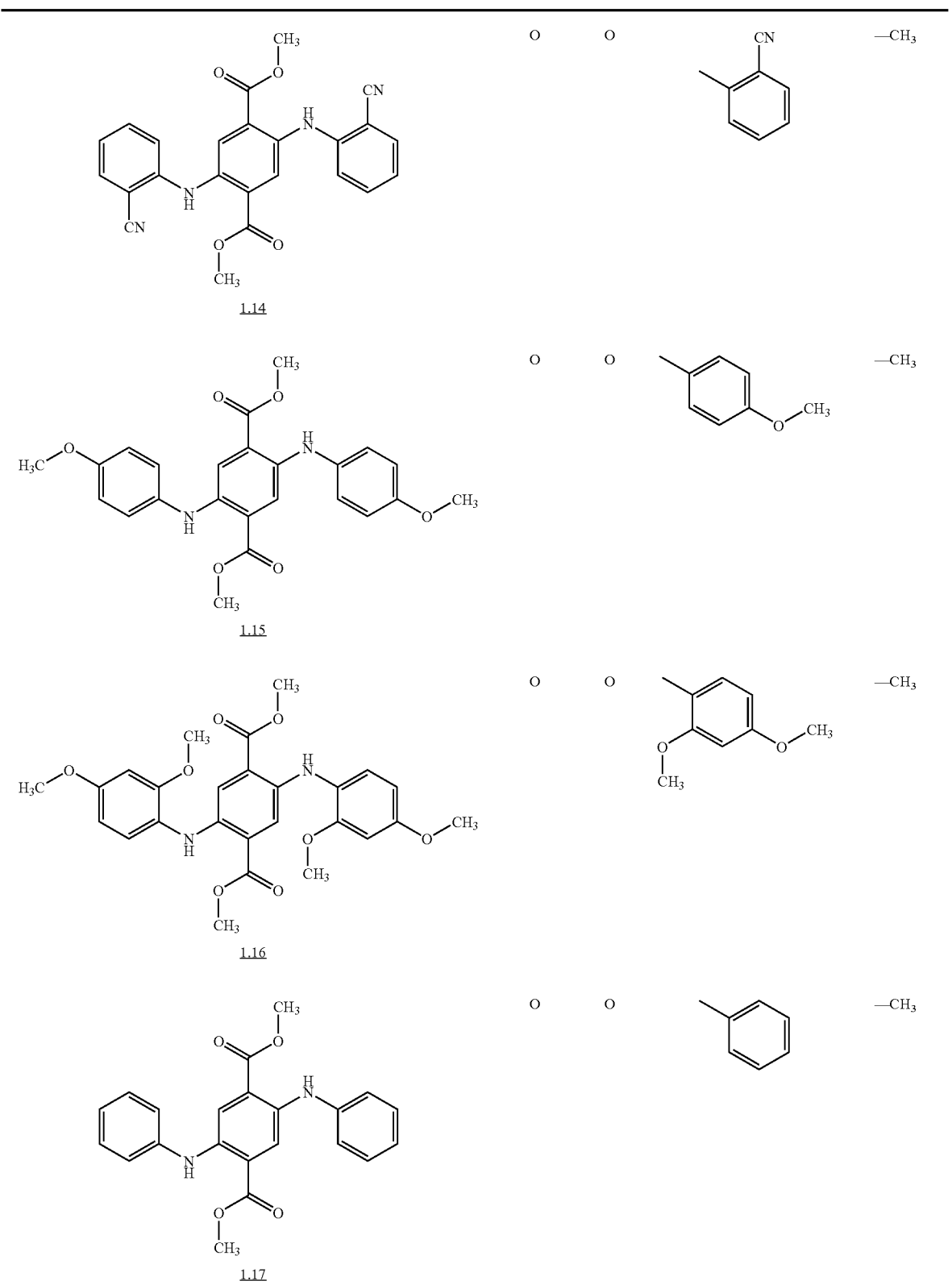

TABLE 1-continued
2,5-diaminoterephthalic acid derivatives
| | | | |
|---|---|---|---|
| 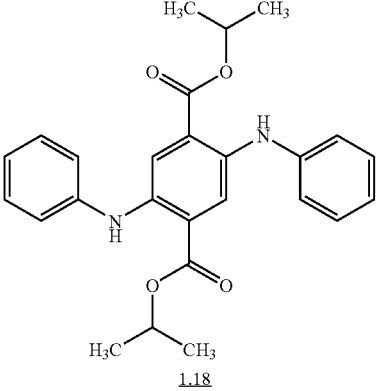 1.18 | O | O |  —CH₃ |
|  1.19 | O | O | 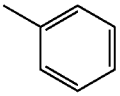 —CH₃ |
|  1.20 | O | O | 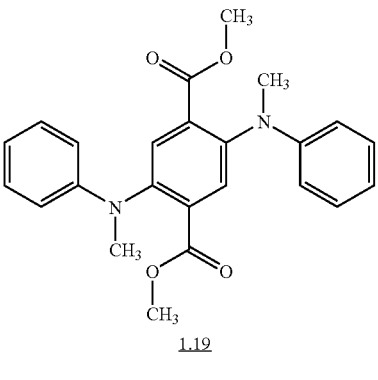 —CH₃ |
|  1.21 | O | O |  —CH₃ |

TABLE 1-continued
2,5-diaminoterephthalic acid derivatives
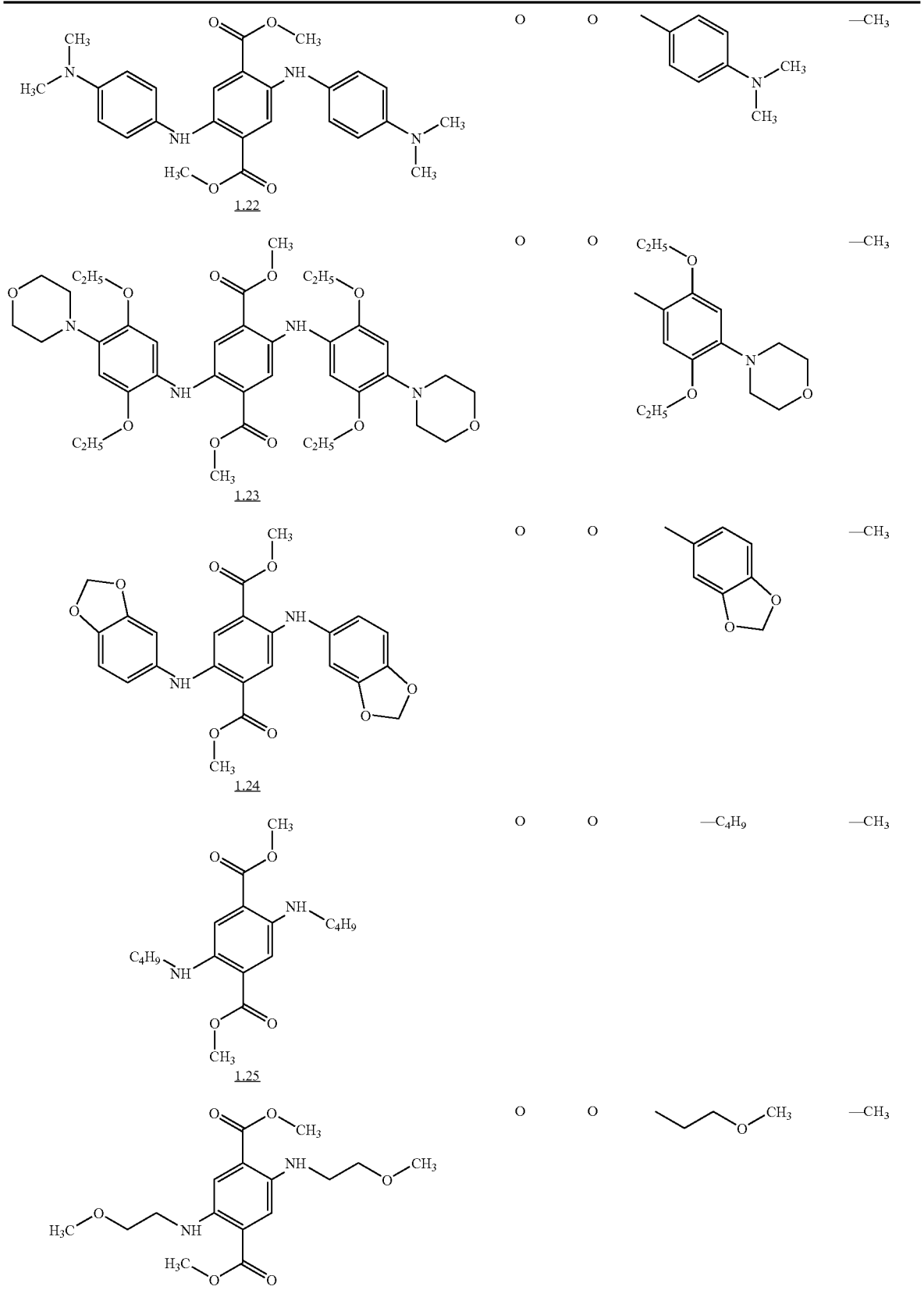

TABLE 1-continued
2,5-diaminoterephthalic acid derivatives
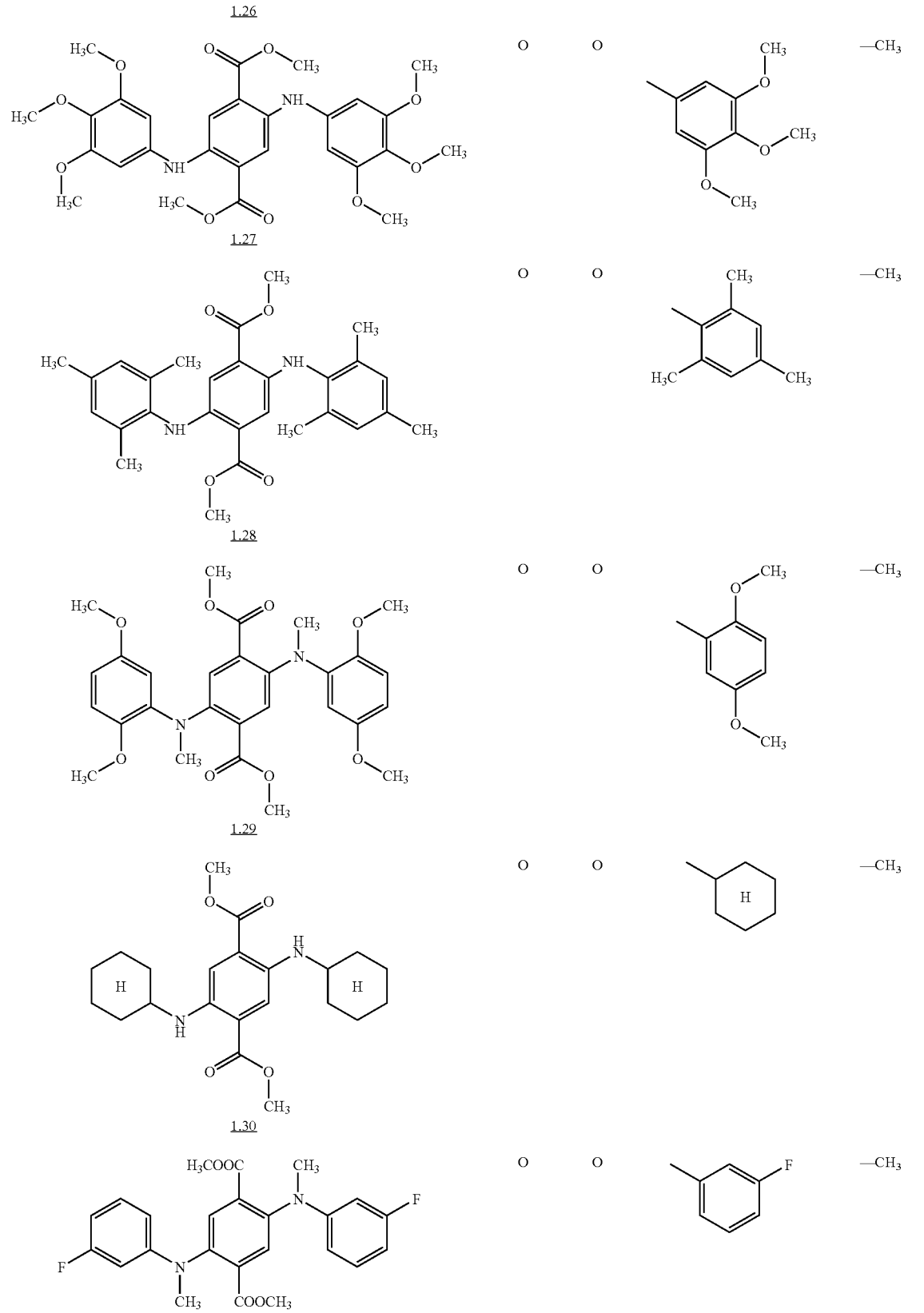

TABLE 1-continued
2,5-diaminoterephthalic acid derivatives
1.31
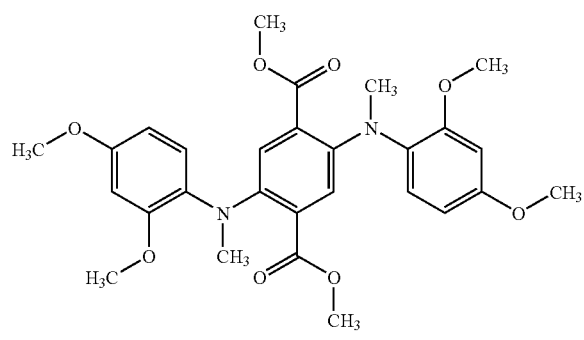
1.32
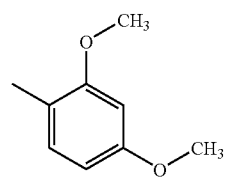 —CH₃
O  O
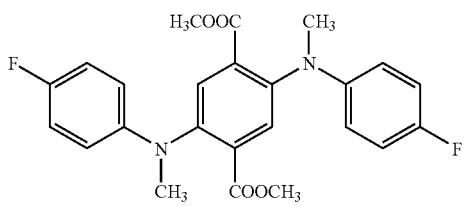
1.33
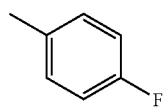 —CH₃
O  O
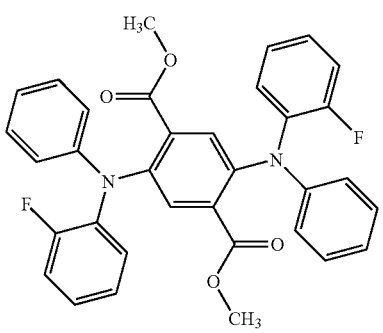
1.34
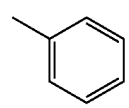 —CH₃
O  O
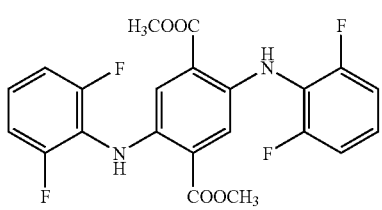
1.35
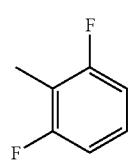 —CH₃
O  O
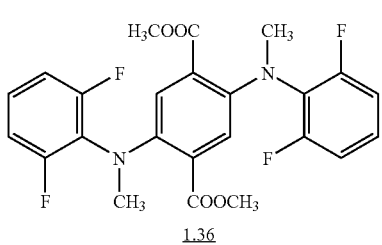
1.36
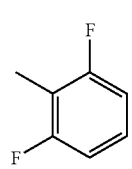 —CH₃
O  O TABLE 1-continued
| 2,5-diaminoterephthalic acid derivatives | | | | |
|---|---|---|---|---|
| 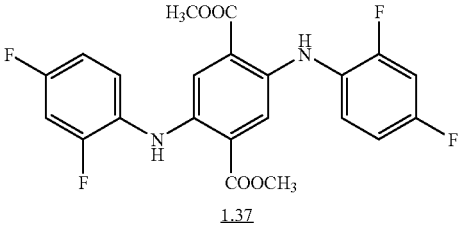 1.37 | O | O |  | —CH₃ |
| 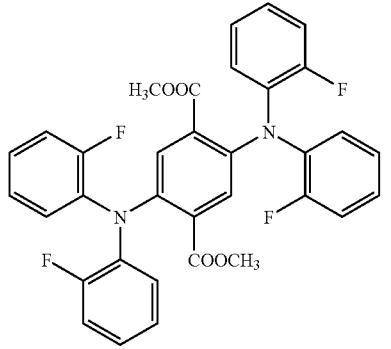 1.38 | O | O | 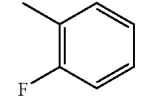 | —CH₃ |
| 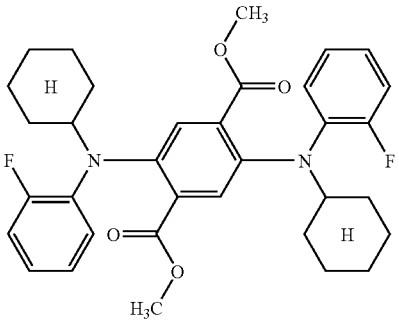 1.39 | O | O | 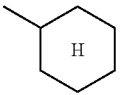 | —CH₃ |
| 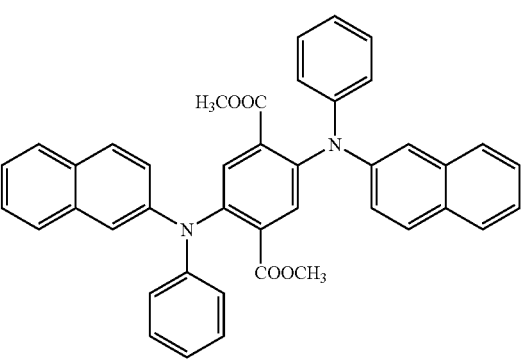 1.40 | O | O | 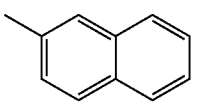 | —CH₃ |

TABLE 1-continued
2,5-diaminoterephthalic acid derivatives
| | | | |
|---|---|---|---|
| 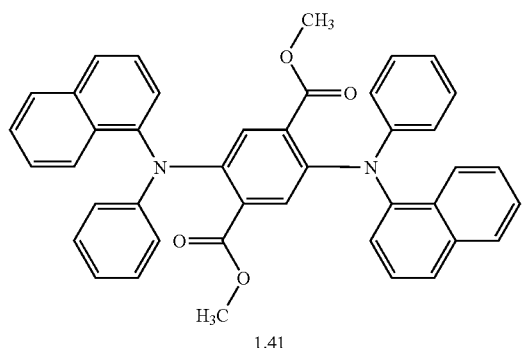 1.41 | O | O 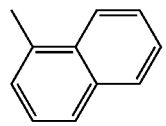 | —CH₃ |
| 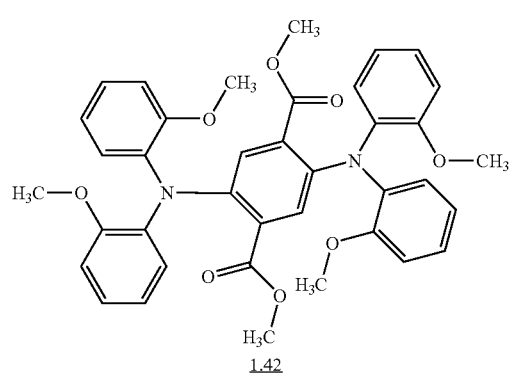 1.42 | O | O 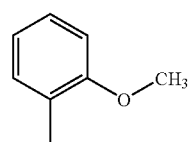 | —CH₃ |
| 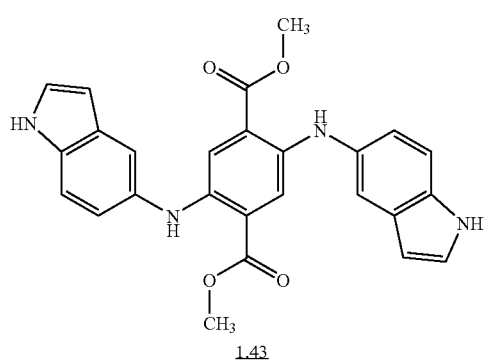 1.43 | O | O 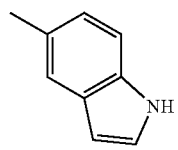 | —CH₃ |
| 1.44 | O | O 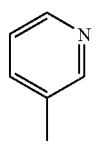 | —CH₃ |
| 1.45 | O | O 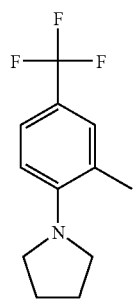 | —CH₃ |

TABLE 1-continued
| 2,5-diaminoterephthalic acid derivatives | | | | |
|---|---|---|---|---|
| 1.46 | O | O | 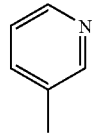 | —CH₃ |
| 1.47 | O | O | 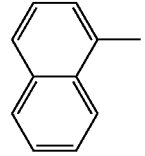 | —CH₃ |
| 1.48 | O | O | 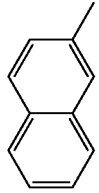 | —CH₃ |
| 1.49 | O | O | 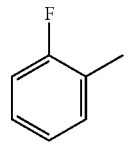 | —CH₃ |
| 1.50 | O | O | 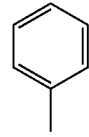 | —CH₃ |
| 1.51 | O | O | 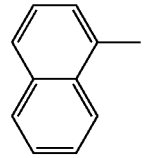 | —CH₃ |
| 1.52 | O | O | 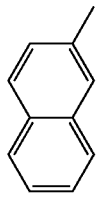 | —CH₃ |
| 1.53 | O | O | 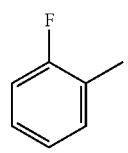 | —CH₃ |
| 1.54 | O | O | 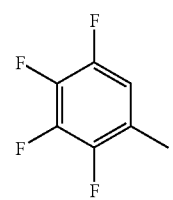 | —CH₃ |

TABLE 1-continued
| | | | 2,5-diaminoterephthalic acid derivatives | |
|---|---|---|---|---|
| 1.55 | O | O | 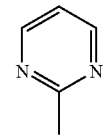 | —CH₃ |
| 1.56 | O | O | 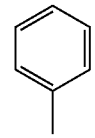 | —CH₃ |
| 1.57 | O | O | 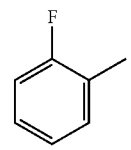 | —CH₃ |
| 1.58 | O | O | 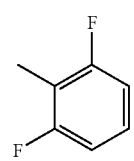 | —CH₃ |
| 1.59 | O | O | 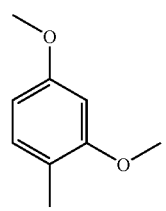 | —CH₃ |
| 1.60 | O | O | 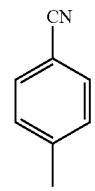 | —CH₃ |
| 1.61 | O | O | 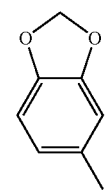 | —CH₃ |
| 1.62 | O | O | 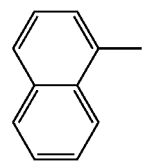 | —CH₃ |

TABLE 1-continued
| 2,5-diaminoterephthalic acid derivatives | | | | |
|---|---|---|---|---|
| 1.63 | O | O | (1-methylnaphthyl) | —CH₃ |
| 1.64 | O | O | (2,3,4,5-tetrafluoro-methylphenyl) | —CH₃ |
| 1.65 | O | O | (pentafluoromethylphenyl) | —CH₃ |
| 1.67 | O | O | (pentafluoromethylphenyl) | —CH₃ |
| 1.68 | O | O | (julolidinyl-methyl) | —CH₃ |
| Substance | R² | R⁴ | X⁴ | X³ | R⁸ |
|---|---|---|---|---|---|
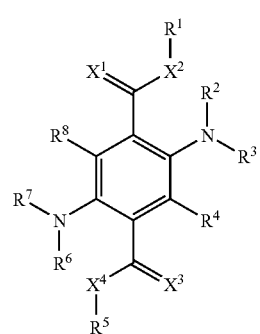
1.0

TABLE 1-continued 2,5-diaminoterephthalic acid derivatives

| Structure | | | | | |
|---|---|---|---|---|---|
| 1.1 | H | H | O | O | H |
| 1.2 | —CH₃ | H | O | O | H |
| 1.3 | H | H | O | O | H |
| 1.4 | H | H | O | O | H |

TABLE 1-continued
2,5-diaminoterephthalic acid derivatives
| | | | | | |
|---|---|---|---|---|---|
| 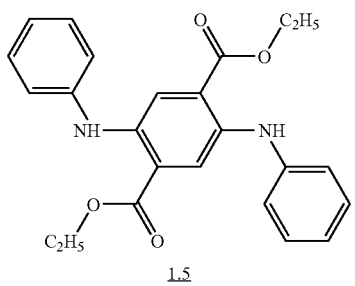<br>1.5 | H | H | O | O | H |
| 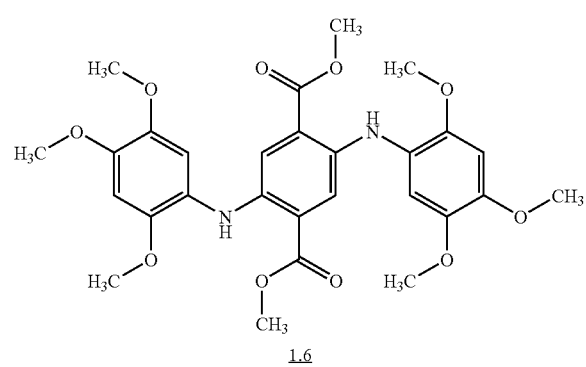<br>1.6 | H | H | O | O | H |
| 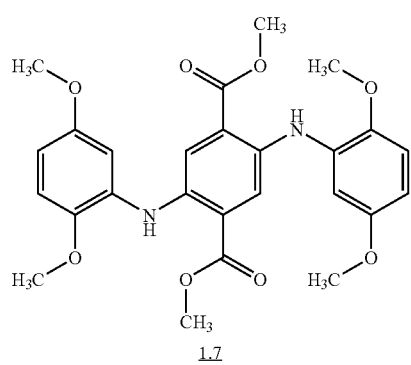<br>1.7 | H | H | O | O | H |
| 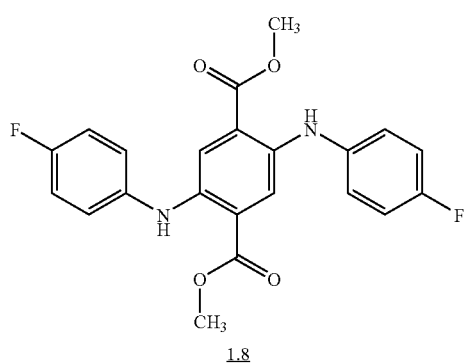<br>1.8 | H | H | O | O | H |

TABLE 1-continued
2,5-diaminoterephthalic acid derivatives
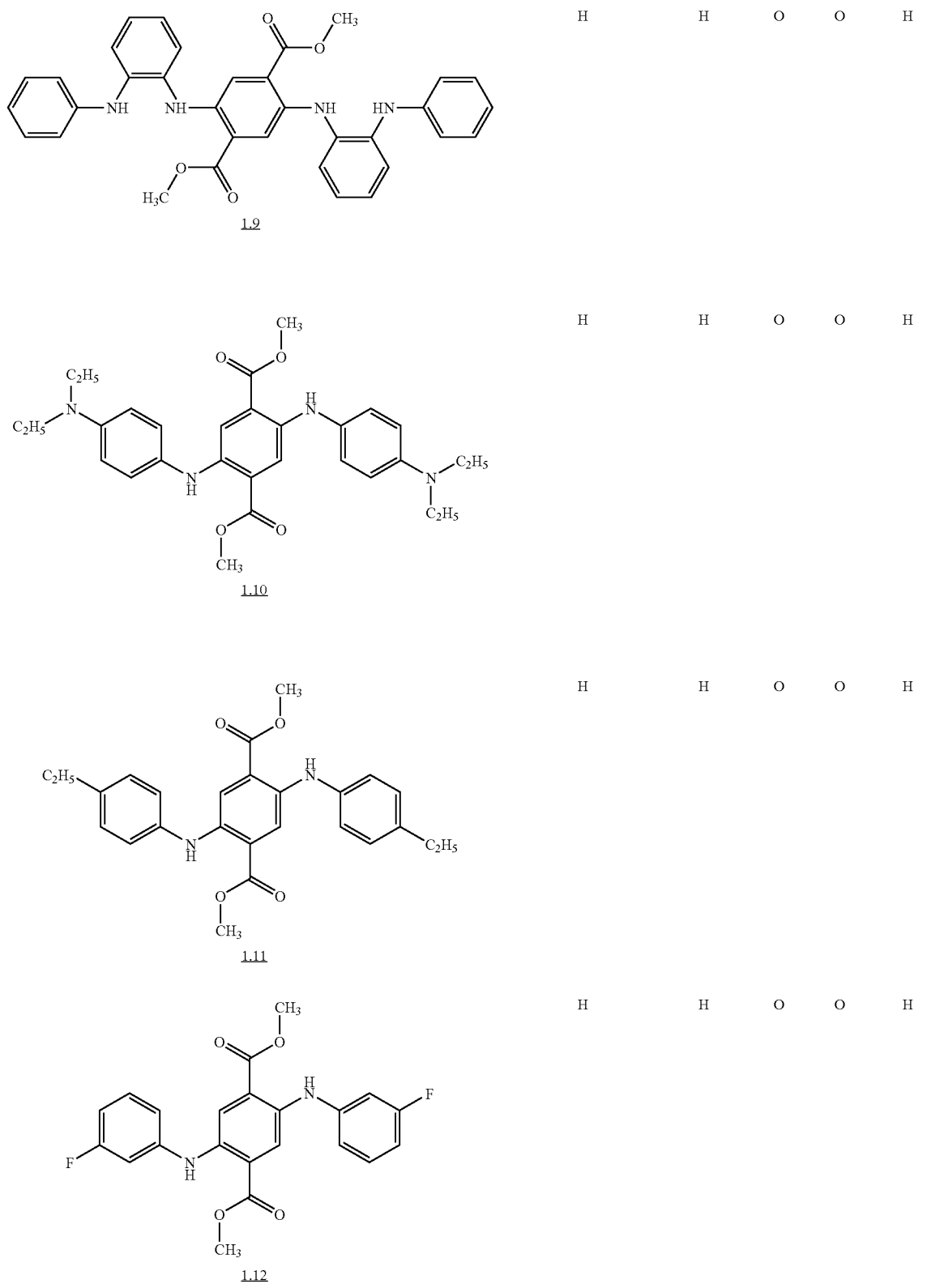
| | | | | |
|---|---|---|---|---|
| H | H | O | O | H |
| H | H | O | O | H |
| H | H | O | O | H |
| H | H | O | O | H |

TABLE 1-continued
2,5-diaminoterephthalic acid derivatives
| | | | | | | |
|---|---|---|---|---|---|---|
| 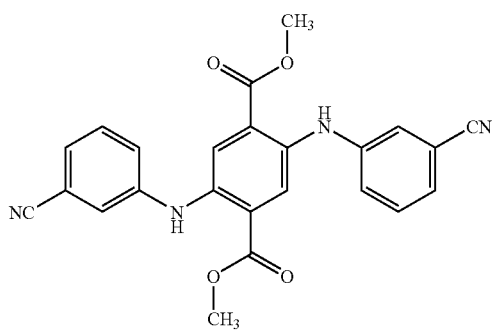 1.13 | H | H | O | O | H |
| 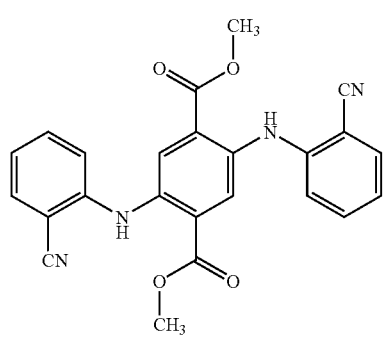 1.14 | H | H | O | O | H |
| 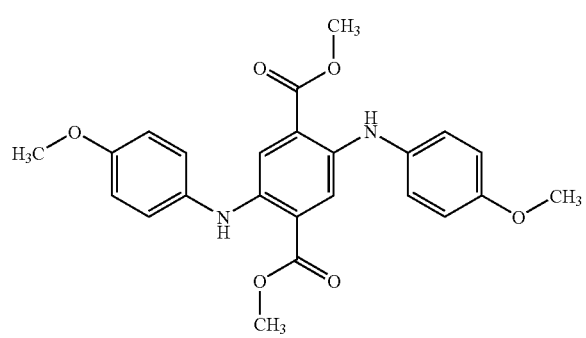 1.15 | H | H | O | O | H |
| 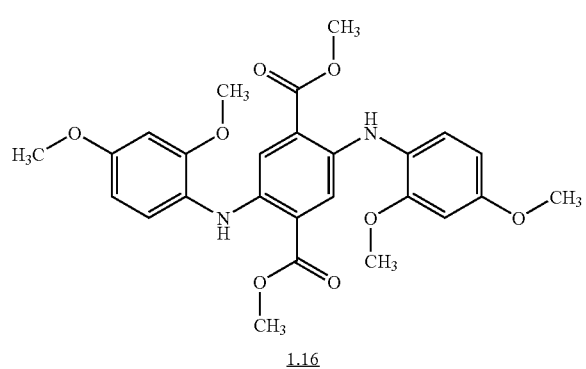 1.16 | H | H | O | O | H |

TABLE 1-continued
2,5-diaminoterephthalic acid derivatives
| | | | | | |
|---|---|---|---|---|---|
| 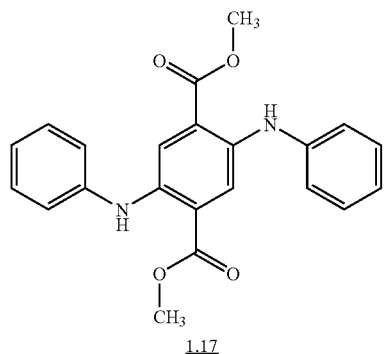<br>1.17 | H | H | O | O | H |
| 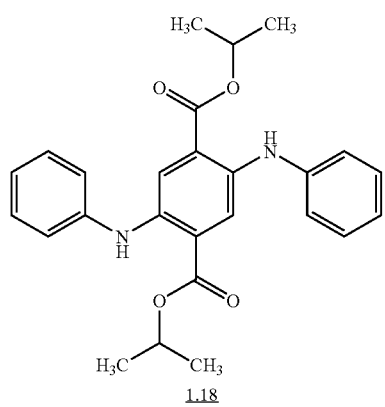<br>1.18 | H | H | O | O | H |
| 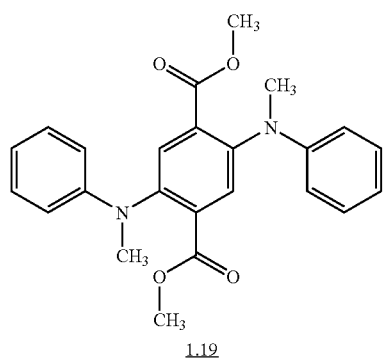<br>1.19 | —CH$_3$ | H | O | O | H |
| 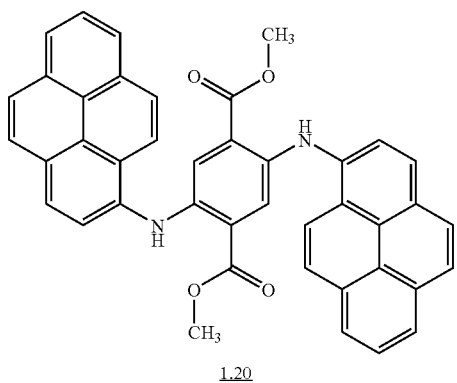<br>1.20 | H | H | O | O | H |

TABLE 1-continued
2,5-diaminoterephthalic acid derivatives
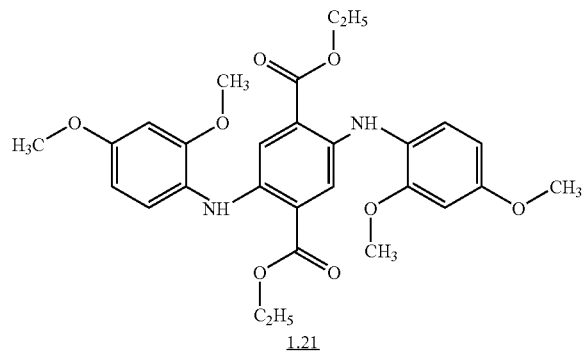
1.21
H H O O H
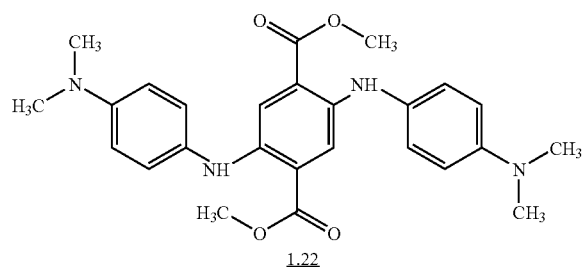
1.22
H H O O H
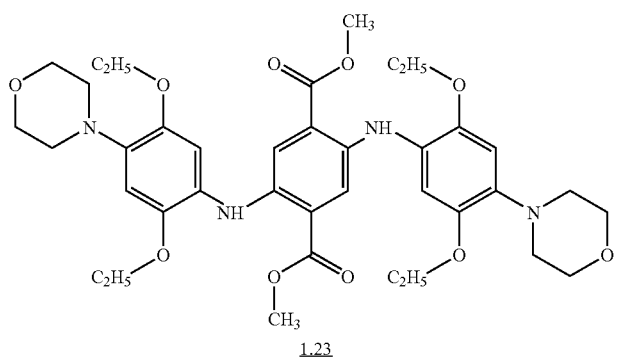
1.23
H H O O H
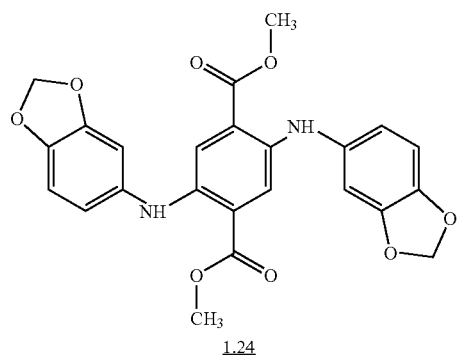
1.24
H H O O H TABLE 1-continued

| 2,5-diaminoterephthalic acid derivatives | | | | | |
|---|---|---|---|---|---|
| 1.25 | H | H | O | O | H |
| 1.26 | H | H | O | O | H |
| 1.27 | H | H | O | O | H |
| 1.28 | H | H | O | O | H |
| (structure) | —CH₃ | H | O | O | H |

TABLE 1-continued
2,5-diaminoterephthalic acid derivatives
1.29
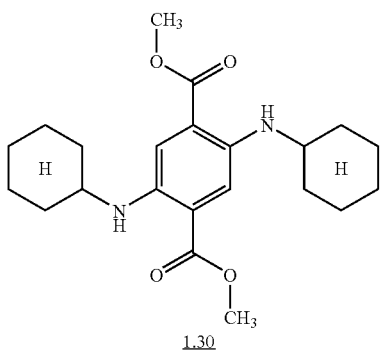
| H | H | O | O | H |
1.30
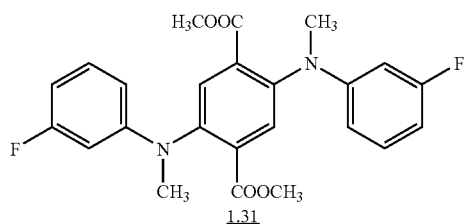
| —CH₃ | H | O | O | H |
1.31
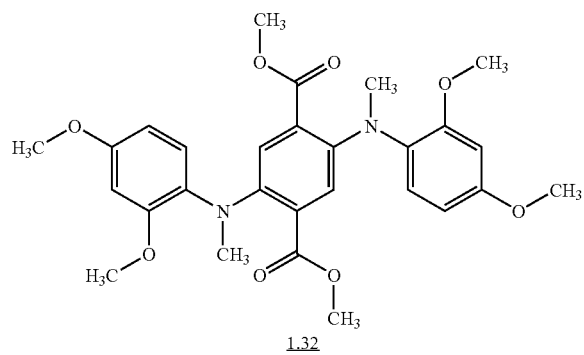
| —CH₃ | H | O | O | H |
1.32
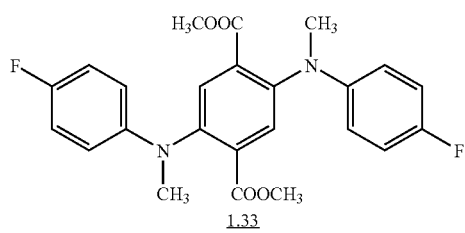
| —CH₃ | H | O | O | H |
1.33
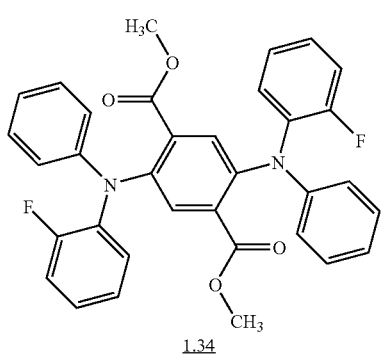
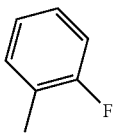 | H | O | O | H |
1.34

TABLE 1-continued 2,5-diaminoterephthalic acid derivatives

| Structure | | | | | |
|---|---|---|---|---|---|
| 1.35 | H | H | O | O | H |
| 1.36 | —CH₃ | H | O | O | H |
| 1.37 | H | H | O | O | H |
| 1.38 | (2-fluorophenyl) | H | O | O | H |
| 1.39 | (2-fluorophenyl) | H | O | O | H |

TABLE 1-continued 2,5-diaminoterephthalic acid derivatives

| | | | | | |
|---|---|---|---|---|---|
| 1.40 (structure: dimethyl 2,5-bis(N-phenyl-N-(2-naphthyl)amino)terephthalate) | toluene | H | O | O | H |
| 1.41 (structure: dimethyl 2,5-bis(N-phenyl-N-(1-naphthyl)amino)terephthalate) | toluene | H | O | O | H |
| 1.42 (structure: dimethyl 2,5-bis(N,N-bis(2-methoxyphenyl)amino)terephthalate) | 2-methoxytoluene | H | O | O | H |
| 1.43 (structure: dimethyl 2,5-bis((1H-indol-5-yl)amino)terephthalate) | H | H | O | O | H |
| 1.44 | —CH₃ | H | O | O | H |
| 1.45 | —CH₃ | H | O | O | H |
| 1.46 | —CH₃ | H | O | O | H |
| 1.47 | —CH₃ | H | O | O | H |
| 1.48 | —CH₃ | H | O | O | H |
| 1.49 | —CH₃ | H | O | O | H |

TABLE 1-continued

| 2,5-diaminoterephthalic acid derivatives | | | | | |
|---|---|---|---|---|---|
| 1.50 | —CF₃ | H | O | O | H |
| 1.51 | —CF₃ | H | O | O | H |
| 1.52 | —CF₃ | H | O | O | H |
| 1.53 | —CF₃ | H | O | O | H |
| 1.54 | —CF₃ | H | O | O | H |
| 1.55 | —CF₃ | H | O | O | H |
| 1.56 | ⌬ | H | O | O | H |
| 1.57 | ⌬ | H | O | O | H |
| 1.58 | ⌬ | H | O | O | H |
| 1.59 | ⌬ | H | O | O | H |
| 1.60 | ⌬ | H | O | O | H |
| 1.61 | ⌬ | H | O | O | H |
| 1.62 | ⌬ | H | O | O | H |
| 1.63 | ⌬ | H | O | O | H |
| 1.64 | ⌬ | H | O | O | H |
| 1.65 | —CH₃ | H | O | O | H |

TABLE 1-continued 2,5-diaminoterephthalic acid derivatives

| | | | | |
|---|---|---|---|---|
| 1.67 | [phenyl/tolyl group] | H | O | O | H |
| 1.68 | [2-fluorotolyl group] | H | O | O | H |

| Substance | R⁵ | R⁶ | R⁷ |
|---|---|---|---|
| 1.0 [general structure] | | | |
| 1.1 [structure] | —CH₃ | H | [4-cyanotolyl group] |
| 1.2 [structure] | —CH₃ | —CH₃ | [2-fluorotolyl group] |

TABLE 1-continued 2,5-diaminoterephthalic acid derivatives

| Structure | | | |
|---|---|---|---|
| 1.3 | —CH₃ | H | 2-fluorophenyl |
| 1.4 | —CH₃ | H | 4-biphenyl |
| 1.5 | —C₂H₅ | H | phenyl |
| 1.6 | —CH₃ | H | 2,4,5-trimethoxyphenyl |

TABLE 1-continued
2,5-diaminoterephthalic acid derivatives
| | | | |
|---|---|---|---|
| 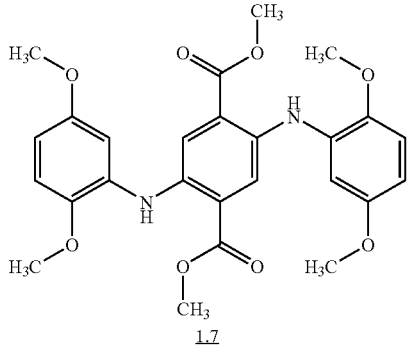 1.7 | —CH$_3$ | H | 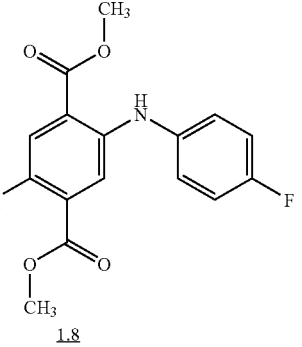 |
| 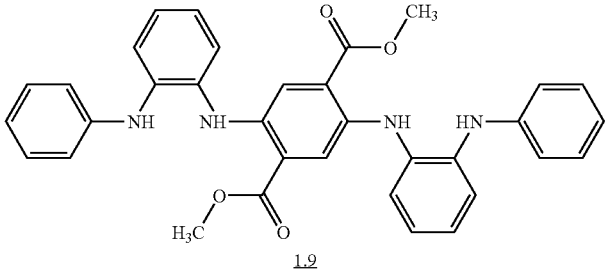 1.8 | —CH$_3$ | H | 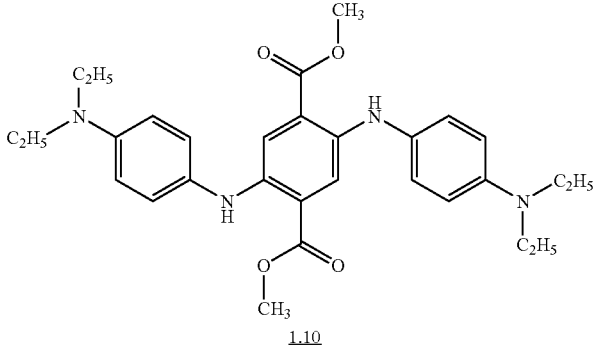 |
| 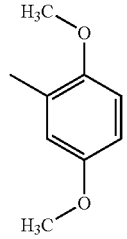 1.9 | —CH$_3$ | H | 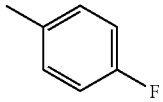 |
| 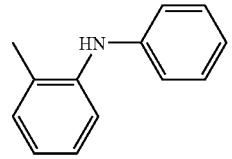 1.10 | —CH$_3$ | H | 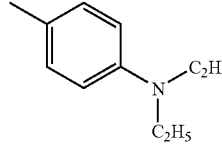 |

TABLE 1-continued
2,5-diaminoterephthalic acid derivatives
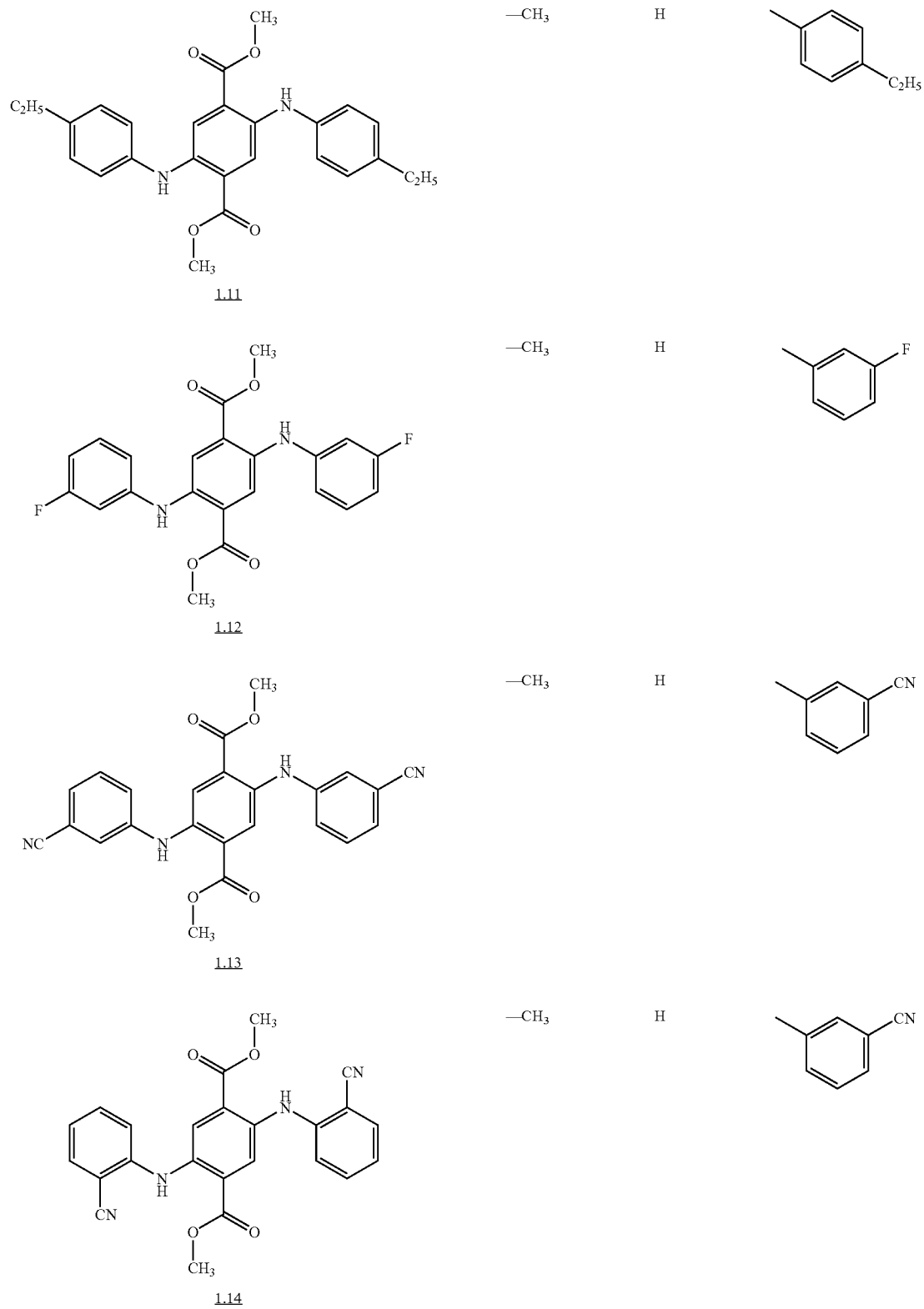

TABLE 1-continued
2,5-diaminoterephthalic acid derivatives
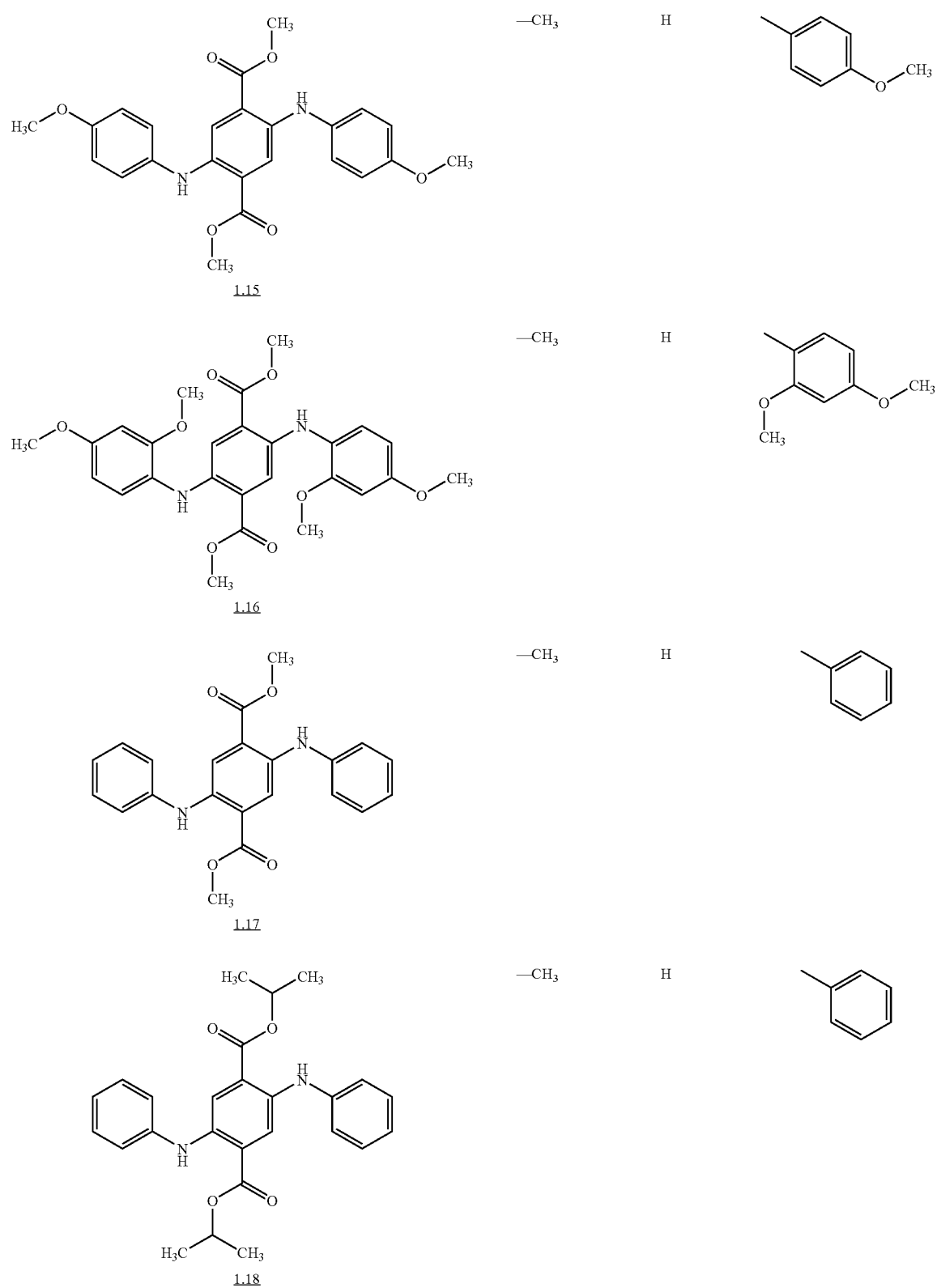

TABLE 1-continued
2,5-diaminoterephthalic acid derivatives
| | | | |
|---|---|---|---|
| 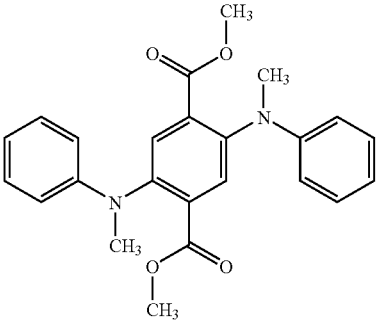 1.19 | —CH₃ | —CH₃ | 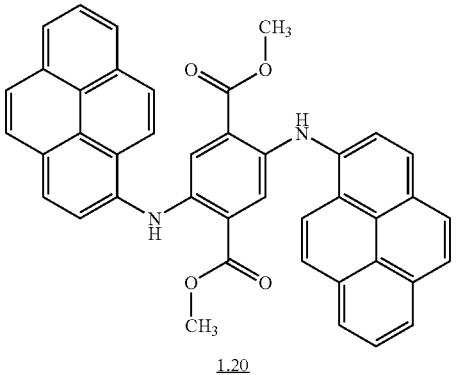 |
| 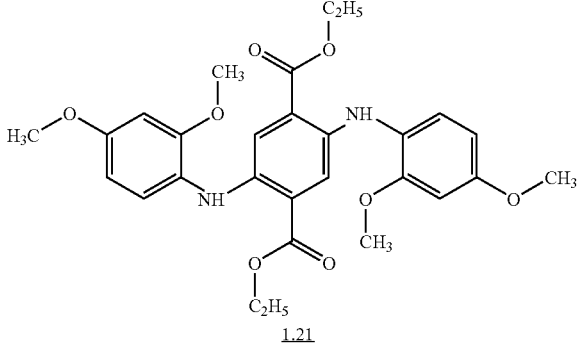 1.20 | —CH₃ | H | 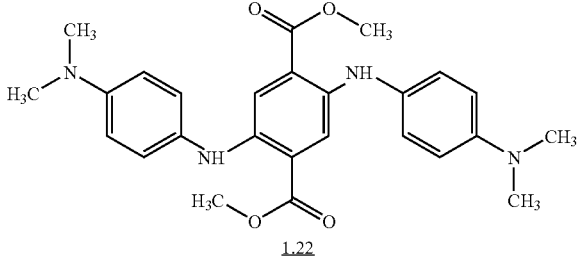 |
| 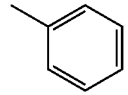 1.21 | —CH₃ | H |  |
|  1.22 | —CH₃ | H |  |

TABLE 1-continued 2,5-diaminoterephthalic acid derivatives

| Structure | | | |
|---|---|---|---|
| 1.23 | —CH₃ | H | (4-morpholino-2,5-diethoxy-methylphenyl) |
| 1.24 | —CH₃ | H | (methylenedioxy-methylphenyl) |
| 1.25 | —CH₃ | H | —C₄H₉ |
| 1.26 | —CH₃ | H | —CH₂CH₂OCH₃ |
| 1.27 | —CH₃ | H | (3,4,5-trimethoxy-methylphenyl) |

TABLE 1-continued
2,5-diaminoterephthalic acid derivatives
1.27
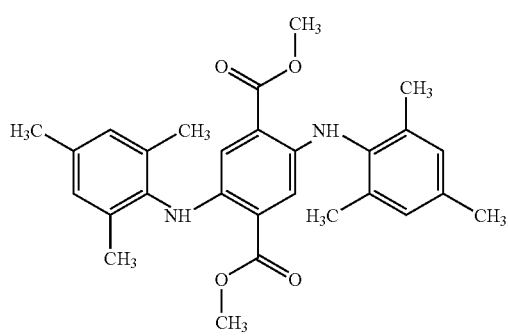
1.28
—CH₃    H    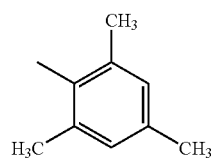
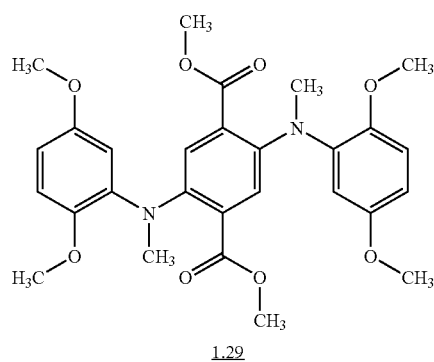
1.29
—CH₃    —CH₃    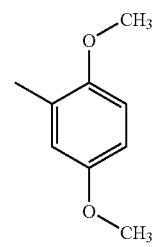
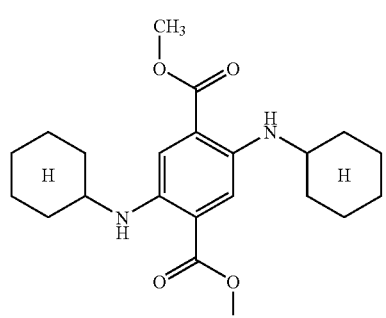
1.30
—CH₃    H    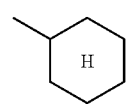
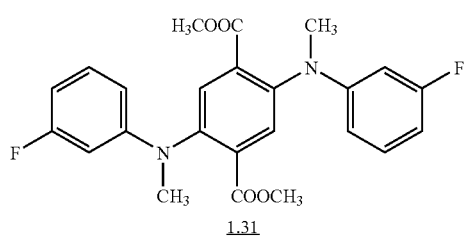
1.31
—CH₃    —CH₃    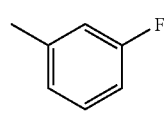

TABLE 1-continued
2,5-diaminoterephthalic acid derivatives
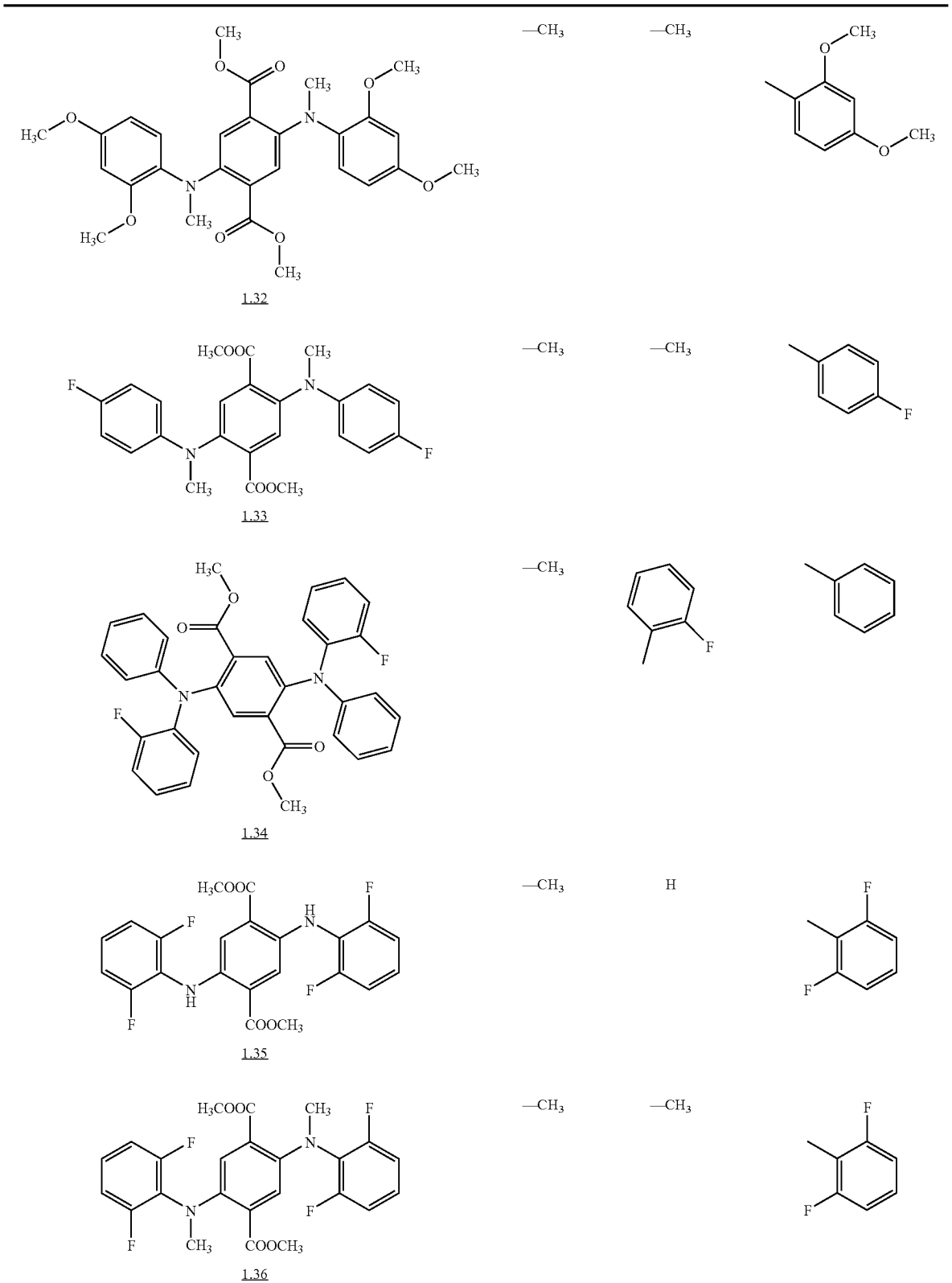

TABLE 1-continued
2,5-diaminoterephthalic acid derivatives
| | | | |
|---|---|---|---|
| 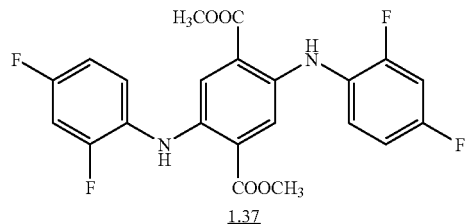<br>1.37 | —CH₃ | H | 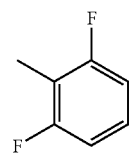 |
| 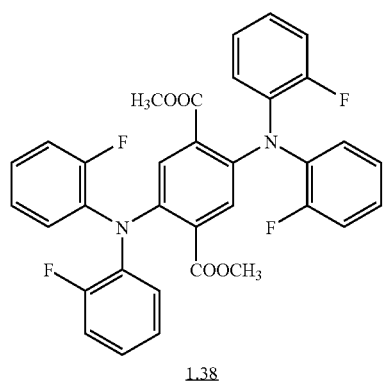<br>1.38 | —CH₃ | 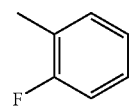 | 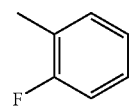 |
| 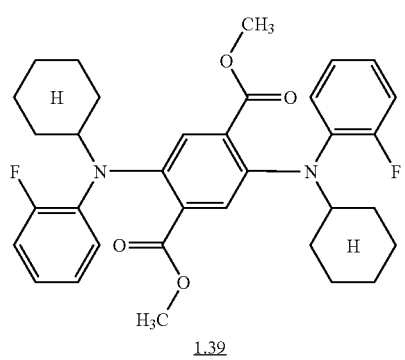<br>1.39 | —CH₃ |  | 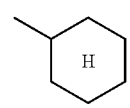 |
| 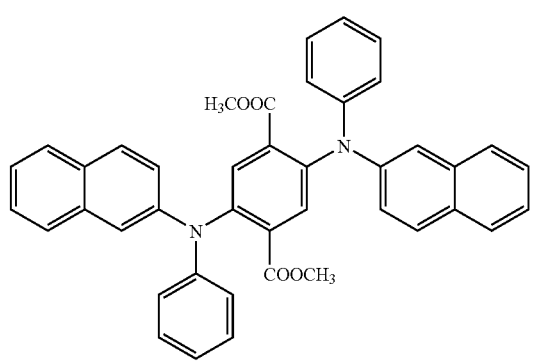<br>1.40 | —CH₃ | 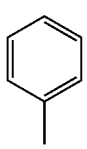 | 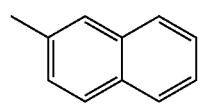 |

TABLE 1-continued
2,5-diaminoterephthalic acid derivatives
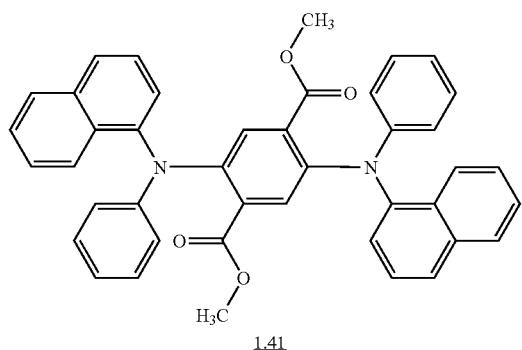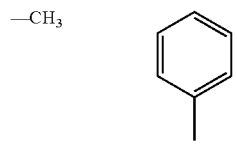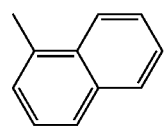
1.41    —CH₃
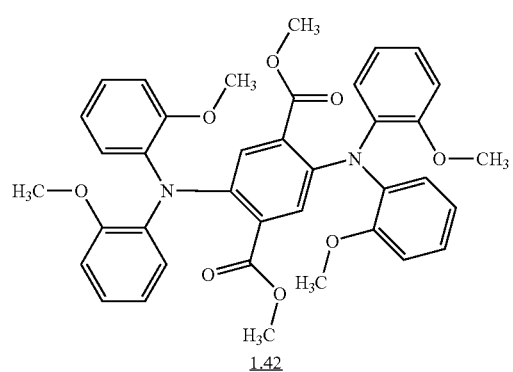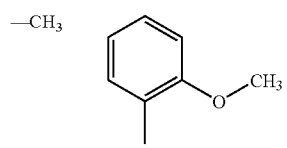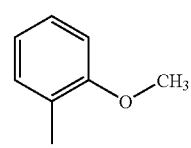
1.42    —CH₃
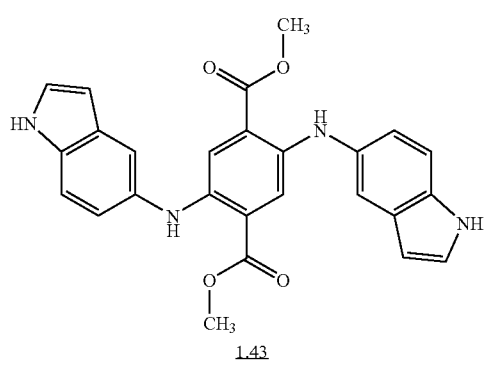    —CH₃    H    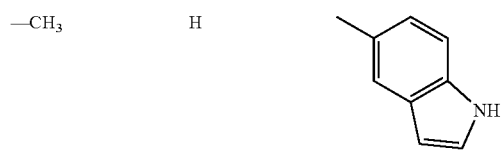
1.43
1.44    —CH₃    —CH₃    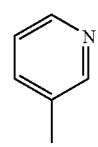
1.45    —CH₃    —CH₃    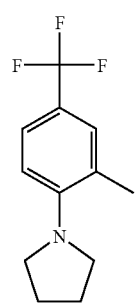

TABLE 1-continued
| 2,5-diaminoterephthalic acid derivatives | | | |
|---|---|---|---|
| 1.46 | —CH₃ | —CH₃ | 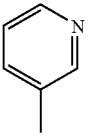 |
| 1.47 | —CH₃ | —CH₃ | 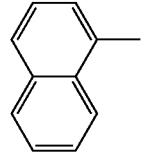 |
| 1.48 | —CH₃ | —CH₃ | 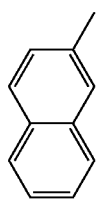 |
| 1.49 | —CH₃ | —CH₃ | 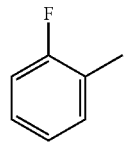 |
| 1.50 | —CH₃ | —CF₃ | 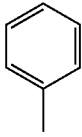 |
| 1.51 | —CH₃ | —CF₃ | 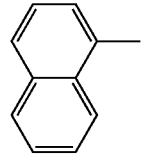 |
| 1.52 | —CH₃ | —CF₃ | 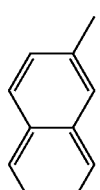 |
| 1.53 | —CH₃ | —CF₃ | 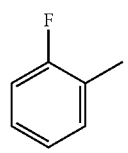 |
| 1.54 | —CH₃ | —CF₃ | 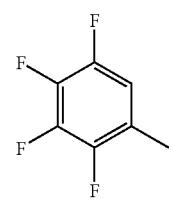 |

TABLE 1-continued
2,5-diaminoterephthalic acid derivatives
| 1.55 | —CH₃ | —CF₃ | 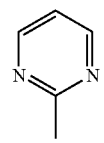 |
| 1.56 | —CH₃ | 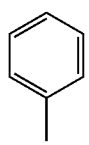 | 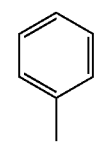 |
| 1.57 | —CH₃ | 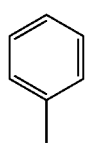 | 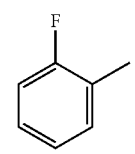 |
| 1.58 | —CH₃ | 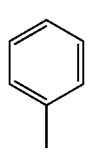 | 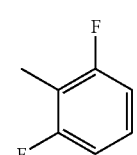 |
| 1.59 | —CH₃ | 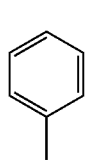 | 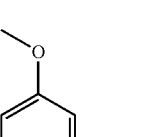 |
| 1.60 | —CH₃ | 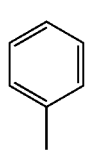 | 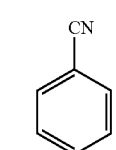 |
| 1.61 | —CH₃ | 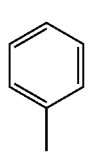 | 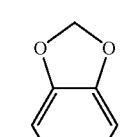 |
| 1.62 | —CH₃ | 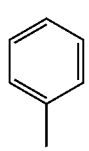 | 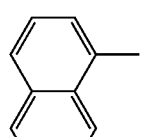 |

TABLE 1-continued
2,5-diaminoterephthalic acid derivatives
| Substance | | | | |
|---|---|---|---|---|
| 1.63 | —CH₃ |  | |  |
| 1.64 | —CH₃ |  | |  |
| 1.65 | —CH₃ | —CH₃ | | 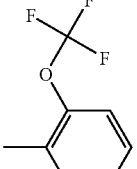 |
| 1.67 | —CH₃ | 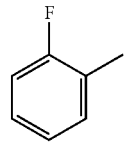 | | 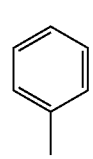 |
| 1.68 | —CH₃ | | | |
| Substance | X¹ | X² | R³ | R¹ |
|---|---|---|---|---|
| 1.69 | O | O | | —CH₃ |
| 1.70 | | | | —CH₃ |
| 1.71 | O | N | | |

TABLE 1-continued 2,5-diaminoterephthalic acid derivatives

| 1.72 | O | N | phenyl | tetrahydropyranyl |
| 1.73 | O | O | phenyl | —CH₃ |
| 1.74 | O | O | phenyl | —CH₃ |
| 1.75 | O | O | phenyl | —CH₃ |

17.0

| | | | | |
|---|---|---|---|---|
| | | | benzo-diazine | phenyl | —CH₃ |
| | | | benzo-diazine | phenyl | —CH₃ |
| 17.3 | | | benzo(N,O) | phenyl | — |

TABLE 1-continued

2,5-diaminoterephthalic acid derivatives

| Substance | R² | R⁴ | X⁴ | X³ | R⁸ |
|---|---|---|---|---|---|
| 1.69 | 2-fluorophenyl | H | O | O | H |
| 1.70 | 2-fluorophenyl | H | O | O | H |

17.4 — (structure with N=, S-CH₃ group and phenyl)

5.0 / 5.1 — (bicyclic structure with R¹–R⁸, X¹–X⁴ substituents; 1,2-diiminobenzene and two tolyl groups)

11.0 / 11.1 — (structure with R¹–R⁸, X¹–X⁴; X⁴=O, X³=O, phenyl, —CH₃)

TABLE 1-continued 2,5-diaminoterephthalic acid derivatives

| | | | | | |
|---|---|---|---|---|---|
| 1.71 | | H | H | N | O | H |
| 1.72 | phenyl | H | N | O | H |
| 1.73 | —CH₃ | phenyl | O | O | phenyl |
| 1.74 | phenyl | phenyl | O | O | phenyl |
| 1.75 | 2-fluorophenyl | phenyl | O | O | phenyl |

[Structure: 2,5-diaminoterephthalic acid derivative with substituents X¹, X², R¹, R², R³, R⁴, R⁵, R⁶, R⁷, R⁸, X³, X⁴]

17.0

| 17.0 | —CH₃ | H | (2-aminophenyl imine) | H |
| | —CH₃ | H | (2-aminophenyl imine) | H |
| 17.3 | —CH₃ | H | (2-methoxyphenyl imine) | H |

TABLE 1-continued

2,5-diaminoterephthalic acid derivatives

| | | | | |
|---|---|---|---|---|
| 17.4 | —CH₃ | H | [2-(methylthio)phenyl-N=] | H |

| 5.0 | | | | |
|---|---|---|---|---|
| 5.1 | —CH₃ | H | O | O | H |

| 11.0 | | | | |
|---|---|---|---|---|
| 11.1 | —CH₃ | H | [2-(phenyl-N=)phenyl-N=] | [phenyl] |

| Substance | R⁵ | R⁶ | R⁷ |
|---|---|---|---|
| 1.69 | —CH₃ | [2-fluorophenyl] | [2-(trifluoromethoxy)phenyl] |
| 1.70 | —CH₃ | [2-fluorophenyl] | [2-fluorophenyl] |

TABLE 1-continued
2,5-diaminoterephthalic acid derivatives
| | | | |
|---|---|---|---|
| 1.71 | 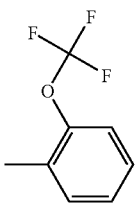 | H | 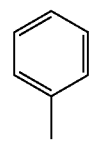 |
| 1.72 | 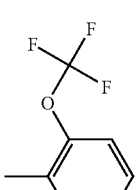 | 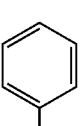 | 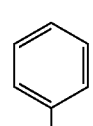 |
| 1.73 | —CH₃ | —CH₃ | 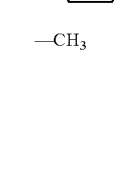 |
| 1.74 | —CH₃ | 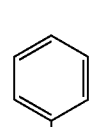 |  |
| 1.75 | —CH₃ | 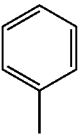 | 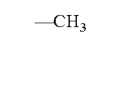 |
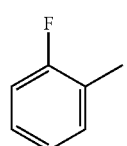
17.0
| | | |
|---|---|---|
| —CH₃ | —CH₃ | 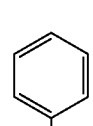 |
| —CH₃ | —CH₃ |  |

TABLE 1-continued
2,5-diaminoterephthalic acid derivatives
| | | | |
|---|---|---|---|
| 17.3 | — | —CH$_3$ | 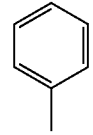 |
| 17.4 | — | —CH$_3$ | 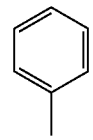 |
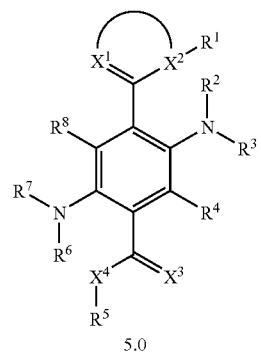
| | | | |
|---|---|---|---|
| 5.0 | | | |
| 5.1 | —CH$_3$ | —CH$_3$ | 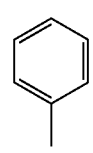 |
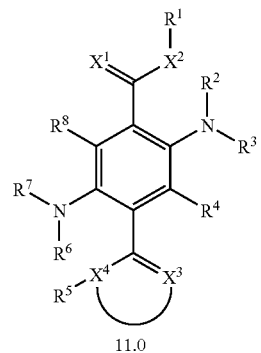
| | | | |
|---|---|---|---|
| 11.0 | | | |
| 11.1 | —CH$_3$ | —CH$_3$ | 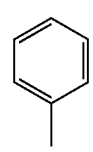 |

US 7,141,312 B2
115                                              116
TABLE 1-continued
2,5-diaminoterephthalic acid derivatives
| Substance | X$^1$ | X$^2$ | R$^3$ | R$^2$ | R$^1$ |
|---|---|---|---|---|---|
| 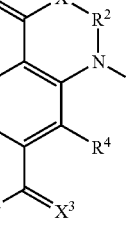 19.0 | | | | | |
| 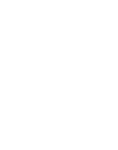 19.1 | O | O | 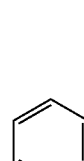 | —CH$_2$— | — |
| 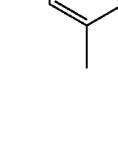 19.2 | O | O | 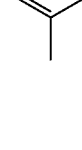 | —CH$_2$— | — |
| 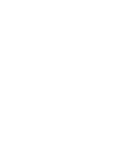 19.3 | O | O | 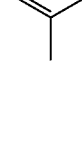 | —CH$_2$— | — |
| 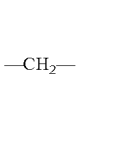 19.4 | O | O | 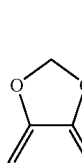 | —CH$_2$— | — |

TABLE 1-continued 2,5-diaminoterephthalic acid derivatives

| Structure | | | | |
|---|---|---|---|---|
| 19.5 | O | O | 4-(dimethylamino)phenyl | —CH₂— | — |
| 19.6 | O | O | 3,4,5-trimethoxyphenyl | —CH₂— | — |
| 19.7 | O | O | 2,4,6-trimethylphenyl (mesityl) | —CH₂— | — |
| 19.8 | O | O | 4-fluorophenyl | —CH₂— | — |
| 19.9 | O | O | 4-cyanophenyl | —CH₂— | — |
| 19.10 | O | O | 4-carboxyphenyl | —CH₂— | — |

TABLE 1-continued
2,5-diaminoterephthalic acid derivatives
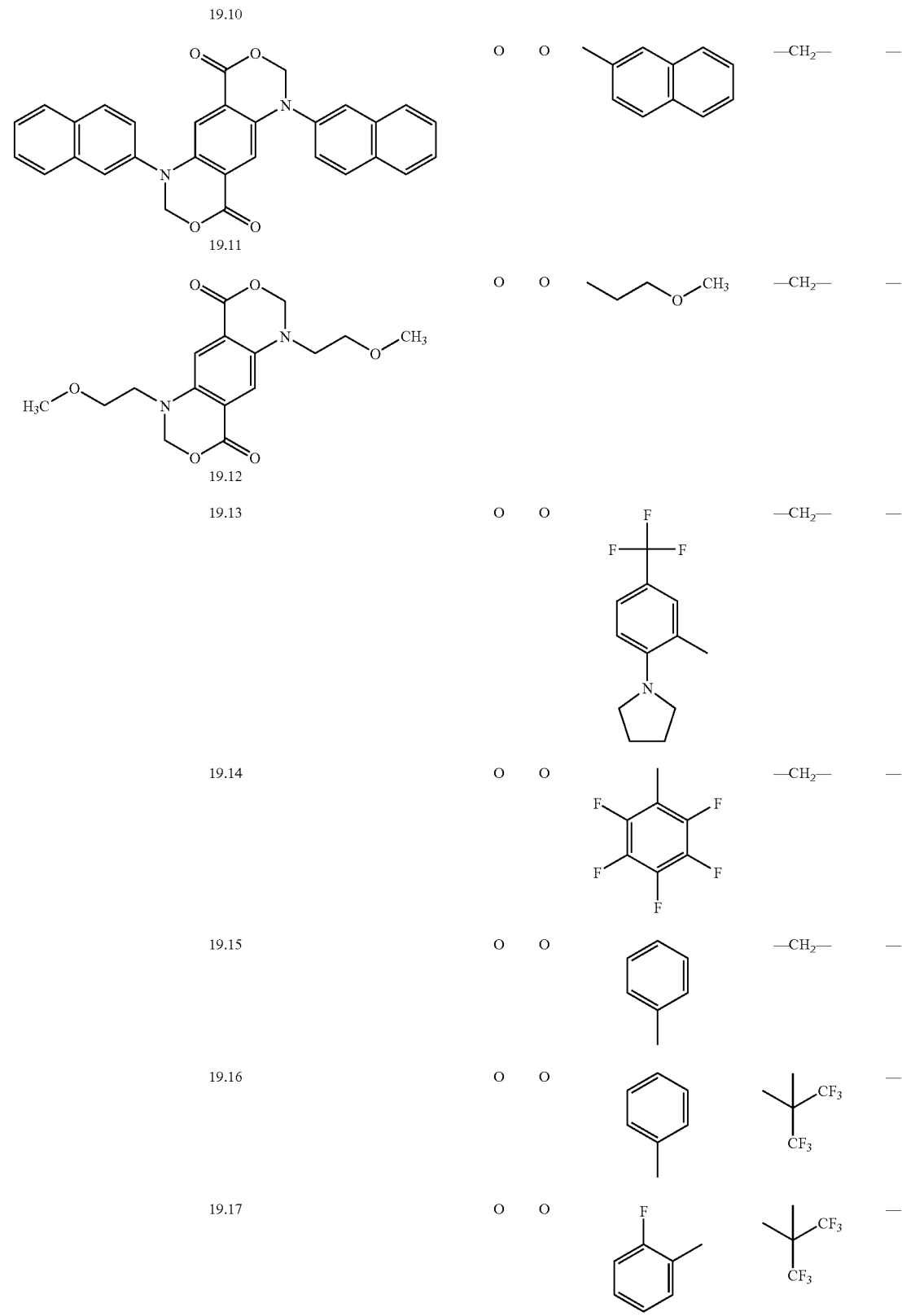

TABLE 1-continued
2,5-diaminoterephthalic acid derivatives
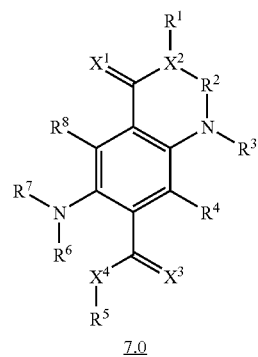
7.0
| 7.1 | O | O | 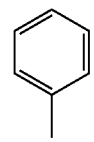 | —CH$_2$— |
| 7.2 | O | O | 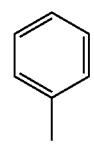 | —CH$_2$— |
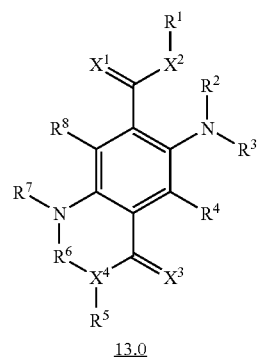
13.0
| 13.1 | O | O | 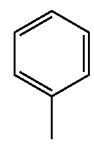 | | —CH$_3$ |
| 13.2 | O | O | 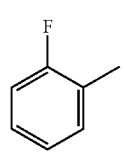 | | —CH$_3$ |

TABLE 1-continued 2,5-diaminoterephthalic acid derivatives

| Substance | R⁴ | X⁴ | X³ | R⁸ | R⁶ | R⁵ | R⁷ |
|---|---|---|---|---|---|---|---|
| 19.0 (general structure) | | | | | | | |
| 19.1 | H | O | O | H | —CH₂— | — | phenyl |
| 19.2 | H | O | O | H | —CH₂— | — | 1,3-benzodioxol-5-yl |
| 19.3 | H | O | O | H | —CH₂— | — | 4-methoxyphenyl |
| 19.4 | H | O | O | H | —CH₂— | — | 2,4-dimethoxyphenyl |

TABLE 1-continued
2,5-diaminoterephthalic acid derivatives
| | | | | | | | |
|---|---|---|---|---|---|---|---|
| 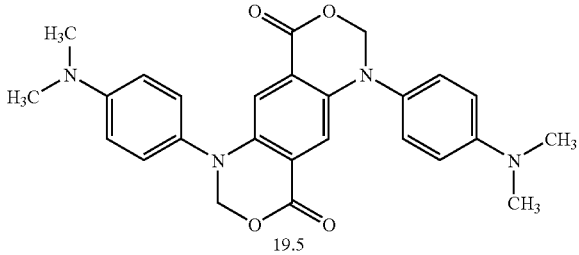 19.5 | H | O | O | H | —CH$_2$— | — | 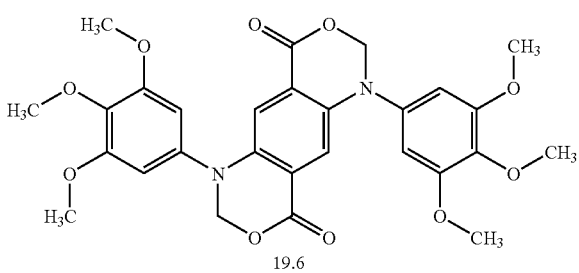 |
| 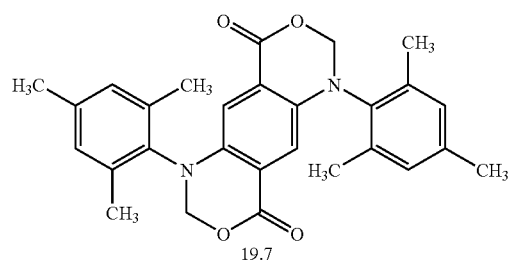 19.6 | H | O | O | H | —CH$_2$— | — | 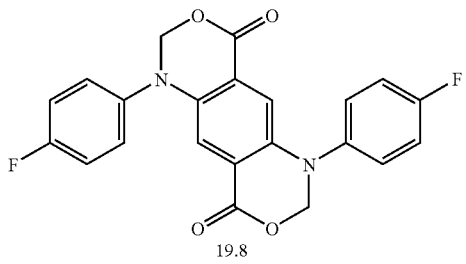 |
| 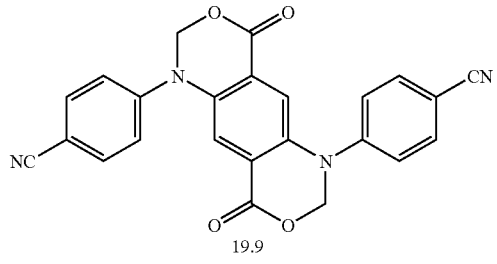 19.7 | H | O | O | H | —CH$_2$— | — | 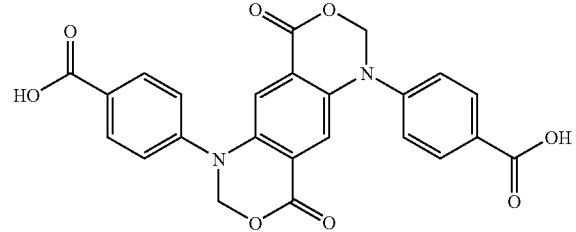 |
| 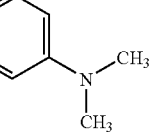 19.8 | H | O | O | H | —CH$_2$— | — | 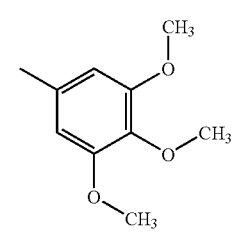 |
| 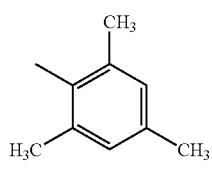 19.9 | H | O | O | H | —CH$_2$— | — | 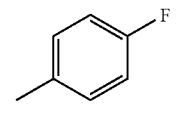 |
| 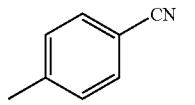 | H | O | O | H | —CH$_2$— | — | 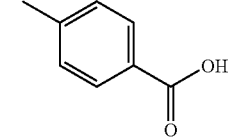 |

TABLE 1-continued 2,5-diaminoterephthalic acid derivatives

| | | | | | | | |
|---|---|---|---|---|---|---|---|
| 19.10 | | | | | | | |
| 19.11 | [structure: bis-naphthyl dioxazine fused system] | H | O O | H | —CH₂— | — | [2-naphthyl] |
| 19.12 | [structure: bis(methoxyethyl) dioxazine fused system] | H | O O | H | —CH₂— | — | —CH₂CH₂—O—CH₃ |
| 19.13 | | H | O O | H | —CH₂— | — | [3-methyl-4-(pyrrolidin-1-yl)-benzene with CF₃] |
| 19.14 | | H | O O | H | —CH₂— | — | [methyl-pentafluorophenyl] |
| 19.15 | | H | O O | H | —CF₂— | — | [tolyl] |
| 19.16 | | H | O O | H | —C(CF₃)₂— | — | [tolyl] |
| 19.17 | | H | O O | H | —C(CF₃)₂— | — | [2-fluoro-tolyl] |

TABLE 1-continued
2,5-diaminoterephthalic acid derivatives
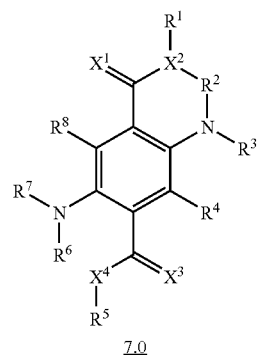
7.0
| 7.1 | H | O | O | H | —CH₃ | —CH₃ | 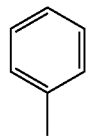 |
| 7.2 | H | N | O | H |  | —CH₃ | 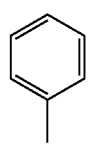 |
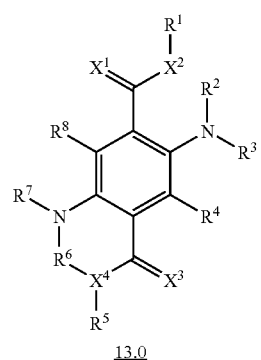
13.0
| 13.1 | H | N | O | H | —CH₂— | 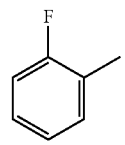 |
| 13.2 | H | N | O | H | —CH₂— | 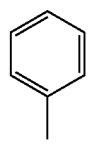 |

TABLE 1-continued
2,5-diaminoterephthalic acid derivatives
| Substance | X¹ | R¹ | X² | R² | R³ | R⁴ | R⁵ | X³ | X⁴ | R⁶ | R⁷ | R⁸ |
|---|---|---|---|---|---|---|---|---|---|---|---|---|
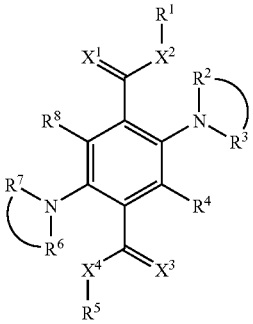
20.0
| 20.1 | O | —CH₃ | O | 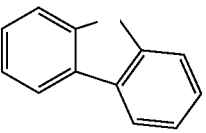 | | H | —CH₃ | O | O | 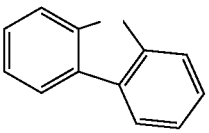 | | H |
| 20.2 | O | —CH₃ | O | 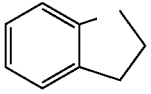 | | H | —CH₃ | O | O | 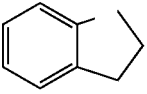 | | H |
| 20.3 | O | —CH₃ | O | 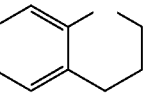 | | H | —CH₃ | O | O | 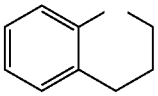 | | H |
| 20.4 | O | —CH₃ | O | 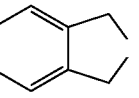 | | H | —CH₃ | O | O | 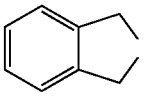 | | H |
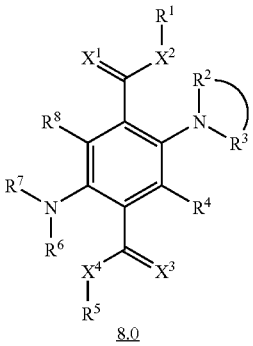
8.0
| 8.1 | O | —CH₃ | O | 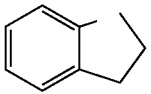 | | H | —CH₃ | O | O | —CH₃ |  | H |
| 8.2 | O | —CH₃ | O | 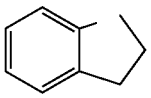 | | H | —CH₃ | O | O |  |  | H |

TABLE 1-continued
2,5-diaminoterephthalic acid derivatives
| 8.3 | O | —CH₃ | O | 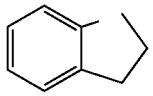 | 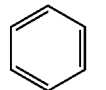 | —CH₃ | O | O |  |  | H |
| Substance | X¹ | X² | R³ | R² | R¹ | R⁴ | X⁴ | X³ | R⁸ | R⁶ | R⁵ | R⁷ |
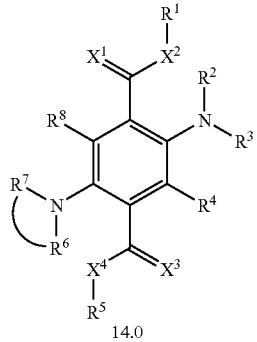
14.0
| 14.1 | O | —CH₃ | O | —CH₃ |  |  | —CH₃ | O | O | 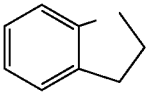 | H |
| 14.2 | O | —CH₃ | O |  |  |  | —CH₃ | O | O | 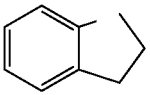 | H |
| Substance | R¹ | X² | X¹ | R⁴ | R³ | R² | R⁵ | X⁴ | X³ | R⁸ | R⁷ | R⁶ |
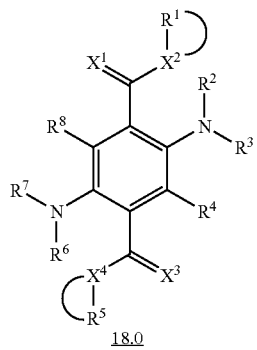
18.0
| 18.1 | 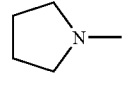 | O | H |  | —CH₃ | 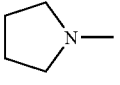 | O | H |  | —CH₃ |
| 18.2 | 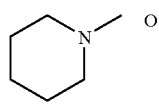 | O | H |  | —CH₃ | 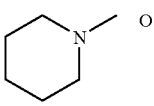 | O | H |  | —CH₃ |

TABLE 1-continued 2,5-diaminoterephthalic acid derivatives

| | | | | | | | | | | |
|---|---|---|---|---|---|---|---|---|---|---|
| 18.3 | morpholine-N-CH₂- | O | H | 4-methylphenyl | —CH₃ | | | morpholine-N-CH₂- | O | H | 4-methylphenyl | —CH₃ |
| 18.4 | 1-methylpyrrolidin-2-yl-CH₂CH₂OH | O | H | 4-methylphenyl | —CH₃ | | | 1-methylpyrrolidin-2-yl-CH₂CH₂OH | O | H | 4-methylphenyl | —CH₃ |

| 6.0 | | | | | | | | | |
|---|---|---|---|---|---|---|---|---|---|
| 6.1 | morpholine-N-CH₂- | O | H | 4-methylphenyl | —CH₃ | —CH₃ | O | O | H | 4-methylphenyl | —CH₃ |
| 6.2 | morpholine-N-CH₂- | O | H | 4-methylphenyl | 4-methylphenyl | —CH₃ | O | O | H | 4-methylphenyl | 4-methylphenyl |

| 12.0 | | | | | | | | | |
|---|---|---|---|---|---|---|---|---|---|
| 12.1 | —CH₃ | O | O | H | phenyl | —CH₃ | morpholine-N-CH₂- | O | H | phenyl | H |

TABLE 1-continued
2,5-diaminoterephthalic acid derivatives
| 12.2 | —CH₃ | O | O | H | 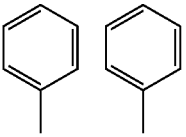 | 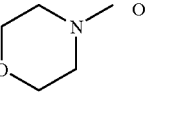 | 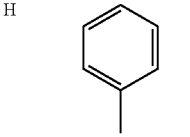 | O | H | 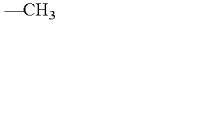 | —CH₃ |
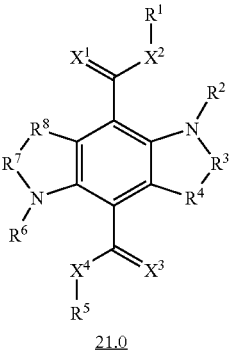
21.0
| 21.1 | —CH₃ | O | O | 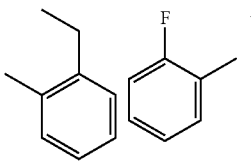 | 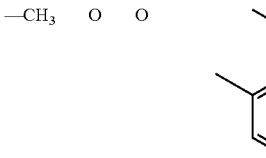 | —CH₃ | O | O | 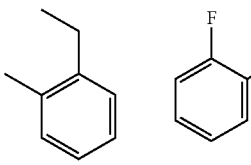 |  |
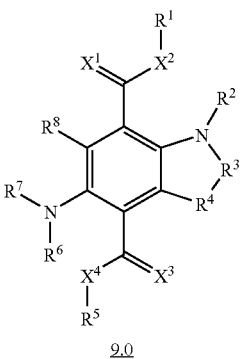
9.0
| 9.1 | —CH₃ | O | O | 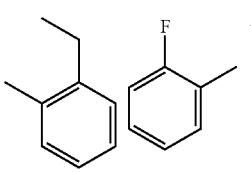 | 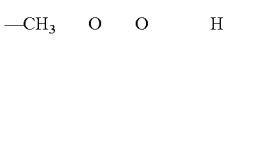 | —CH₃ | O | O | H | 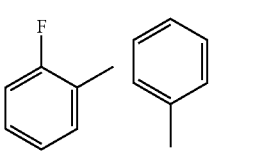 |  |
| 9.2 | —CH₃ | O | O | 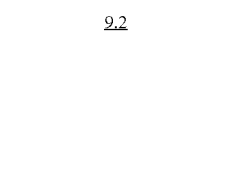 | 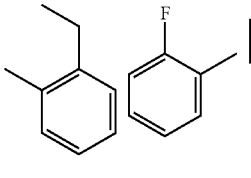 | 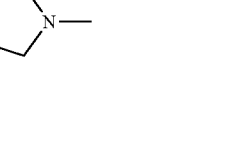 | O | H | 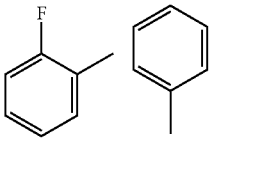 |  |

TABLE 1-continued
2,5-diaminoterephthalic acid derivatives
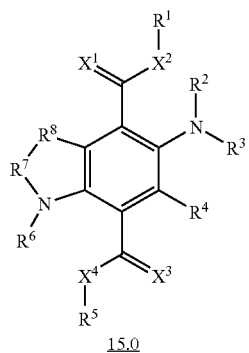
15.0
15.1 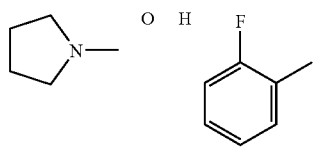 —CH₃ O O 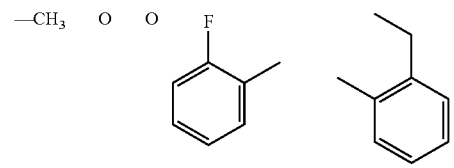
| Substance | X² | R² | R³ | R⁴ | X³ | R⁵ | R⁶ | X⁴ | R⁷ | R⁸ | X¹ | R¹ |
|---|---|---|---|---|---|---|---|---|---|---|---|---|
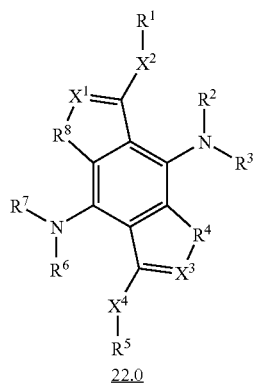
22.0
22.1 O —CH₃ 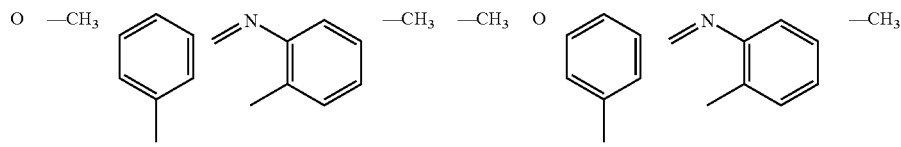 —CH₃ —CH₃ O —CH₃
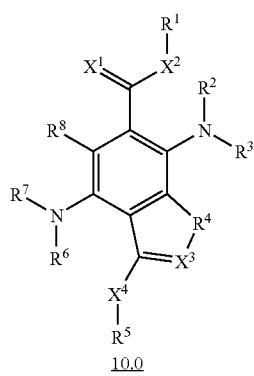
10.0

TABLE 1-continued
2,5-diaminoterephthalic acid derivatives
| 10.1 | O | —CH₃ | 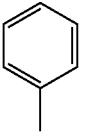 | 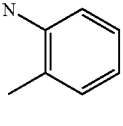 | —CH₃ | —CH₃ | O | 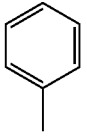 | H | O | —CH₃ |
| --- | --- | --- | --- | --- | --- | --- | --- | --- | --- | --- | --- |
| 10.2 | O | 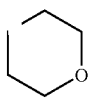 | 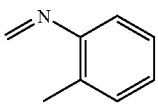 | | —CH₃ | —CH₃ | O | | H | O | —CH₃ |
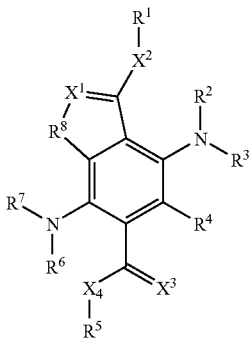
16.0
| 16.1 | O | 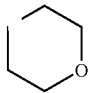 | H | O | —CH₃ | —CH₃ | O | 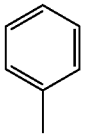 | 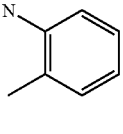 | —CH₃ |
| --- | --- | --- | --- | --- | --- | --- | --- | --- | --- | --- |
TABLE 2
2,5-diamino-3,6-dihydroterephthalic acid derivatives
| Substance | X¹ | X² | R³ | R¹ |
| --- | --- | --- | --- | --- |
2.0
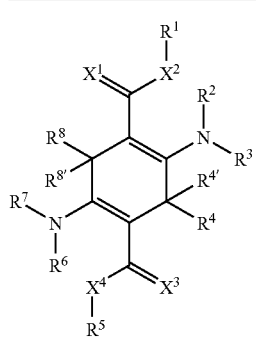

TABLE 2-continued

| | | | | |
|---|---|---|---|---|
| [structure: dimethyl 2,5-bis((4-cyanophenyl)amino)cyclohexa-1,4-diene-1,4-dicarboxylate] | 2.1 | O O | [4-cyanophenyl/tolyl] | —CH₃ |
| [structure: dimethyl 2,5-bis((2-fluorophenyl)(methyl)amino)cyclohexa-1,4-diene-1,4-dicarboxylate] | 2.2 | O O | [2-fluorotolyl] | —CH₃ |
| [structure: dimethyl 2,5-bis((2-fluorophenyl)amino)cyclohexa-1,4-diene-1,4-dicarboxylate] | 2.3 | O O | [2-fluorotolyl] | —CH₃ |
| [structure: dimethyl 2,5-bis([1,1'-biphenyl]-4-ylamino)cyclohexa-1,4-diene-1,4-dicarboxylate] | 2.4 | O O | [4-biphenylyl-methyl] | —CH₃ |

TABLE 2-continued
| Structure | # | | | Substituent | R |
|---|---|---|---|---|---|
| 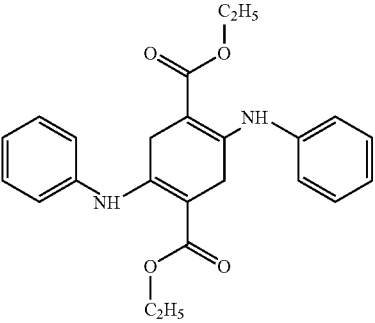 | 2.5 | O | O | 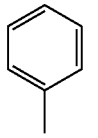 | —C$_2$H$_5$ |
| 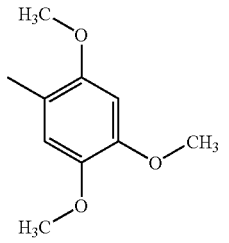 | 2.6 | O | O | 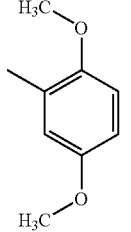 | —CH$_3$ |
| 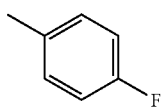 | 2.7 | O | O | 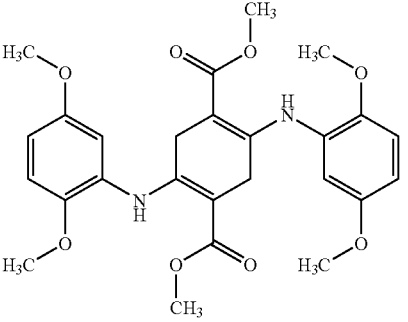 | —CH$_3$ |
| 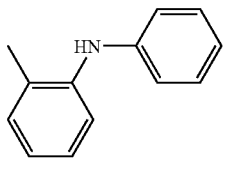 | 2.8 | O | O | | —CH$_3$ |
| 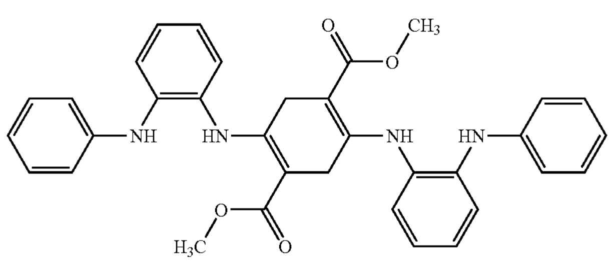 | 2.9 | O | O | | —CH$_3$ |

TABLE 2-continued
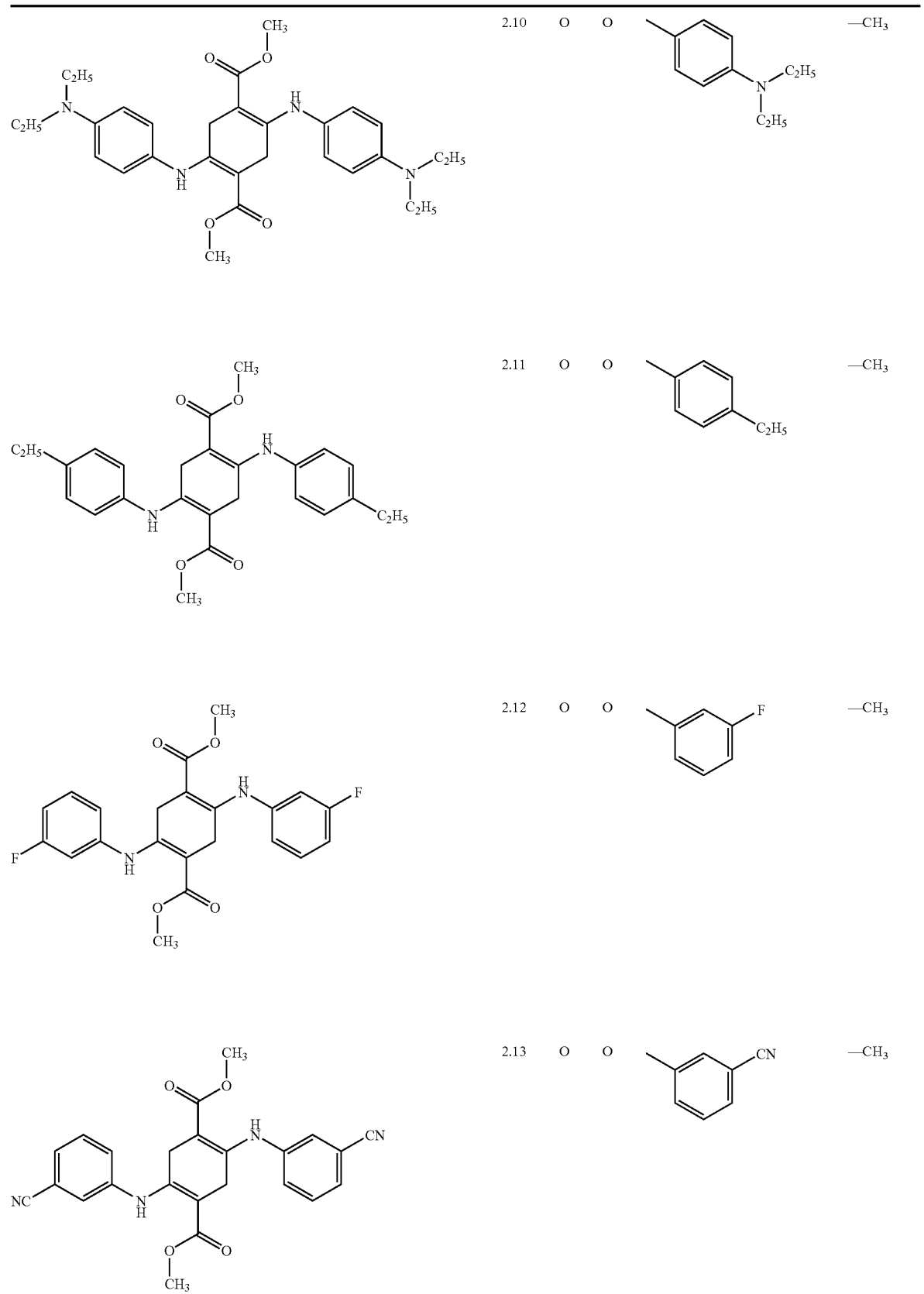

TABLE 2-continued
| | | | | | |
|---|---|---|---|---|---|
| 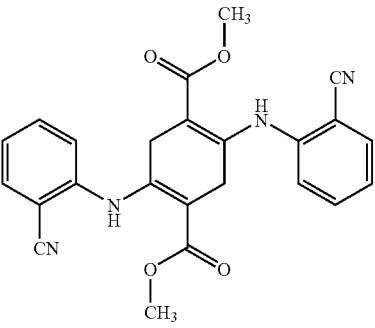 | 2.14 | O | O | 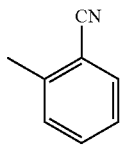 | —CH₃ |
| 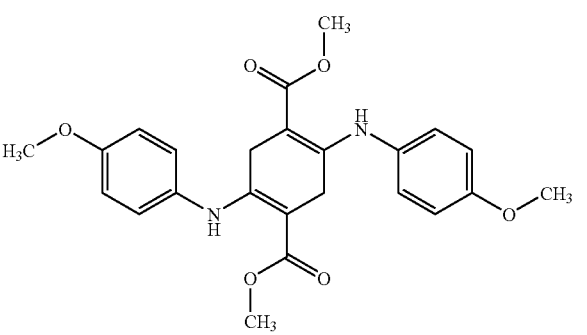 | 2.15 | O | O | 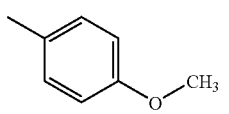 | —CH₃ |
| 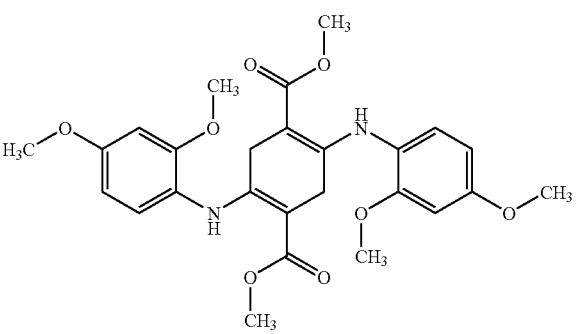 | 2.16 | O | O | 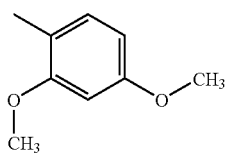 | —CH₃ |
| 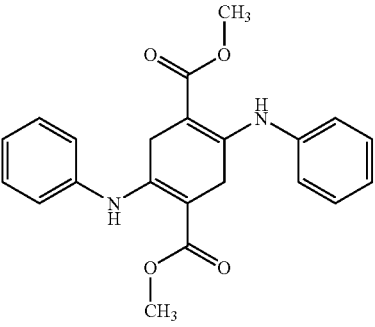 | 2.17 | O | O | 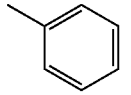 | —CH₃ |

| | | | | |
|---|---|---|---|---|
| 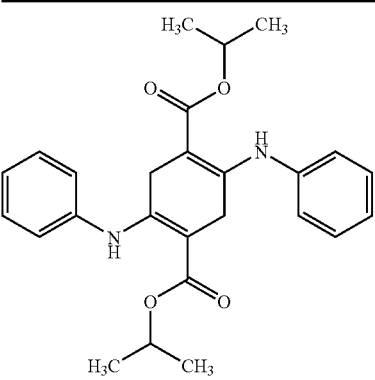 | 2.18 | O | O | 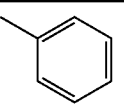 | —CH₃ |
| 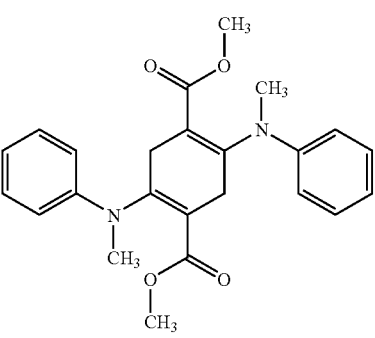 | 2.19 | O | O | 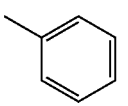 | —CH₃ |
| 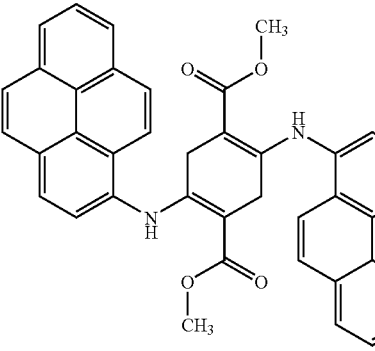 | 2.20 | O | O | 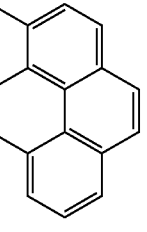 | —CH₃ |
| 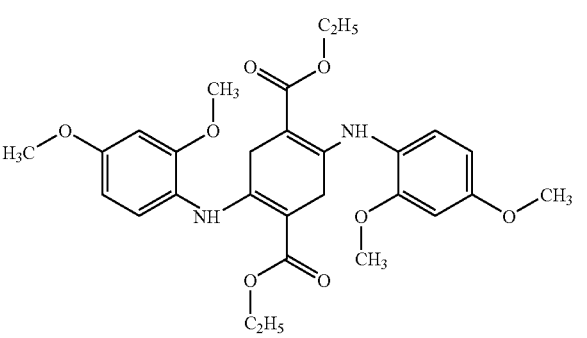 | 2.21 | O | O | 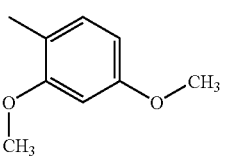 | —CH₃ |

TABLE 2-continued

| | | | | |
|---|---|---|---|---|
| (structure) | 2.22 | O | O | (4-dimethylaminophenyl, methyl) | —CH₃ |
| (structure) | 2.24 | O | O | (methylenedioxyphenyl) | —CH₃ |
| (structure) | 2.25 | O | O | —C₄H₉ | —CH₃ |
| (structure) | 2.26 | O | O | (CH₂CH₂OCH₃) | —CH₃ |
| (structure) | 2.27 | O | O | (3,4,5-trimethoxyphenyl) | —CH₃ |

TABLE 2-continued

| Structure | # | | | Ar | R |
|---|---|---|---|---|---|
| (structure) | 2.28 | O | O | 2,4,6-trimethylphenyl / 2,3,5-trimethylphenyl | —CH₃ |
| (structure) | 2.29 | O | O | 2,5-dimethoxy-methylphenyl | —CH₃ |
| (structure) | 2.30 | O | O | cyclohexyl | —CH₃ |
| (structure) | 2.31 | O | O | 3-fluorophenyl | —CH₃ |
| (structure) | 2.32 | O | O | 2,4-dimethoxyphenyl | —CH₃ |

TABLE 2-continued

| Structure | # | | | Ar | R |
|---|---|---|---|---|---|
| (structure) | 2.33 | O | O | 4-fluorophenyl | —CH₃ |
| (structure) | 2.34 | O | O | phenyl | —CH₃ |
| (structure) | 2.35 | O | O | 2,6-difluorophenyl | —CH₃ |
| (structure) | 2.36 | O | O | 2,6-difluorophenyl | —CH₃ |
| (structure) | 2.37 | O | O | 2,4-difluorophenyl | —CH₃ |
| (structure) | 2.38 | O | O | 2-fluorophenyl | —CH₃ |

TABLE 2-continued
| | 2.39 | O | O | 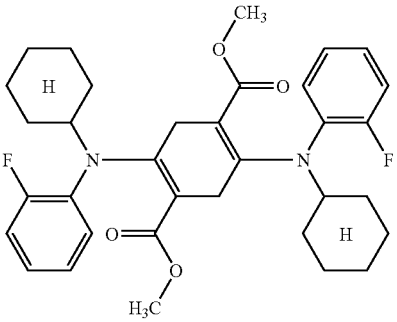 | —CH$_3$ |
|---|---|---|---|---|---|
| 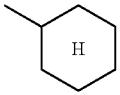 | | | | | |
| 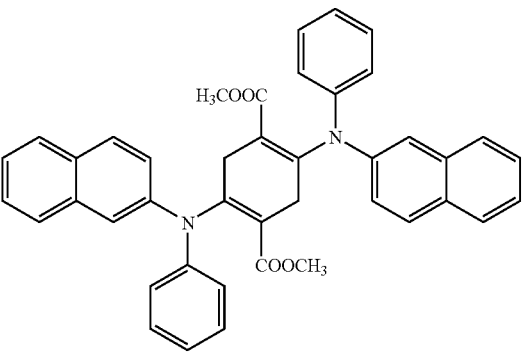 | 2.40 | O | O | 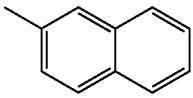 | —CH$_3$ |
| 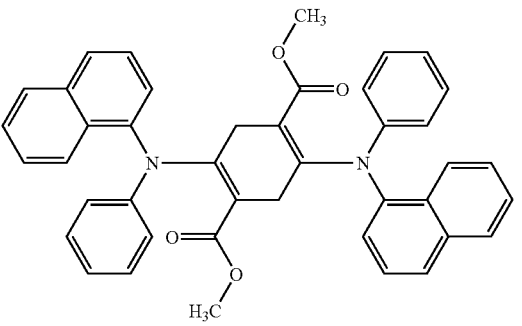 | 2.41 | O | O | 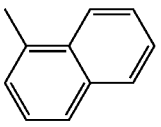 | —CH$_3$ |
| 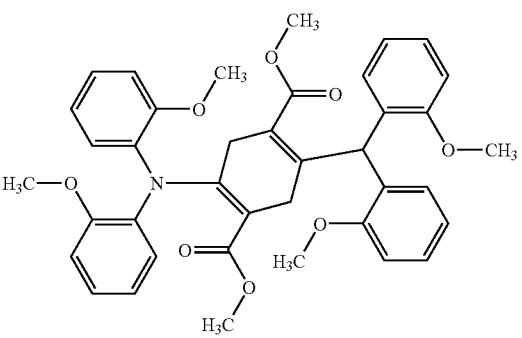 | 2.42 | O | O | 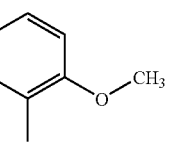 | —CH$_3$ |

TABLE 2-continued
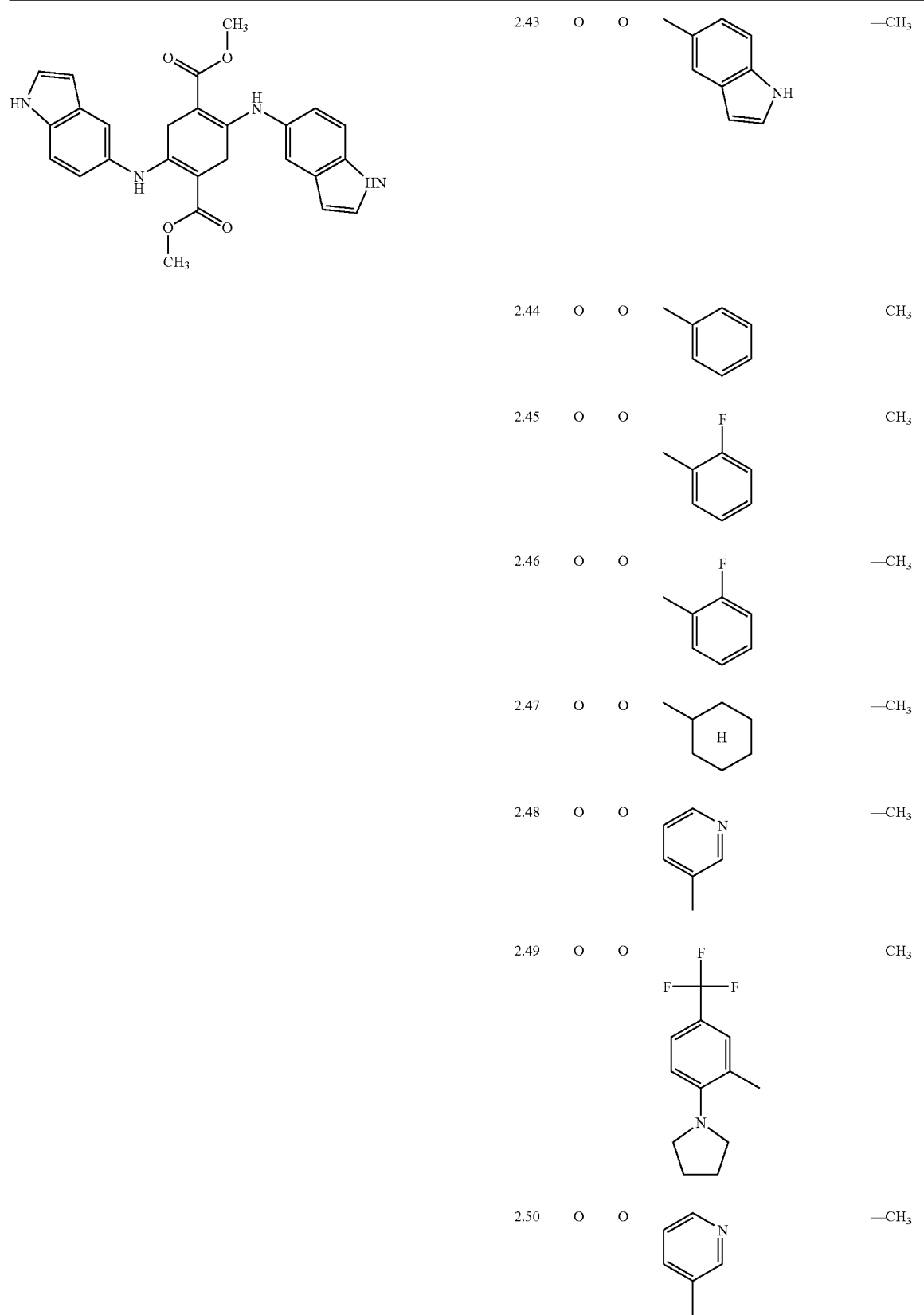
| | | | | |
|---|---|---|---|---|
| 2.43 | O | O | 5-indolyl (methyl-substituted) | —CH₃ |
| 2.44 | O | O | 3-methylphenyl | —CH₃ |
| 2.45 | O | O | 2-fluoro-6-methylphenyl | —CH₃ |
| 2.46 | O | O | 2-fluoro-6-methylphenyl | —CH₃ |
| 2.47 | O | O | methylcyclohexyl | —CH₃ |
| 2.48 | O | O | 3-methylpyridyl | —CH₃ |
| 2.49 | O | O | 3-methyl-4-pyrrolidinyl-(trifluoromethyl)phenyl | —CH₃ |
| 2.50 | O | O | 3-methylpyridyl | —CH₃ |

TABLE 2-continued
| | | | | |
|---|---|---|---|---|
| 2.51 | O | O | 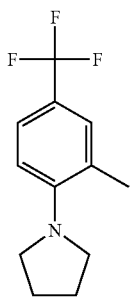 | —CH₃ |
| 2.52 | O | O | 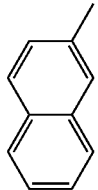 | —CH₃ |
| 2.53 | O | O | 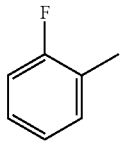 | —CH₃ |
| 2.54 | O | O | 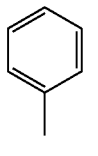 | —CH₃ |
| 2.55 | O | O | 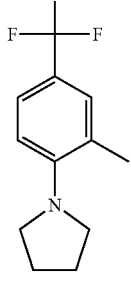 | —CH₃ |
| 2.56 | O | O | 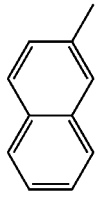 | —CH₃ |
| 2.57 | O | O | 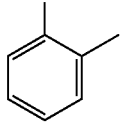 | —CH₃ |

TABLE 2-continued
| | | | | |
|---|---|---|---|---|
| 2.58 | O | O | 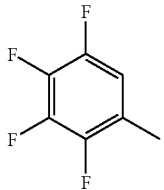 | —CH₃ |
| 2.59 | O | O | 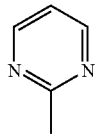 | —CH₃ |
| 2.60 | O | O | 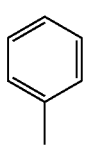 | —CH₃ |
| 2.61 | O | O | 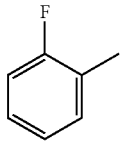 | —CH₃ |
| 2.62 | O | O | 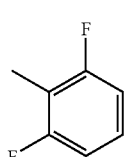 | —CH₃ |
| 2.63 | O | O | 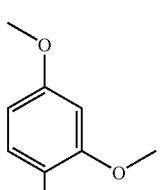 | —CH₃ |
| 2.64 | O | O | 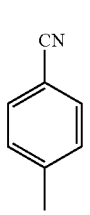 | —CH₃ |
| 2.65 | O | O | 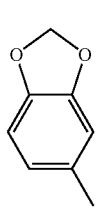 | —CH₃ |

TABLE 2-continued

| | | | | |
|---|---|---|---|---|
| 2.66 | O | O | 4-(trifluoromethyl)-2-methyl-1-(pyrrolidin-1-yl)phenyl | —CH₃ |
| 2.67 | O | O | 7-methylnaphthalen-2-yl | —CH₃ |
| 2.68 | O | O | 2,3,4,5-tetrafluoro-6-methylphenyl | —CH₃ |
| 2.69 | O | O | pentafluoromethylphenyl | —CH₃ |
| 2.70 | O | O | pentafluoromethylphenyl | —CH₃ |
| 2.71 | O | O | 8-methyl-julolidinyl | —CH₃ |
| 2.72 | O | O | 2-methyl-(trifluoromethoxy)phenyl | —CH₃ |

TABLE 2-continued
| | | | | | |
|---|---|---|---|---|---|
| 2.73 | | |  | | —CH₃ |
| 2.74 | O | N |  | |  |
| 2.75 | O | N |  | |  |
| 2.76 | O | O |  | | —CH₃ |
| 2.77 | O | O |  | | —CH₃ |
| 2.79 | O | O |  | | —CH₃ |
| Substance | | R² | R⁴' | R⁴' | X⁴ | X³ |
|---|---|---|---|---|---|---|
|  | 2.0 | | | | | |
| 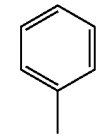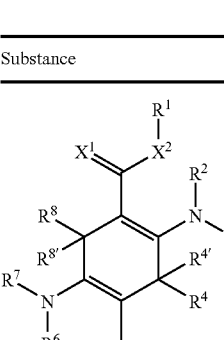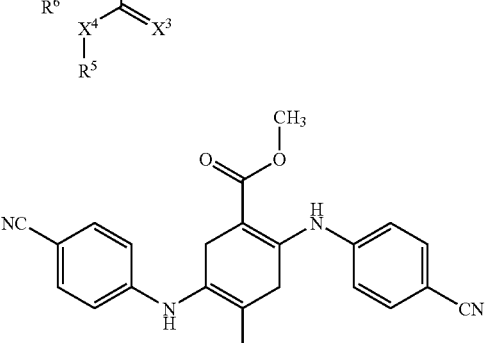 | 2.1 | H | H | H | O | O |

TABLE 2-continued

| Structure | # | R | R' | R'' | X | Y |
|---|---|---|---|---|---|---|
| (structure 2.2) | 2.2 | —CH₃ | H | H | O | O |
| (structure 2.3) | 2.3 | H | H | H | O | O |
| (structure 2.4) | 2.4 | H | H | H | O | O |
| (structure 2.5) | 2.5 | H | H | H | O | O |

TABLE 2-continued

| Structure | # | | | | | |
|---|---|---|---|---|---|---|
| (structure) | 2.6 | H | H | H | O | O |
| (structure) | 2.7 | H | H | H | O | O |
| (structure) | 2.8 | H | H | H | O | O |
| (structure) | 2.9 | H | H | H | O | O |
| (structure) | 2.10 | H | H | H | O | O |

TABLE 2-continued
| Structure | # | | | | | |
|---|---|---|---|---|---|---|
| 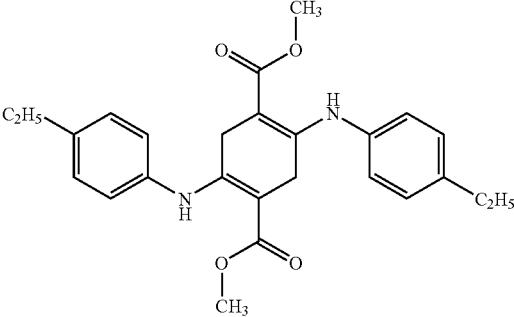 | 2.11 | H | H | H | O | O |
| 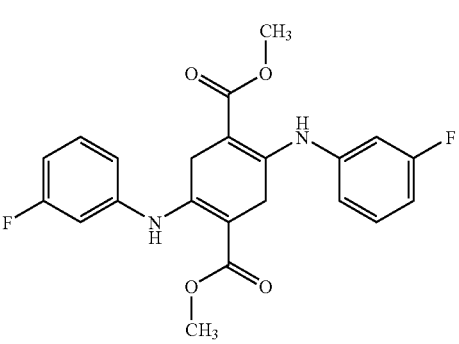 | 2.12 | H | H | H | O | O |
| 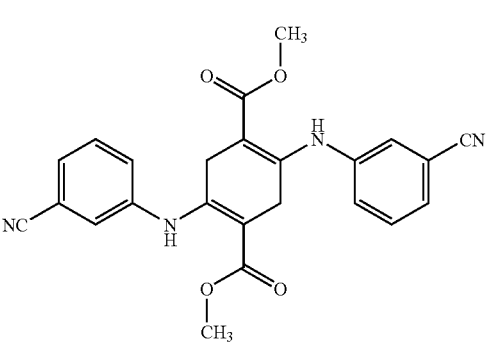 | 2.13 | H | H | H | O | O |
| 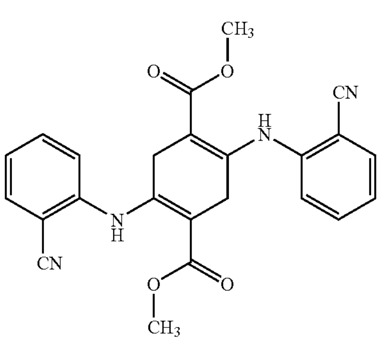 | 2.14 | H | H | H | O | O |

TABLE 2-continued
| | | | | | |
|---|---|---|---|---|---|
| 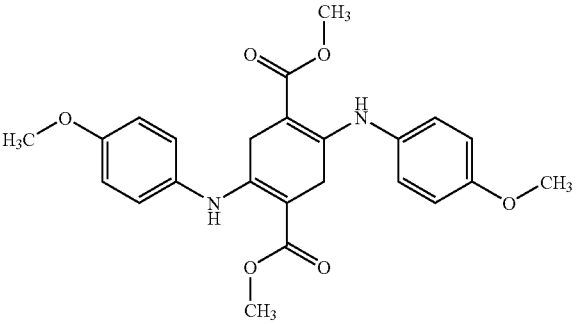 | 2.15 H | H | H | O | O |
| 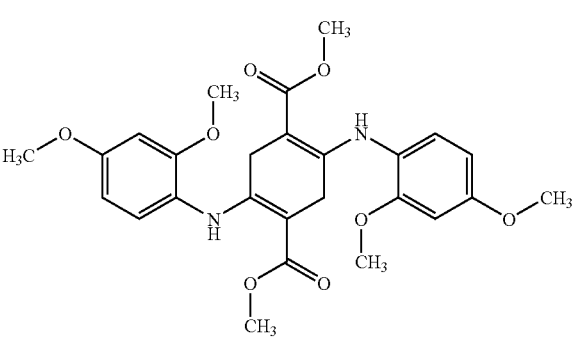 | 2.16 H | H | H | O | O |
| 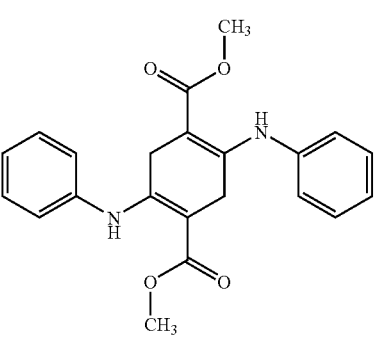 | 2.17 H | H | H | O | O |
| 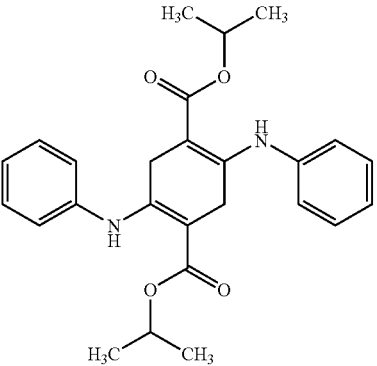 | 2.18 H | H | H | O | O |

TABLE 2-continued

| Structure | # | R1 | R2 | R3 | X | Y |
|---|---|---|---|---|---|---|
| (structure with dimethyl N-phenyl groups and methyl esters) | 2.19 | —CH₃ | H | H | O | O |
| (structure with two pyrenylamino groups and methyl esters) | 2.20 | H | H | H | O | O |
| (structure with two 2,4-dimethoxyphenylamino groups and ethyl esters) | 2.21 | H | H | H | O | O |
| (structure with two 4-dimethylamino-2-methoxyphenylamino groups and methyl esters) | 2.22 | H | H | H | O | O |
| (structure with methylenedioxyphenylamino groups and methyl esters) | 2.24 | H | H | H | O | O |

TABLE 2-continued
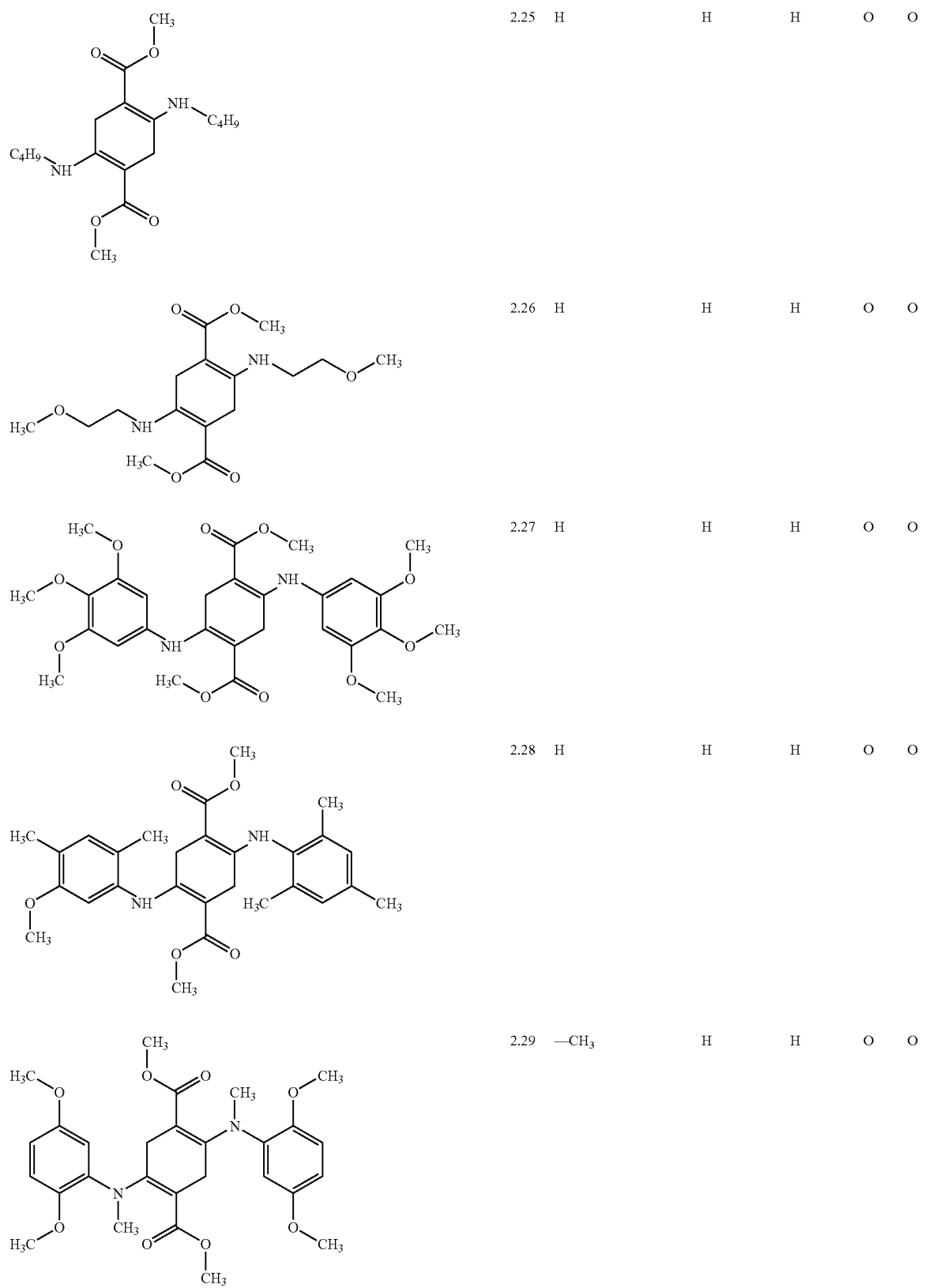
| | | | | | |
|---|---|---|---|---|---|
| 2.25 | H | H | H | O | O |
| 2.26 | H | H | H | O | O |
| 2.27 | H | H | H | O | O |
| 2.28 | H | H | H | O | O |
| 2.29 | —CH₃ | H | H | O | O |

TABLE 2-continued

| | | | | | |
|---|---|---|---|---|---|
| 2.30 | H | H | H | O | O |
| 2.31 | —CH₃ | H | H | O | O |
| 2.32 | —CH₃ | H | H | O | O |
| 2.33 | —CH₃ | H | H | O | O |
| 2.34 | (2-fluorobenzyl) | H | H | O | O |
| 2.35 | H | H | H | O | O |

TABLE 2-continued

| Structure | # | R | | | | |
|---|---|---|---|---|---|---|
| (structure 2.36) | 2.36 | —CH₃ | H | H | O | O |
| (structure 2.37) | 2.37 | H | H | H | O | O |
| (structure 2.38) | 2.38 | 2-fluorophenyl | H | H | O | O |
| (structure 2.39) | 2.39 | 2-fluorophenyl | H | H | O | O |
| (structure 2.40) | 2.40 | phenyl | H | H | O | O |

TABLE 2-continued

| | | | | | |
|---|---|---|---|---|---|
| 2.41 | phenyl(methyl) | H | H | O | O |
| 2.42 | 2-methoxyphenyl(methyl) | H | H | O | O |
| 2.43 | H | H | H | O | O |
| 2.44 | —CH₃ | F | F | O | O |
| 2.45 | —CH₃ | F | F | O | O |
| 2.46 | phenyl(methyl) | F | F | O | O |
| 2.47 | 2-fluorophenyl(methyl) | F | F | O | O |
| 2.48 | —CH₃ | H | H | O | O |
| 2.49 | —CH₃ | H | H | O | O |
| 2.50 | —CH₃ | H | H | O | O |
| 2.51 | —CH₃ | H | H | O | O |
| 2.52 | —CH₃ | H | H | O | O |
| 2.53 | —CH₃ | H | H | O | O |
| 2.54 | —CF₃ | H | H | O | O |
| 2.55 | —CF₃ | H | H | O | O |
| 2.56 | —CF₃ | H | H | O | O |
| 2.57 | —CF₃ | H | H | O | O |
| 2.58 | —CF₃ | H | H | O | O |
| 2.59 | —CF₃ | H | H | O | O |

TABLE 2-continued
| | | | | | |
|---|---|---|---|---|---|
| 2.60 | 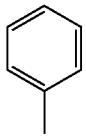 | H | H | O | O |
| 2.61 | 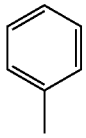 | H | H | O | O |
| 2.62 | 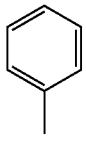 | H | H | O | O |
| 2.63 | 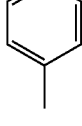 | H | H | O | O |
| 2.64 | 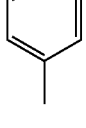 | H | H | O | O |
| 2.65 | 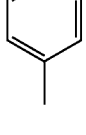 | H | H | O | O |
| 2.66 | 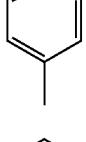 | H | H | O | O |
| 2.67 | 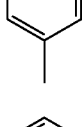 | H | H | O | O |
| 2.68 | 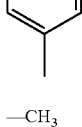 | H | H | O | O |
| 2.69 | —CH$_3$ | H | H | O | O |
| 2.70 | 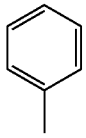 | H | H | O | O |

TABLE 2-continued
| | | R⁸ | R⁸' | R⁵ | R⁶ |
|---|---|---|---|---|---|
| 2.71 | 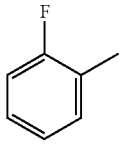 | H | H | O | O |
| 2.72 | 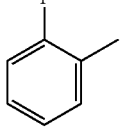 | H | H | O | O |
| 2.73 | 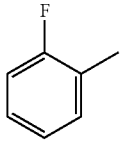 | H | H | O | O |
| 2.74 | H | H | H | N | O |
| 2.75 | 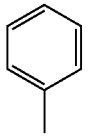 | H | H | N | O |
| 2.76 | —CH₃ | 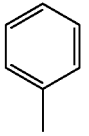 | 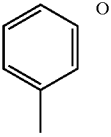 | O | O |
| 2.78 | 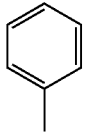 | 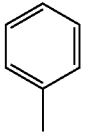 | 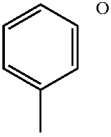 | O | O |
| 2.79 | 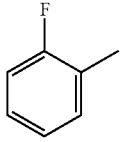 | 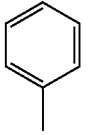 | 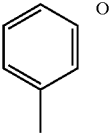 | O | O |
| Substance | R⁸ | R⁸' | R⁵ | R⁶ |
|---|---|---|---|---|
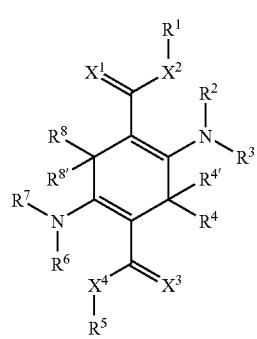
2.0

TABLE 2-continued
| | | | | |
|---|---|---|---|---|
| 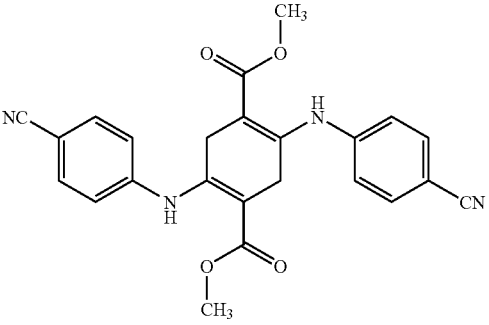 | 2.1 H | H | —CH₃ | H |
| | 2.2 H | H | —CH₃ | —CH₃ |
| | 2.3 H | H | —CH₃ | H |
| | 2.4 H | H | —CH₃ | H |

TABLE 2-continued

| Structure | # | | | | |
|---|---|---|---|---|---|
| 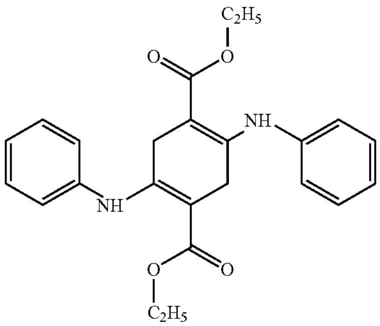 | 2.5 | H | H | —CH₃ | H |
| 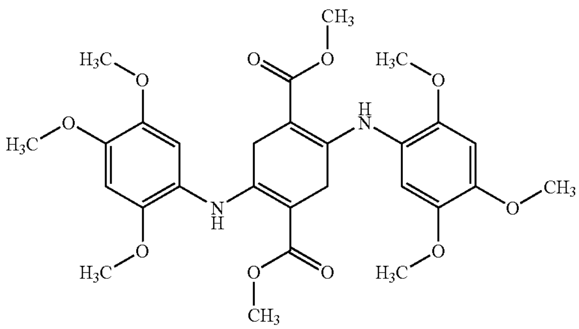 | 2.6 | H | H | —CH₃ | H |
| 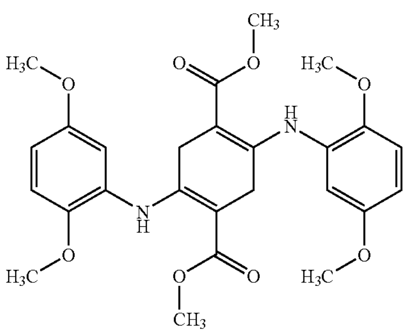 | 2.7 | H | H | —CH₃ | H |
| 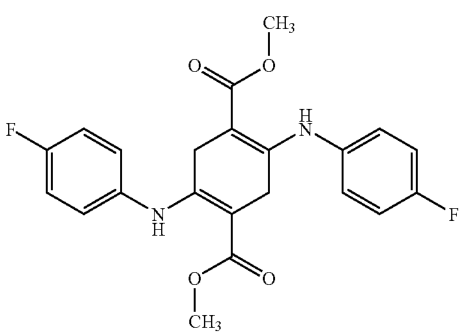 | 2.8 | H | H | —CH₃ | H |
| 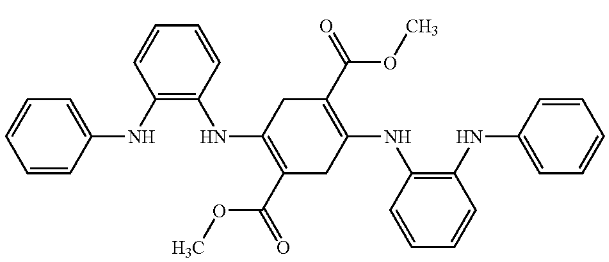 | 2.9 | H | H | —CH₃ | H |

TABLE 2-continued
| | | | | | |
|---|---|---|---|---|---|
| 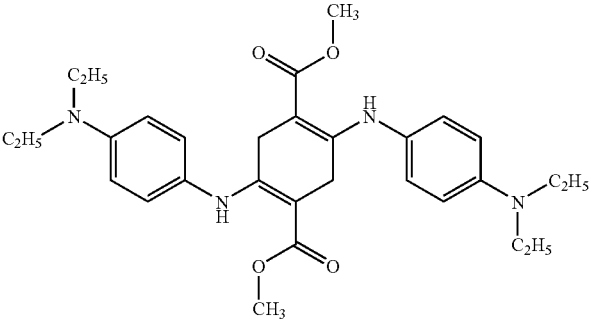 | 2.10 | H | H | —CH$_3$ | H |
| | 2.11 | H | H | —CH$_3$ | H |
| 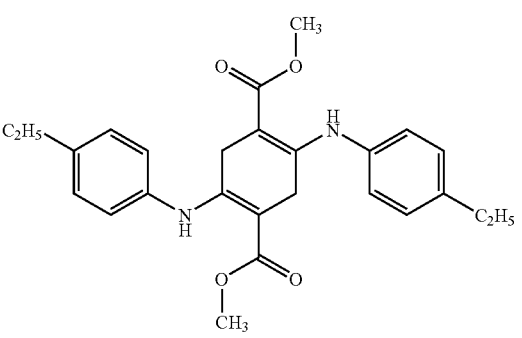 | 2.12 | H | H | —CH$_3$ | H |
| 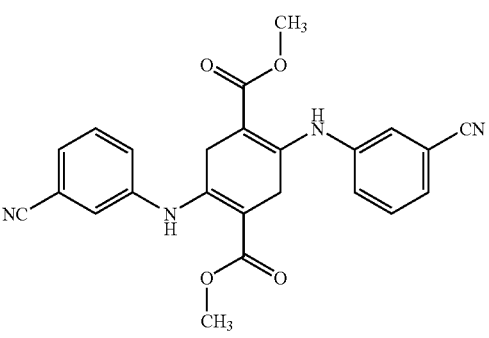 | 2.13 | H | H | —CH$_3$ | H |

TABLE 2-continued

| | | | | |
|---|---|---|---|---|
| [structure] | 2.14 | H | H | —CH₃ | H |
| [structure] | 2.15 | H | H | —CH₃ | H |
| [structure] | 2.16 | H | H | —CH₃ | H |
| [structure] | 2.17 | H | H | —CH₃ | H |

TABLE 2-continued
| Structure | No. | | | | |
|---|---|---|---|---|---|
| 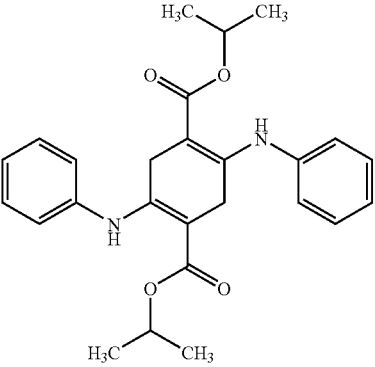 | 2.18 | H | H | —CH$_3$ | H |
| 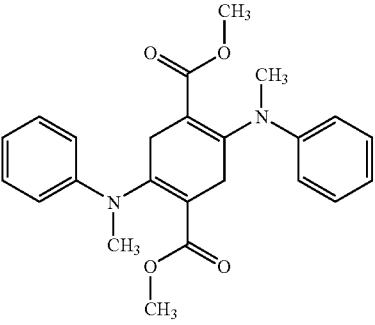 | 2.19 | H | H | —CH$_3$ | —CH$_3$ |
| 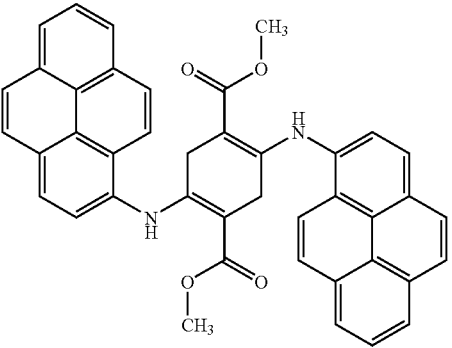 | 2.20 | H | H | —CH$_3$ | H |
| 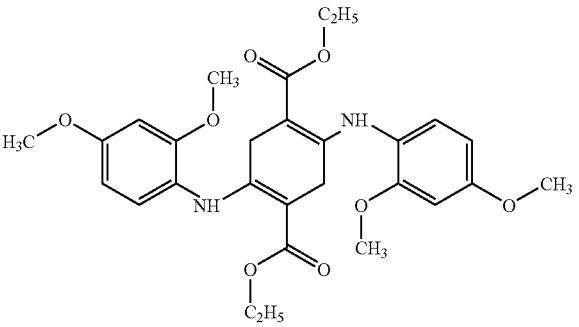 | 2.21 | H | H | —CH$_3$ | H |

TABLE 2-continued

| Structure | # | | | | |
|---|---|---|---|---|---|
| (dimethylamino-methoxyphenyl-NH bis-substituted cyclohexadiene dimethyl dicarboxylate) | 2.22 | H | H | —CH₃ | H |
| (methylenedioxyphenyl / methoxy-methylenedioxyphenyl-NH bis-substituted cyclohexadiene dimethyl dicarboxylate) | 2.24 | H | H | —CH₃ | H |
| (di-C₄H₉-NH substituted cyclohexadiene dimethyl dicarboxylate) | 2.25 | H | H | —CH₃ | H |
| (bis(2-methoxyethyl)amino substituted cyclohexadiene dimethyl dicarboxylate) | 2.26 | H | H | —CH₃ | H |
| (bis(3,4,5-trimethoxyphenyl-NH) substituted cyclohexadiene dimethyl dicarboxylate) | 2.27 | H | H | —CH₃ | H |

TABLE 2-continued

| Structure | # | | | | |
|---|---|---|---|---|---|
| 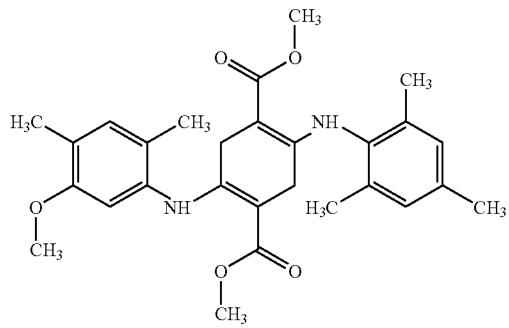 | 2.28 | H | H | —CH₃ | H |
| 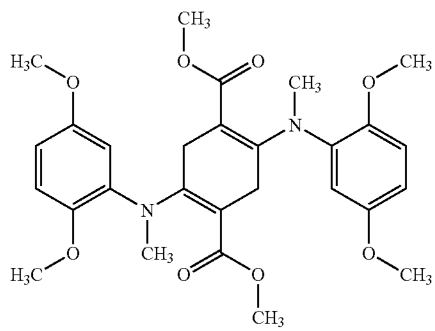 | 2.29 | H | H | —CH₃ | —CH₃ |
| 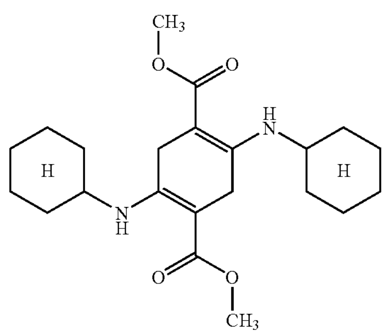 | 2.30 | H | H | —CH₃ | H |
| 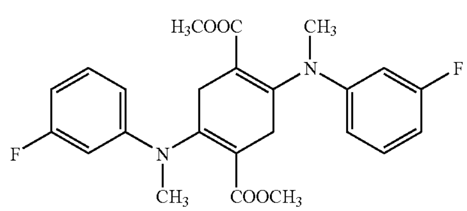 | 2.31 | H | H | —CH₃ | —CH₃ |
| 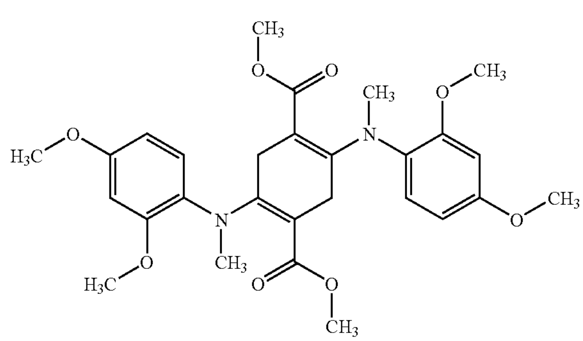 | 2.32 | H | H | —CH₃ | —CH₃ |

TABLE 2-continued

| Structure | # | | | | |
|---|---|---|---|---|---|
| (4-fluorophenyl, N-methyl substituted cyclohexadiene diester) | 2.33 | H | H | —CH₃ | —CH₃ |
| (phenyl/2-fluorophenyl N-substituted cyclohexadiene diester) | 2.34 | H | H | —CH₃ | 2-fluorophenyl |
| (2,6-difluorophenyl NH substituted cyclohexadiene diester) | 2.35 | H | H | —CH₃ | H |
| (2,6-difluorophenyl N-methyl substituted cyclohexadiene diester) | 2.36 | H | H | —CH₃ | —CH₃ |
| (2,4-difluorophenyl NH substituted cyclohexadiene diester) | 2.37 | H | H | —CH₃ | H |
| (2-fluorophenyl N-substituted cyclohexadiene diester) | 2.38 | H | H | —CH₃ | 2-fluorophenyl |

TABLE 2-continued

| Structure | No. | | | | |
|---|---|---|---|---|---|
| (cyclohexyl, 2-fluorophenyl diamino diester structure) | 2.39 | H | H | —CH₃ | 2-fluorophenyl |
| (bis(N-phenyl-N-2-naphthyl)amino diester structure) | 2.40 | H | H | —CH₃ | phenyl |
| (bis(N-phenyl-N-1-naphthyl)amino diester structure) | 2.41 | H | H | —CH₃ | phenyl |
| (bis(2-methoxyphenyl)amino diester with bis(2-methoxyphenyl)methyl structure) | 2.42 | H | H | —CH₃ | 2-methoxyphenyl |

TABLE 2-continued

| | | | | |
|---|---|---|---|---|
| [structure: dimethyl 2,5-bis(1H-indol-5-ylamino)cyclohexa-2,5-diene-1,4-dicarboxylate] | 2.43 | H | H | —CH₃ | H |
| | 2.44 | F | F | —CH₃ | —CH₃ |
| | 2.45 | F | F | —CH₃ | —CH₃ |
| | 2.46 | F | F | —CH₃ | [phenyl] |
| | 2.47 | F | F | —CH₃ | [2-fluorophenyl] |
| | 2.48 | H | H | —CH₃ | —CH₃ |
| | 2.49 | H | H | —CH₃ | —CH₃ |
| | 2.50 | H | H | —CH₃ | —CH₃ |
| | 2.51 | H | H | —CH₃ | —CH₃ |
| | 2.52 | H | H | —CH₃ | —CH₃ |
| | 2.53 | H | H | —CH₃ | —CH₃ |
| | 2.54 | H | H | —CH₃ | —CF₃ |
| | 2.55 | H | H | —CH₃ | —CF₃ |
| | 2.56 | H | H | —CH₃ | —CF₃ |
| | 2.57 | H | H | —CH₃ | —CF₃ |
| | 2.58 | H | H | —CH₃ | —CF₃ |
| | 2.59 | H | H | —CH₃ | —CF₃ |
| | 2.60 | H | H | —CH₃ | [phenyl] |
| | 2.61 | H | H | —CH₃ | [phenyl] |
| | 2.62 | H | H | —CH₃ | [phenyl] |
| | 2.63 | H | H | —CH₃ | [phenyl] |

TABLE 2-continued
| | | | | |
|---|---|---|---|---|
| 2.64 | H | H | —CH₃ | 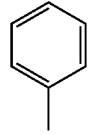 |
| 2.65 | H | H | —CH₃ | 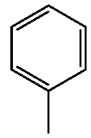 |
| 2.66 | H | H | —CH₃ | 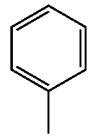 |
| 2.67 | H | H | —CH₃ | 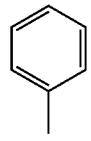 |
| 2.68 | H | H | —CH₃ | 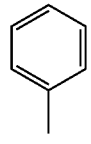 |
| 2.69 | H | H | —CH₃ | —CH₃ |
| 2.70 | H | H | —CH₃ | 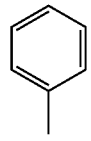 |
| 2.71 | H | H | —CH₃ | 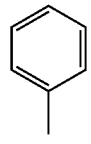 |
| 2.72 | H | H | —CH₃ | 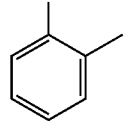 |
| 2.73 | H | H | —CH₃ | 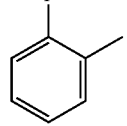 |
| 2.74 | H | H |  | H |

TABLE 2-continued
| | | | | |
|---|---|---|---|---|
| 2.75 | H | H | 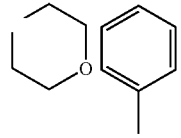 | |
| 2.76 | 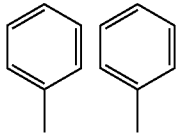 | 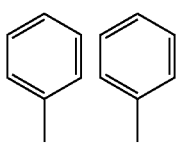 | —CH₃ | —CH₃ |
| 2.78 | 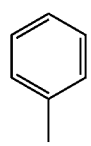 | 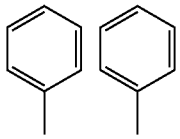 | —CH₃ | 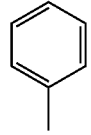 |
| 2.79 | | | —CH₃ | |
| Substance | R⁷ |
|---|---|
|  | 2.0 |
| 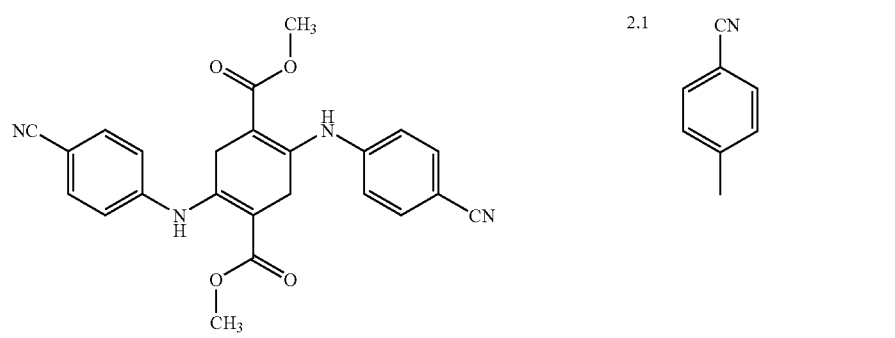 | 2.1 |

TABLE 2-continued
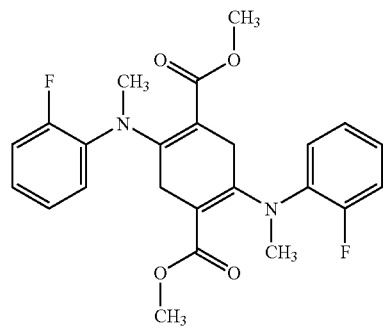 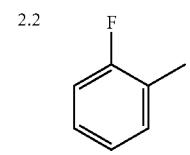
2.2
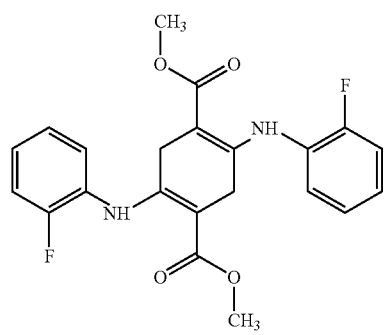 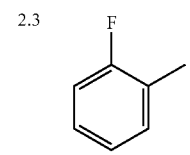
2.3
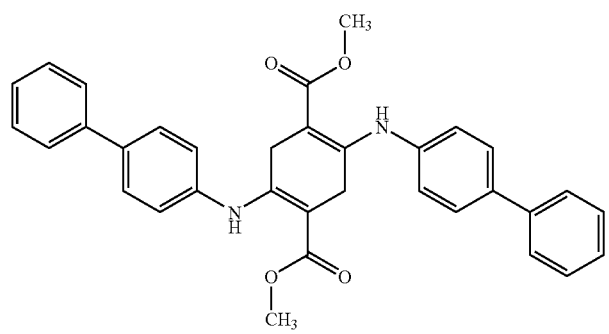 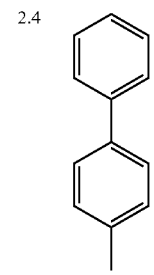
2.4
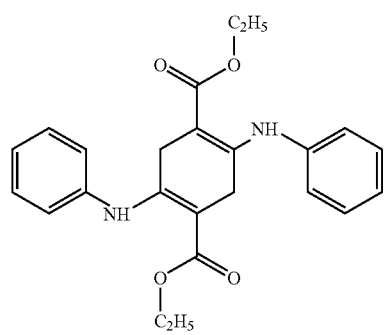 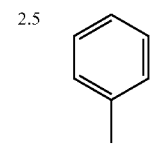
2.5

TABLE 2-continued
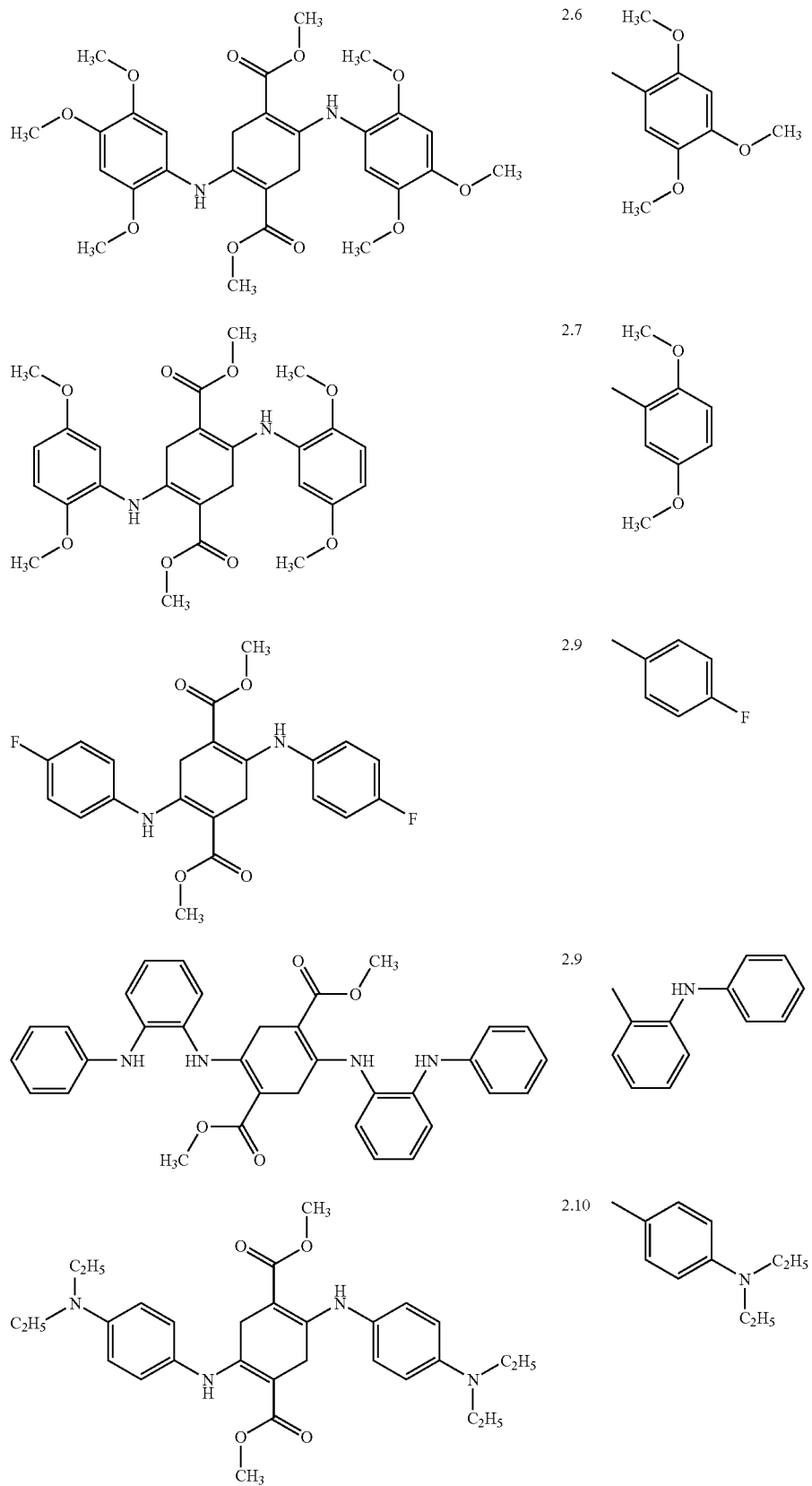

TABLE 2-continued
| | | |
|---|---|---|
| 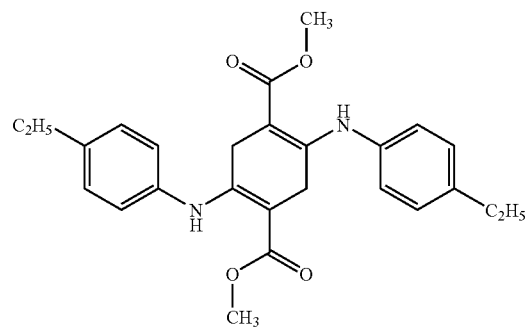 | 2.11 | 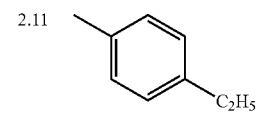 |
| 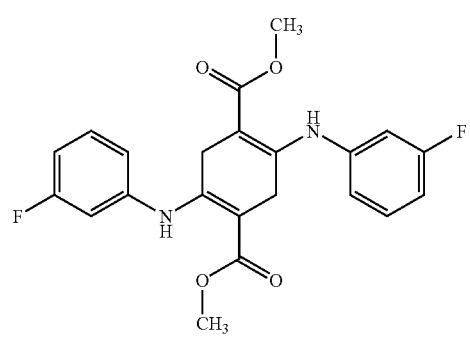 | 2.12 | 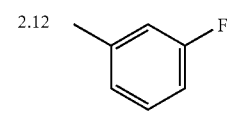 |
| 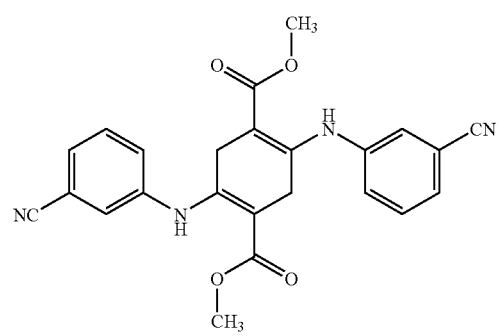 | 2.13 | 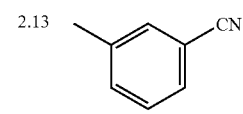 |
| 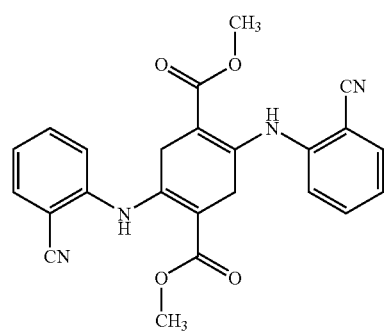 | 2.14 | 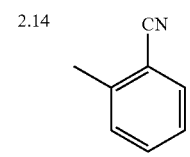 |

TABLE 2-continued
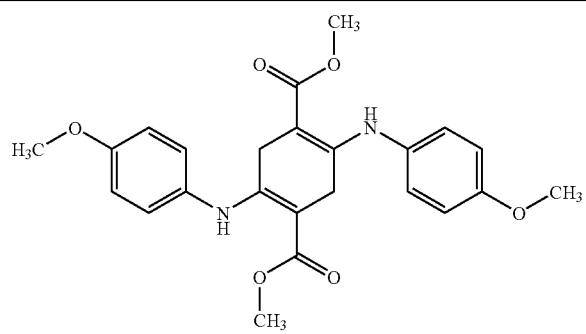 2.15 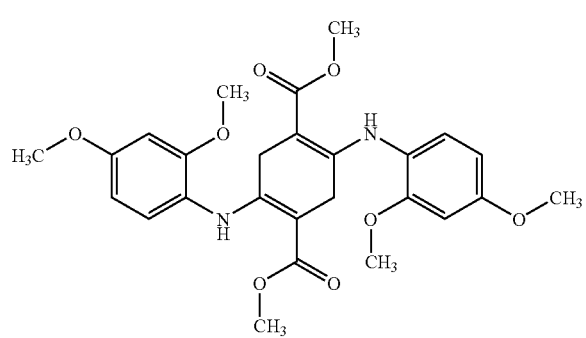
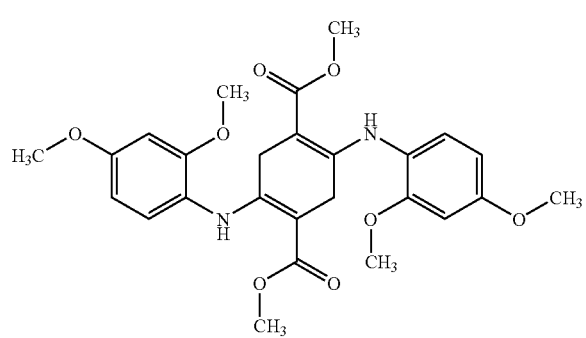 2.16
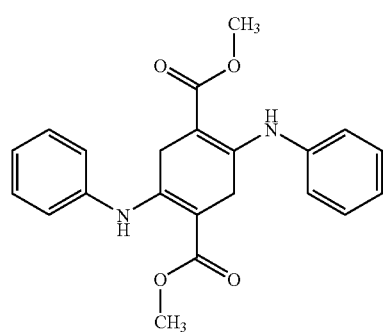 2.17
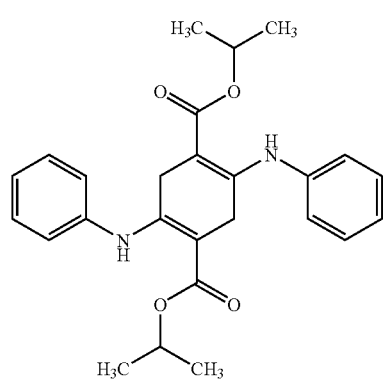 2.18

TABLE 2-continued
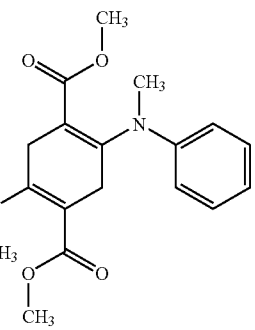 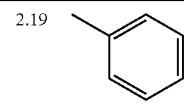
2.19
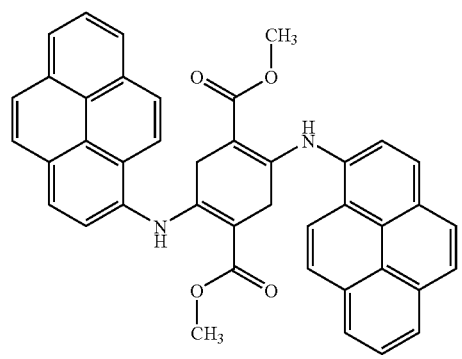 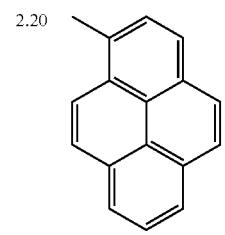
2.20
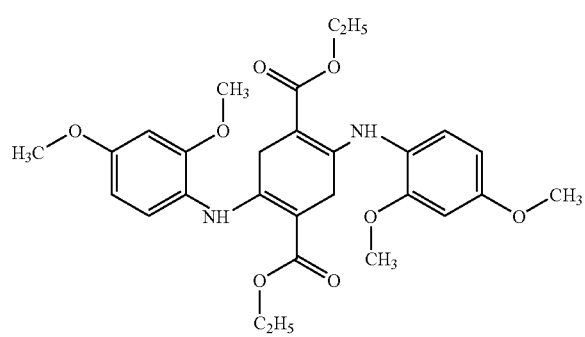 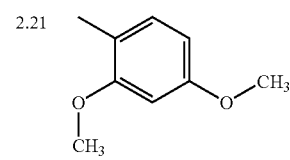
2.21
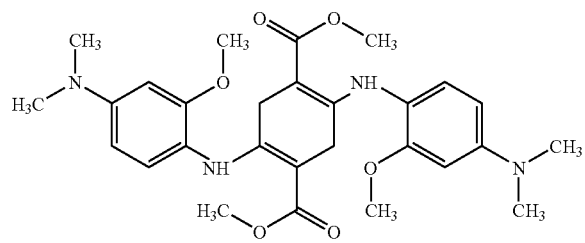 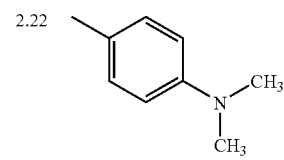
2.22
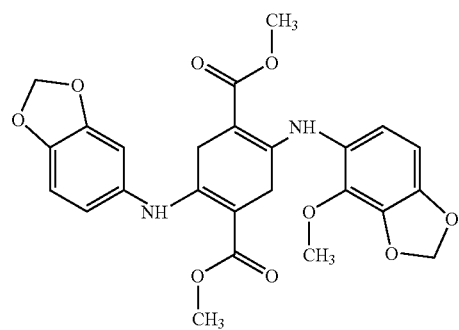 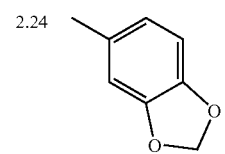
2.24

TABLE 2-continued
| | | |
|---|---|---|
| 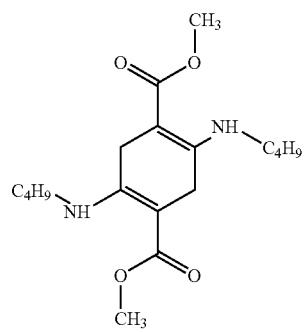 | 2.25 | —C$_4$H$_9$ |
| 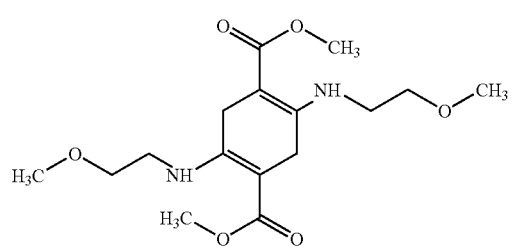 | 2.26 | <img structure> |
| 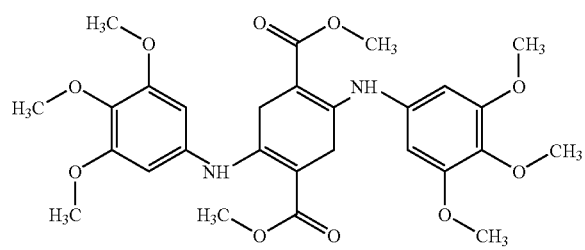 | 2.27 | <img structure> |
| 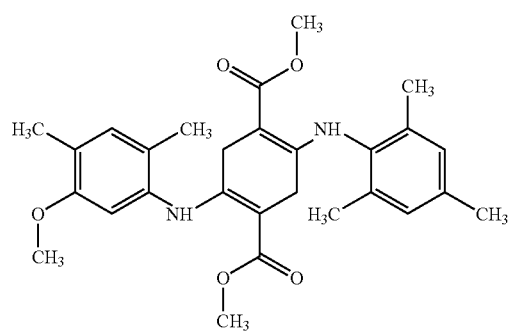 | 2.28 | <img structure> |
| 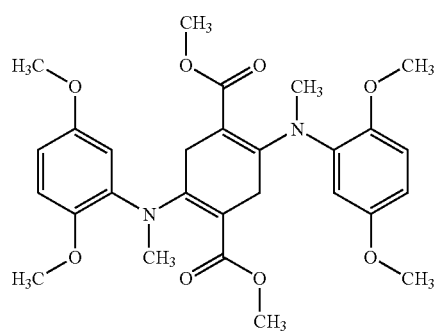 | 2.29 | <img structure> |

TABLE 2-continued
| | | |
|---|---|---|
| 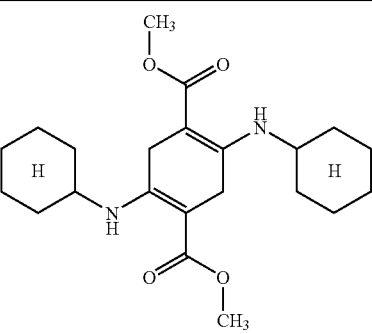 | 2.30 | 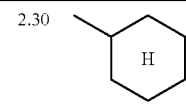 |
| 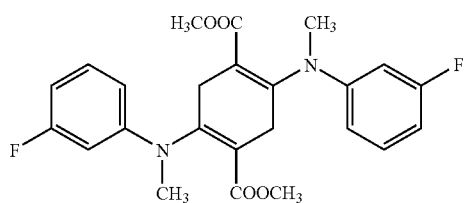 | 2.31 | 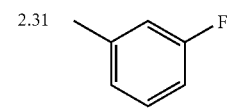 |
| 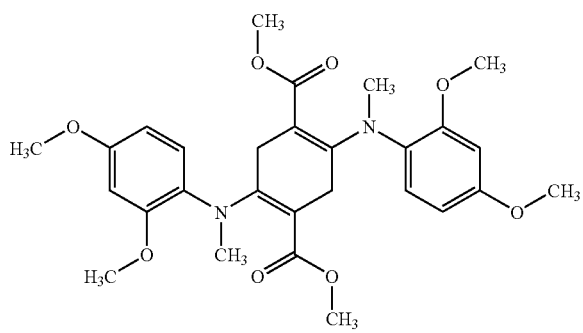 | 2.32 | 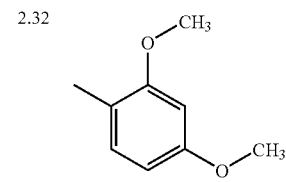 |
| 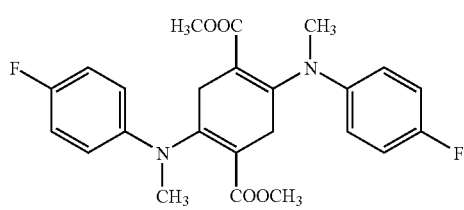 | 2.33 | 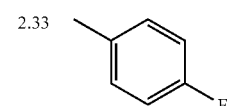 |
| 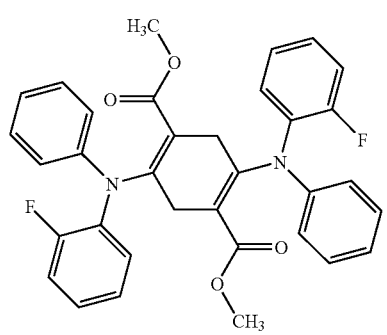 | 2.34 | 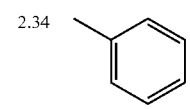 |
| 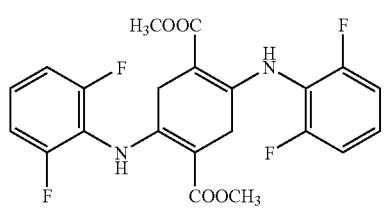 | 2.35 | 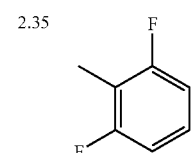 |

TABLE 2-continued
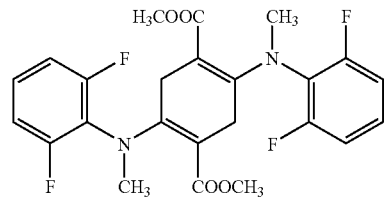 | 2.36 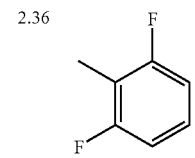
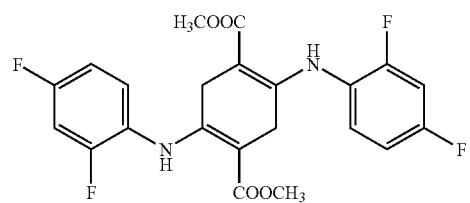 | 2.37 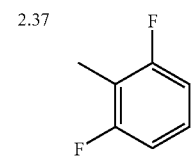
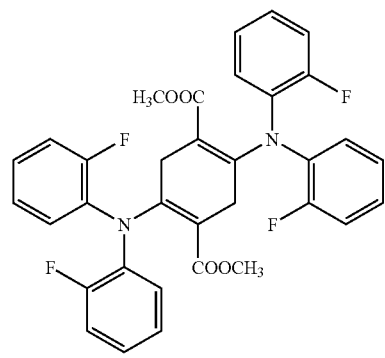 | 2.38 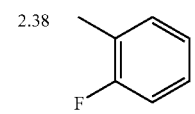
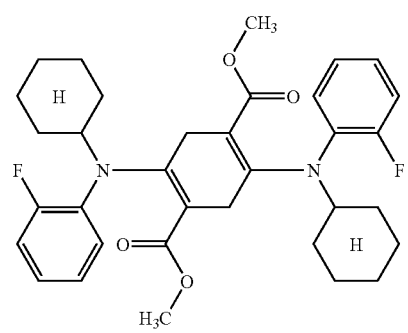 | 2.39 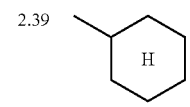
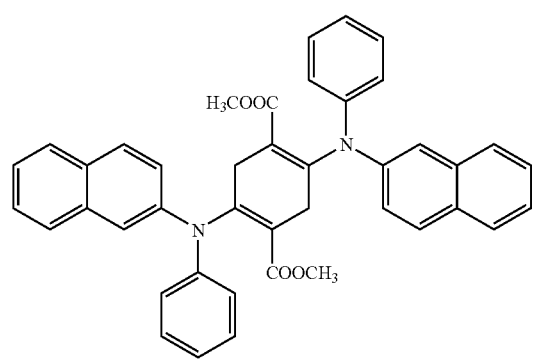 | 2.40 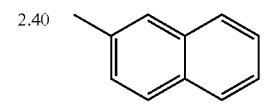

TABLE 2-continued
| | |
|---|---|
| 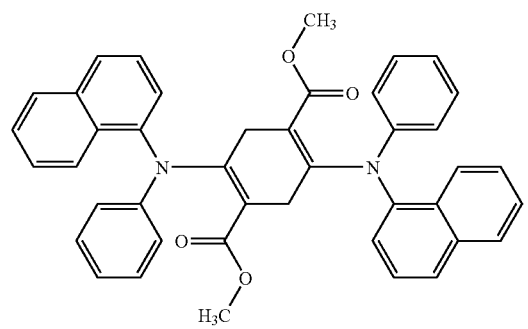 | 2.41 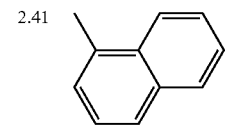 |
| 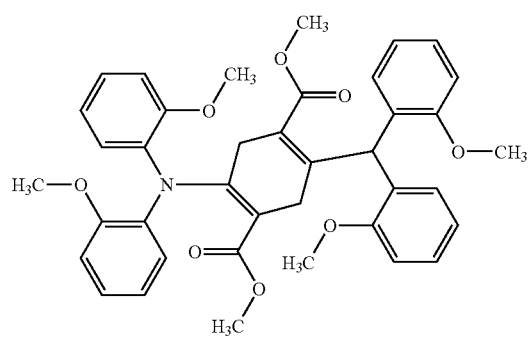 | 2.42 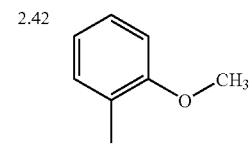 |
| 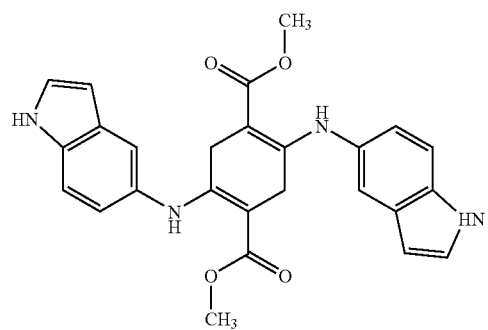 | 2.43 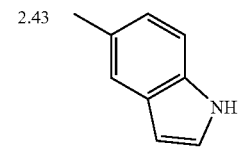 |
| | 2.44 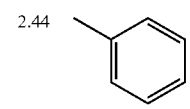 |
| | 2.45 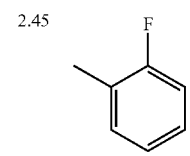 |
| | 2.46 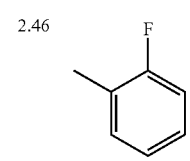 |
| | 2.47 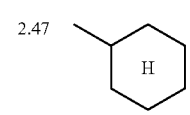 |

TABLE 2-continued
| | |
|---|---|
| 2.48 | 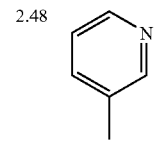 |
| 2.49 | 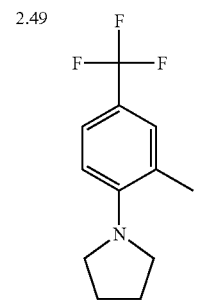 |
| 2.50 | 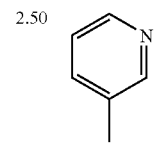 |
| 2.51 | 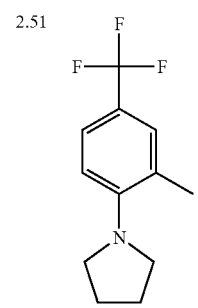 |
| 2.52 | 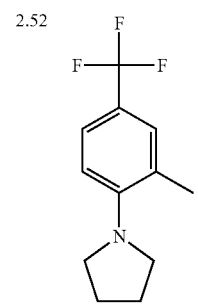 |
| 2.53 | 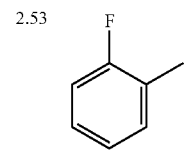 |
| 2.54 | 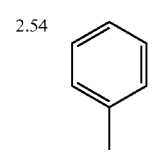 |

TABLE 2-continued
| | |
|---|---|
| 2.55 | 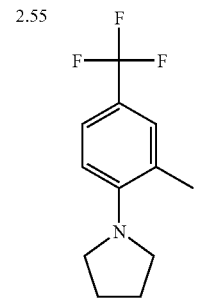 |
| 2.56 | 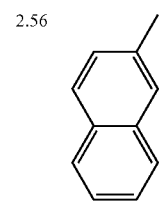 |
| 2.57 | 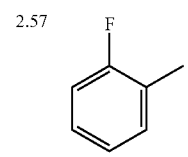 |
| 2.58 | 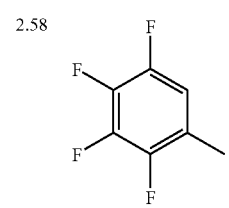 |
| 2.59 | 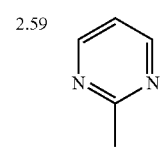 |
| 2.60 | 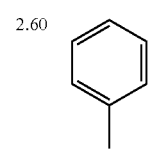 |
| 2.61 | 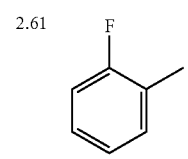 |
| 2.62 | 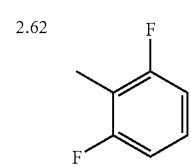 |

TABLE 2-continued
2.63 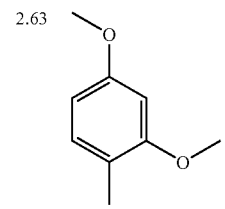
2.64 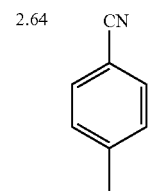
2.65 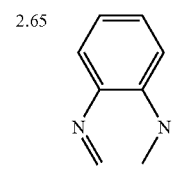
2.66 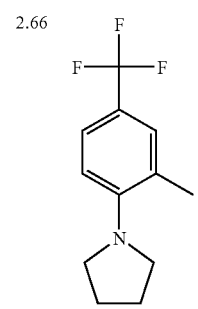
2.67 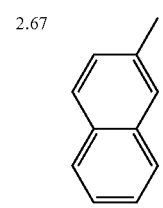
2.68 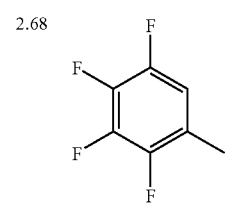
2.69 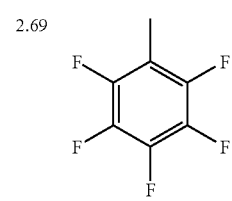

TABLE 2-continued
| | |
|---|---|
| 2.70 | 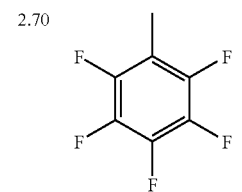 |
| 2.71 | 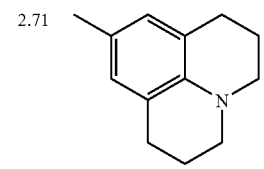 |
| 2.72 | 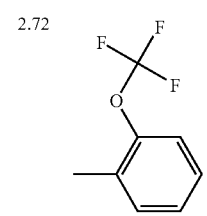 |
| 2.73 | 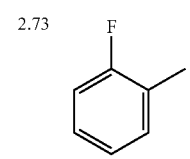 |
| 2.74 | 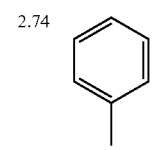 |
| 2.75 | 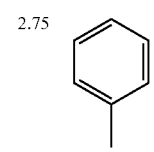 |
| 2.76 | 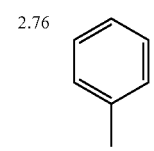 |
| 2.78 | 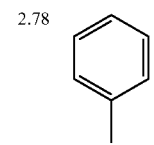 |
| 2.79 | 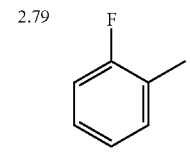 |

TABLE 2-continued
| Substance | X¹ X² | R³ | R¹ | R² | R⁴ X⁴ | X³ | R⁸ | R⁵ | R⁶ | R⁷ |
|---|---|---|---|---|---|---|---|---|---|---|
| 37.0 | | | | | | | | | | |
| 37.1 | (benzo-diaza) | (phenyl) | —CH₃ | —CH₃ | H (benzo-diaza) | H | —CH₃ | —CH₃ | | (phenyl) |
| 37.2 | (benzo-diaza) | (phenyl) | (phenyl) | —CH₃ | H (benzo-diaza) | H | (phenyl) | —CH₃ | | (phenyl) |
| Substance | R⁴' | R⁸' |
|---|---|---|
| 37.0 | | |
| 37.1 | H | H |
| 37.2 | H | H |
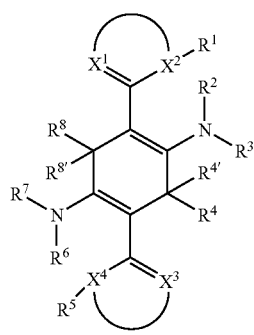
| Substance | X¹ X² | R³ | R¹ | R² | R⁴ X⁴ | X³ | R⁸ | R⁵ | R⁶ | R⁷ |
|---|---|---|---|---|---|---|---|---|---|---|
| 37.3 | (benzo-N-O) | (phenyl) | — | —CH₃ | H (benzo-N-O) | H | — | | —CH₃ | (phenyl) |
| 37.4 | (benzo-N-S) | (phenyl) | — | —CH₃ | H (benzo-N-S) | H | — | | —CH₃ | (phenyl) |

TABLE 2-continued
23.0 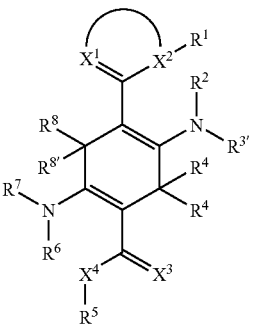
23.1 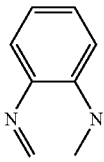 —CH₃  H  O  O  H  —CH₃  —CH₃ 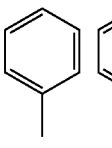
30.0 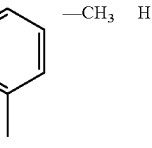
30.1  O  O 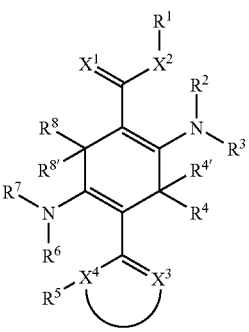 —CH₃ —CH₃  H 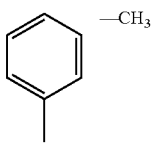 —CH₃ —CH₃ 
| Substance | R⁴′ | R⁸′ |
|---|---|---|
| 37.3 | H | H |
| 37.4 | H | H |
23.0 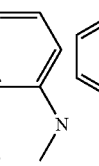
23.1  H  H TABLE 2-continued

| Substanz | X¹ | X² | R³ | R² | R¹ | R⁴ | X⁴ |
|---|---|---|---|---|---|---|---|
| 30.0 | | | | | | | |
| 30.1 | | | H | phenyl | | | |
| 39.0 | | | | | | | |
| 39.1 | O | O | phenyl | —CH₂— | — | H | O |
| 39.2 | O | O | benzo[1,3]dioxol-5-yl | —CH₂— | — | H | O |
| 39.3 | O | O | 4-methoxyphenyl | —CH₂— | — | H | O |

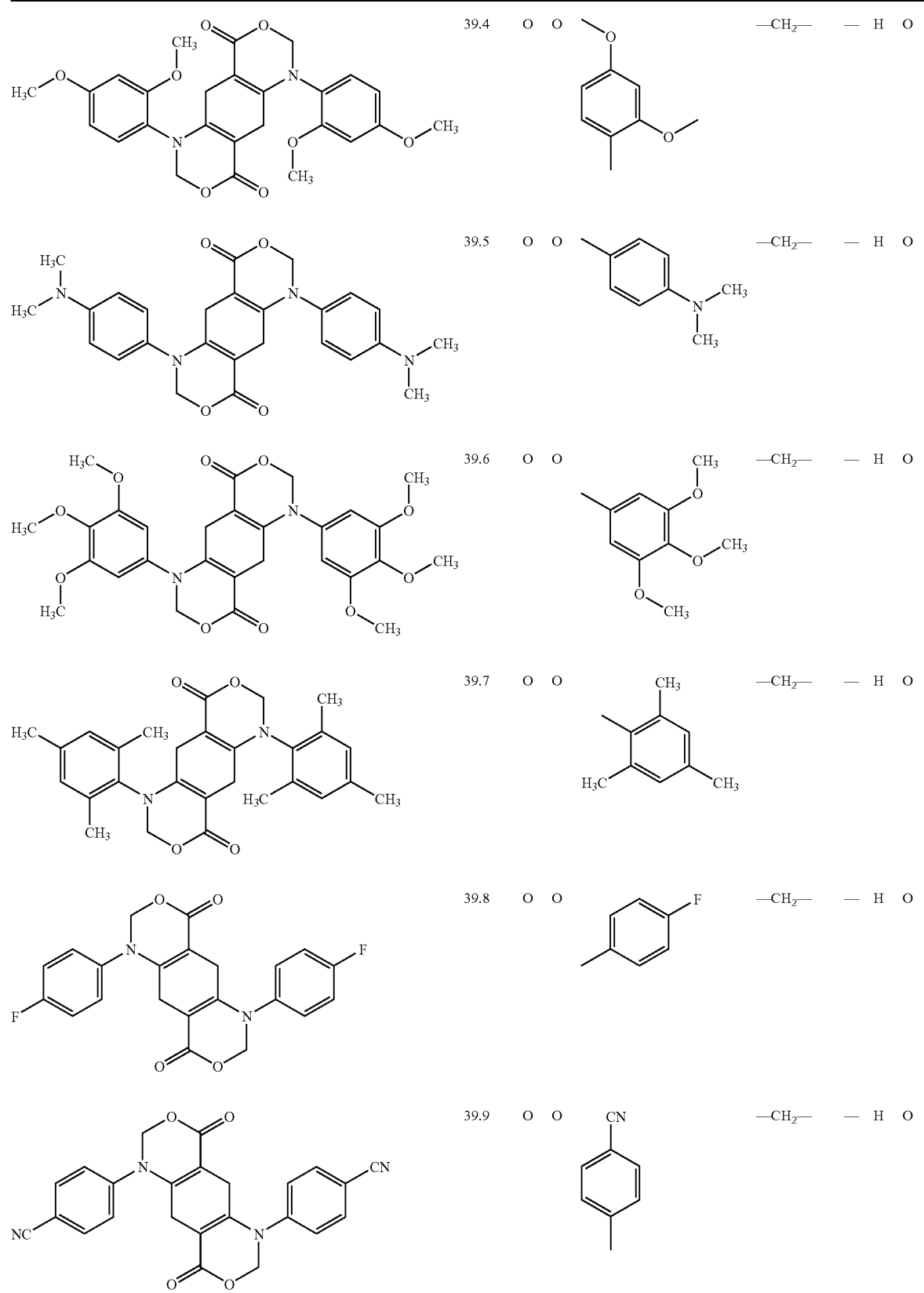

TABLE 2-continued
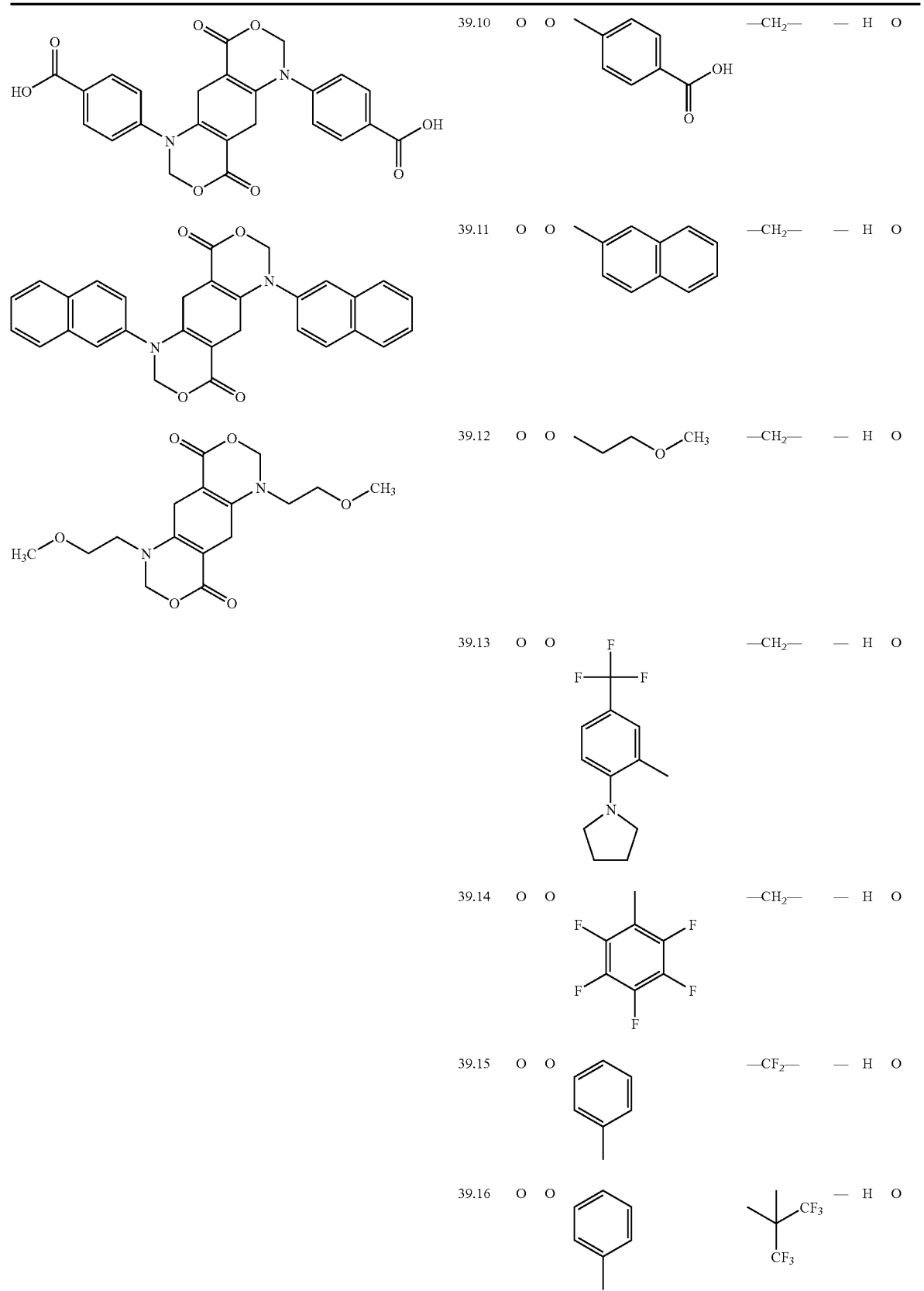

TABLE 2-continued
| | | X¹ | X² | R¹ R² | R³ | R⁴ R⁸ |
|---|---|---|---|---|---|---|
| 39.17 | | O | O | 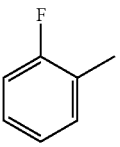 | 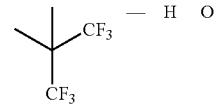 | — H O |
| 39.18 | | O | O | 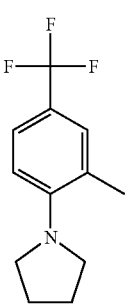 | —CH₂— | — H O |
| 39.19 | | O | O | 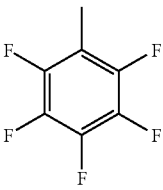 | —CH₂— | — H O |
| 39.20 | | O | O | 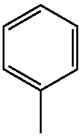 | —CF₂— | — H O |
| 39.21 | | O | O | 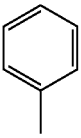 | 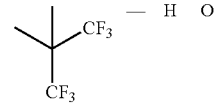 | — H O |
| 39.22 | | O | O | 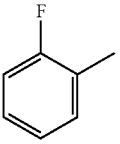 | 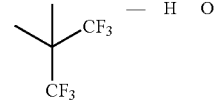 | — H O |
| Substanz | X³ R⁸ R⁶ | R⁵ R⁷ | R⁴' R⁸' |
|---|---|---|---|
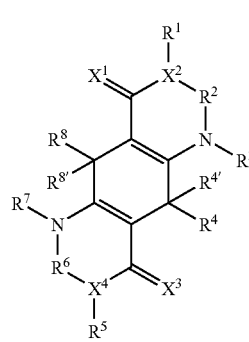
39.0

TABLE 2-continued

| | | | | | | | | |
|---|---|---|---|---|---|---|---|---|
| (structure) | 39.1 | O | H | —CH₂— | — | (phenyl) | H | H |
| (structure) | 39.2 | O | H | —CH₂— | — | (benzo[1,3]dioxole) | H | H |
| (structure) | 39.3 | O | H | —CH₂— | — | (4-methoxyphenyl) | H | H |
| (structure) | 39.4 | O | H | —CH₂— | — | (2,4-dimethoxyphenyl) | H | H |
| (structure) | 39.5 | O | H | —CH₂— | — | (4-dimethylaminophenyl) | H | H |
| (structure) | 39.6 | O | H | —CH₂— | — | (3,4,5-trimethoxyphenyl) | H | H |

TABLE 2-continued
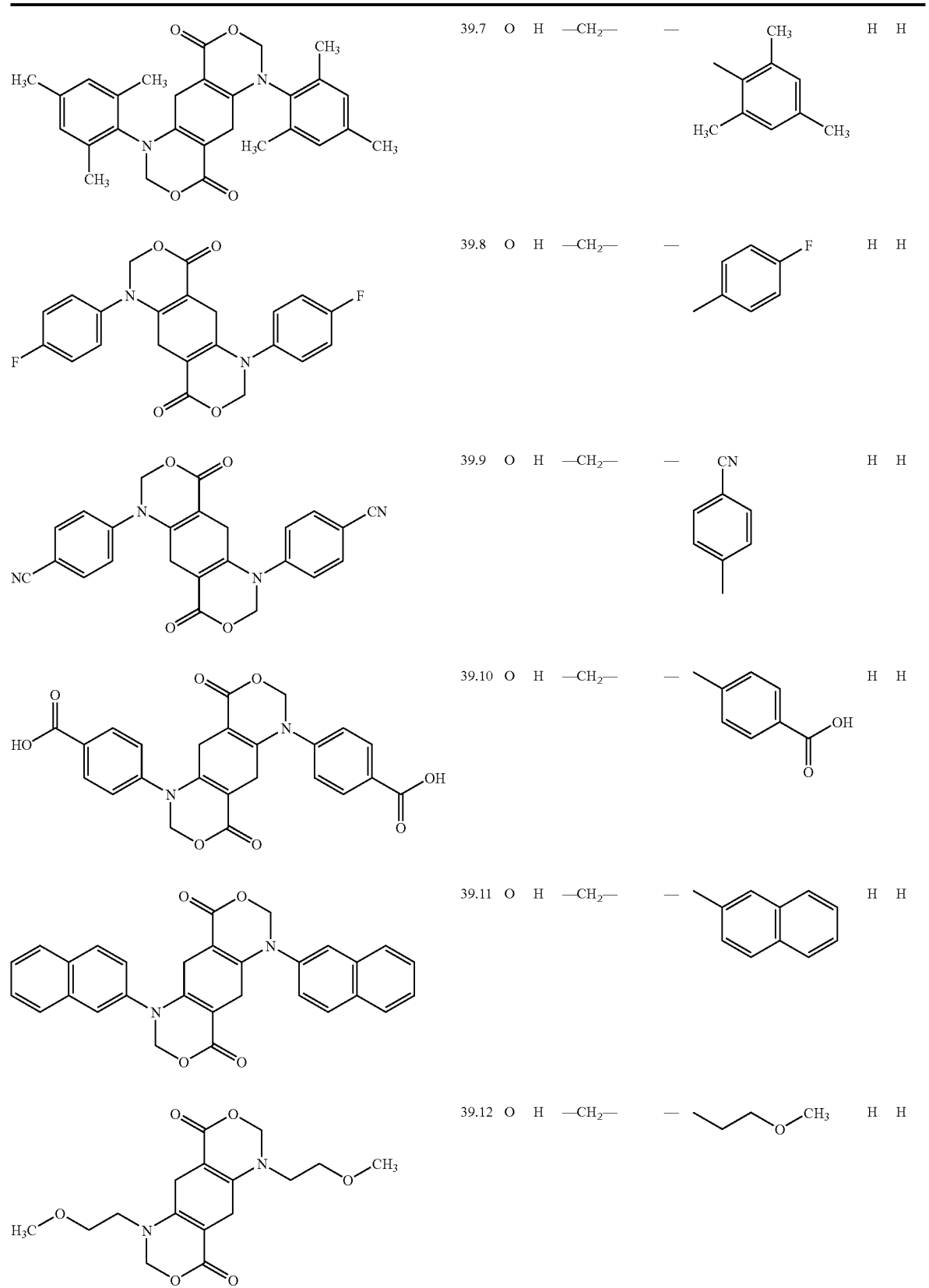
| | | | | | | | |
|---|---|---|---|---|---|---|---|
| 39.7 | O | H | —CH₂— | — | 2,4,6-trimethylphenyl | H | H |
| 39.8 | O | H | —CH₂— | — | 4-fluorophenyl | H | H |
| 39.9 | O | H | —CH₂— | — | 4-cyanophenyl | H | H |
| 39.10 | O | H | —CH₂— | — | 4-carboxyphenyl | H | H |
| 39.11 | O | H | —CH₂— | — | 2-naphthyl | H | H |
| 39.12 | O | H | —CH₂— | — | —CH₂CH₂OCH₃ | H | H |

TABLE 2-continued
| | | | | | | | |
|---|---|---|---|---|---|---|---|
| 39.13 | O | H | —CH₂— | — | 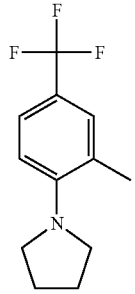 | H | H |
| 39.14 | O | H | —CH₂— | — | 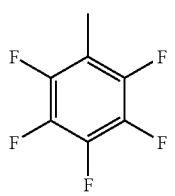 | H | H |
| 39.15 | O | H | —CF₂— | — | 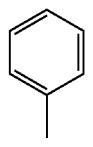 | H | H |
| 39.16 | O | H | 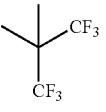 | — | 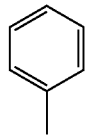 | H | H |
| 39.17 | O | H | 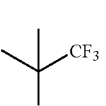 | — | 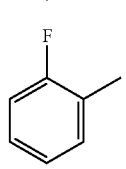 | H | H |
| 39.18 | O | H | —CH₂— | — | 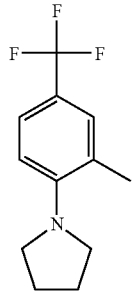 | H | H |
| 39.19 | O | H | —CH₂— | — |  | H | H |
| 39.20 | O | H | —CF₂— | — | 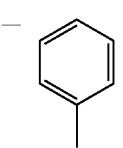 | H | H |

TABLE 2-continued

| | | X¹ | X² | R³ | R² | R¹ | R⁴ | X⁴ | X³ | R⁸ | R⁶ | R⁵ | R⁷ | R⁴' |
|---|---|---|---|---|---|---|---|---|---|---|---|---|---|---|
| | 39.21 | O | H | C(CF₃)₂ (t-Bu-like with two CF₃) | — | phenyl | | | | | | | H | H |
| | 39.22 | O | H | C(CF₃)₂ | — | 2-fluorophenyl | | | | | | | H | H |
| SUBSTANCE 25.0 (structure shown) | | | | | | | | | | | | | | |
| | 25.1 | O | O | phenyl | | —CH₂— | H | O | O | H | —CH₃ | —CH₃ | phenyl | H |
| | 25.2 | O | O | phenyl | | —CH₂— | H | N | O | H | tetrahydropyranyl | —CH₃ | phenyl | H |
| 32.0 (structure shown) | | | | | | | | | | | | | | |
| | 32.1 | O | O | phenyl | tetrahydropyranyl | —CH₃ | H | N | O | H | —CH₂— | | 2-fluorophenyl | H |
| | 32.2 | O | O | 2-fluorophenyl | tetrahydropyranyl | —CH₃ | H | N | O | H | —CH₂— | | phenyl | H |

TABLE 2-continued

| | SUBSTANCE | $R^{8'}$ |
|---|---|---|
| | 25.0 (structure) | |
| | 25.1 | H |
| | 25.2 | H |
| | 32.0 (structure) | |
| | 32.1 | H |
| | 32.2 | H |

| Substance | $X^1$ | $R^1$ | $X^2$ | $R^2$ | $R^3$ | $R^4$ | $R^5$ | $X^3$ | $X^4$ | $R^6$ | $R^7$ | $R^8$ |
|---|---|---|---|---|---|---|---|---|---|---|---|---|
| 40.0 (structure) | | | | | | | | | | | | |
| 40.1 | O | —CH₃ | O | | 2-biphenyl | H | —CH₃ | O | O | | 2-biphenyl | H |
| 40.2 | O | —CH₃ | O | | 2-ethylphenyl | H | —CH₃ | O | O | | 2-ethylphenyl | H |
| 40.3 | O | —CH₃ | O | | tetrahydronaphthyl | H | —CH₃ | O | O | | tetrahydronaphthyl | H |

TABLE 2-continued

| | | | | | | | | | | |
|---|---|---|---|---|---|---|---|---|---|---|
| 40.4 | O | —CH₃ | O | [indane] | H | —CH₃ | O | O | [indane] | H |

26.0

[Structure: benzene ring with substituents X¹=R¹, X²; R², R³ on N; R⁸, R⁸'; R⁴', R⁴; R⁷, R⁶ on N; X⁴=X³, R⁵]

| | | | | | | | | | | |
|---|---|---|---|---|---|---|---|---|---|---|
| 26.1 | O | —CH₃ | O | [indane] | H | —CH₃ | O | O | —CH₃ | [phenyl] | H |
| 26.2 | O | —CH₃ | O | [indane] | H | —CH₃ | O | O | [phenyl][phenyl] | H |
| 26.3 | O | —CH₃ | O | [indane] | [phenyl] | —CH₃ | O | O | [phenyl][phenyl] | H |

| Substance | R⁴' | R⁸' |
|---|---|---|
| 40.0 [Structure shown] | | |
| 40.1 | H | H |
| 40.2 | H | H |
| 40.3 | H | H |
| 40.4 | H | H |

TABLE 2-continued

| Substance | X¹ | R¹ | X² | R⁴ | R² | R³ | R⁵ | X³ | X⁴ | R⁶ | R⁷ | R⁸ | R⁴' |
|---|---|---|---|---|---|---|---|---|---|---|---|---|---|
| 26.1 | | | | | H | H | | | | | | | |
| 26.2 | | | | | H | H | | | | | | | |
| 26.3 | | | | | —C₆H₅ | H | | | | | | | |
| 33.1 | O | —CH₃ | O | —CH₃ | —C₆H₅ | —C₆H₅ | —CH₃ | O | O | —CH₂C₆H₅ | H | —CH₃ | |
| 33.2 | O | —CH₃ | O | —C₆H₅ | —C₆H₅ | —C₆H₅ | —CH₃ | O | O | —CH₂C₆H₅ | H | —C₆H₅ | |

| Substance | R⁸' |
|---|---|
| 33.1 | H |
| 33.2 | H |

TABLE 2-continued

| Substance | | R¹ X² X¹ R⁴ R³ | R² | R⁵ X³ X³ R⁸ R⁷ | R⁶ | R⁴' R⁸' |
|---|---|---|---|---|---|---|
| 38.0 | (structure shown) | | | | | |
| 38.1 | | pyrrolidine-N— O H | phenyl | pyrrolidine-N— O H | phenyl —CH₃ | H H |
| | | | —CH₃ | | | |
| 38.2 | | piperidine-N— O H | phenyl —CH₃ | piperidine-N— O H | phenyl —CH₃ | H H |
| 38.3 | | morpholine-N— O H | phenyl —CH₃ | morpholine-N— O H | phenyl —CH₃ | H H |
| 38.4 | | 2-(2-hydroxyethyl)-N-methylpyrrolidine O H | phenyl —CH₃ | 2-(2-hydroxyethyl)-N-methylpyrrolidine O H | phenyl —CH₃ | H H |
| 24.0 | (structure shown) | | | | | |
| 24.1 | | morpholine-N— O H | phenyl | —CH₃ O O H | phenyl —CH₃ | H H |

TABLE 2-continued

| | | | | | | | | | | | | |
|---|---|---|---|---|---|---|---|---|---|---|---|---|
| 24.2 | morpholine-N-O | H | phenyl(tolyl) | phenyl(tolyl) | —CH₃ | O | O | H | phenyl(tolyl) | phenyl(tolyl) | H | H |

31.0

[Structure: benzene ring with substituents X¹=X²–R¹ (with R² on adjacent N-R³), R⁸, R⁸', R⁷-N, R⁶, R⁴', R⁴, and X⁴=X³–R⁵]

| | | | | | | | | | | | | |
|---|---|---|---|---|---|---|---|---|---|---|---|---|
| 31.1 | —CH₃ | O | O | H | phenyl(tolyl) | —CH₃ | morpholine-N-O | H | phenyl(tolyl) | H | H | H |
| 31.2 | —CH₃ | O | O | H | phenyl(tolyl) | phenyl(tolyl) | morpholine-N-O | H | phenyl(tolyl) | —CH₃ | H | H |

| Substance | R¹ | X² | X¹ | R⁴' | R³ | R² | R⁵ | X⁴ | X³ | R⁸' | R⁷ | R⁶ |
|---|---|---|---|---|---|---|---|---|---|---|---|---|

41.0

[Structure: bicyclic benzene-fused ring system with substituents X¹=X²–R¹, R², R³, R⁴', R⁵–X⁴=X³, R⁶, R⁷, R⁸]

| | | | | | | | | | | |
|---|---|---|---|---|---|---|---|---|---|---|
| 41.1 | —CH₃ | O | O | 2-ethylphenyl | 2-fluorophenyl | —CH₃ | O | O | 2-ethylphenyl | 2-fluorophenyl |

TABLE 2-continued
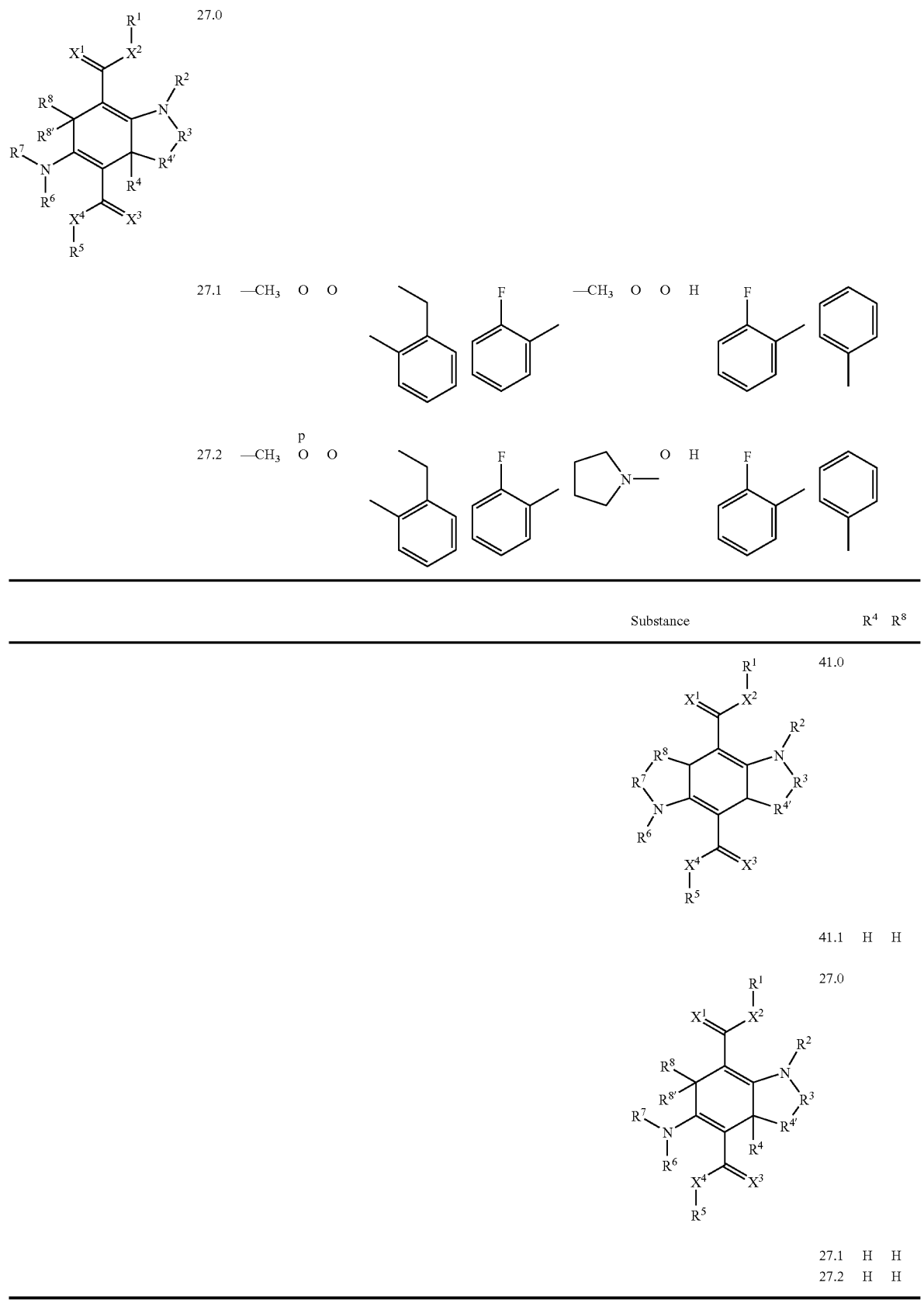

TABLE 2-continued

| Substance | R¹ | X² | X¹ | R⁴ | R³ | R² | R⁵ | X⁴ | X³ | R⁵ | R⁷ | R⁸' | R⁴' | R⁸ |
|---|---|---|---|---|---|---|---|---|---|---|---|---|---|---|

34.0

[structure shown]

| 34.1 | N-pyrrolidinyl | O | H | 2-fluorophenyl | | —CH₃ | —CH₃ | O | O | 2-fluorophenyl | 2-ethylphenyl | H | H | |

| Substance | X² | R² | R³ | R⁴ | X³ | R⁵ | R⁶ | X⁴ | R⁷ | R⁸ | X¹ |
|---|---|---|---|---|---|---|---|---|---|---|---|

43.0

[structure shown]

| 43.1 | O | —CH₃ | 4-tolyl | =N-(2-tolyl) | —CH₃ | —CH₃ | | O | 4-tolyl | =N-(2-tolyl) | |

29.0

[structure shown]

| 29.1 | O | —CH₃ | 4-tolyl | =N-(2-tolyl) | —CH₃ | —CH₃ | | O | 4-tolyl | H | O |

TABLE 2-continued

| | | | | | | | | | |
|---|---|---|---|---|---|---|---|---|---|
| 29.2 | O | (tetrahydropyran) | (N=CH-o-tolyl) | —CH₃ | —CH₃ | O | | H | O |

[Structure diagram with substituents R¹, X², X¹, R⁸, R⁸', R⁷, N-R⁶, X⁴, X³, R⁵, R², N-R³, R⁴', R⁴]

36.0

| | | | | | | | | | |
|---|---|---|---|---|---|---|---|---|---|
| 36.1 | O | (tetrahydropyran) | H | O | —CH₃ | —CH₃ | O | (phenyl) | (N=CH-o-tolyl) |

| Substance | R¹ | R⁴' | R⁸' |
|---|---|---|---|

[Structure diagram 43.0 with fused bicyclic system]

43.0

| 43.1 | —CH₃ | —CH₃ | —CH₃ |
|---|---|---|---|

[Structure diagram 29.0 with fused bicyclic system]

29.0

| 29.1 | —CH₃ | —CH₃ | —CH₃ |
|---|---|---|---|
| 29.2 | —CH₃ | H | H |

TABLE 2-continued

[Structure 36.0: bicyclic structure with substituents R¹, X², X¹, R⁸, R⁸', R⁷, R⁶, X⁴, R⁵, X³, R⁴, R⁴', R³, R² and N atoms]

| | | | |
|---|---|---|---|
| 36.1 | —CH₃ | H | H |

TABLE 3

Substituted 2,5-diaminoterephthalic acid dinitriles

| Substrate | | R³ | R² |
|---|---|---|---|
| [Core structure with CN, R², R³, R⁴, R⁶, R⁷, R⁸ substituents] | 3.0 | | |
| [NC-phenyl-NH-benzene(CN)₂-NH-phenyl-CN structure] | 3.1 | [4-cyanophenyl] | H |
| [bis(2-fluoro-N-methylphenylamino) benzene dinitrile] | 3.2 | [2-fluorophenyl] | —CH₃ |
| [bis(2-fluorophenylamino) benzene dinitrile] | 3.3 | [2-fluorophenyl] | H |

TABLE 3-continued
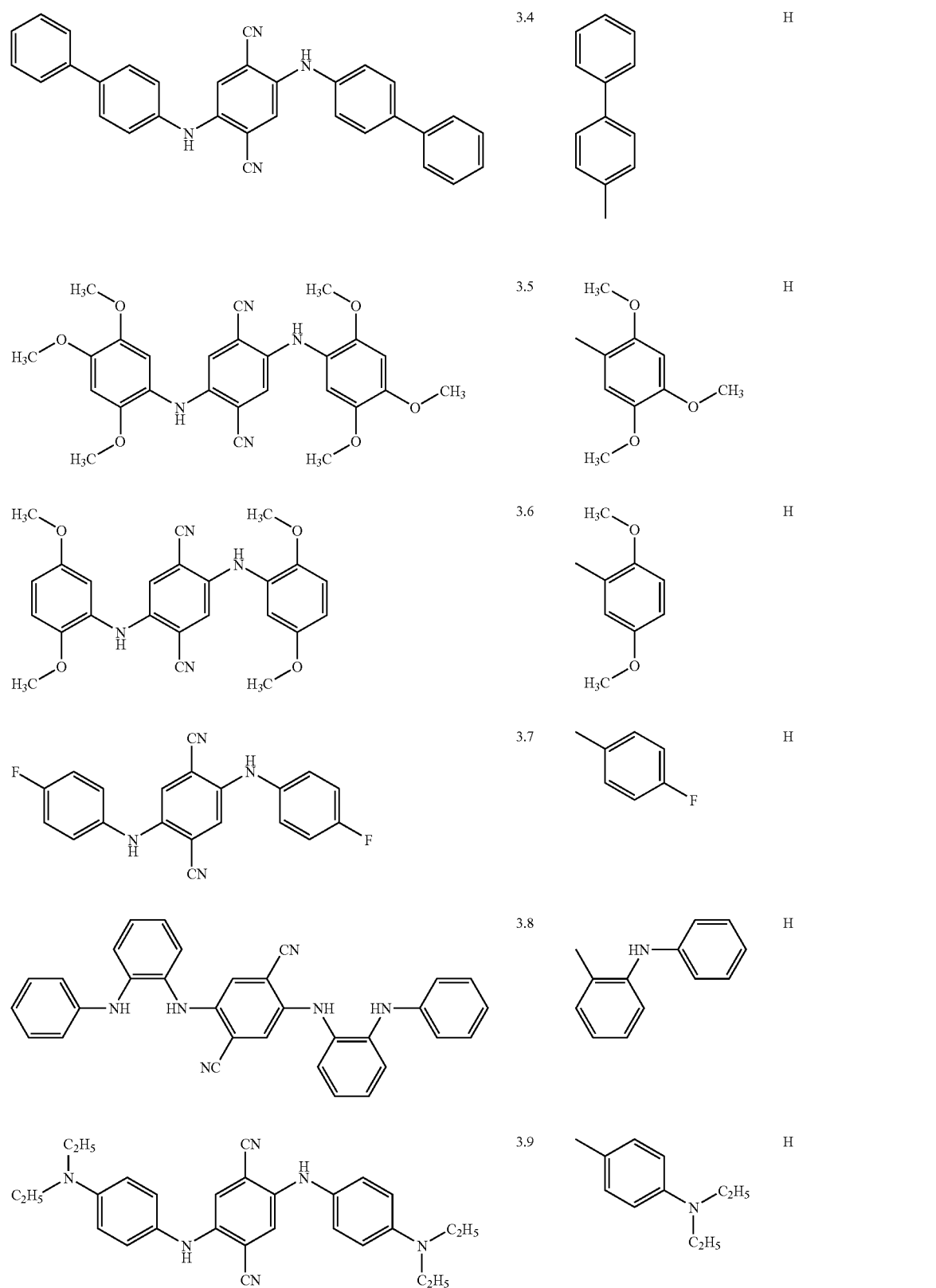

TABLE 3-continued

| | | | |
|---|---|---|---|
| [structure: 1,4-bis(4-ethylanilino)-2,5-dicyanobenzene] | 3.10 | [4-ethylphenyl] | H |
| [structure: 1,4-bis(3-fluoroanilino)-2,5-dicyanobenzene] | 3.11 | [3-fluorophenyl] | H |
| [structure: 1,4-bis(3-cyanoanilino)-2,5-dicyanobenzene] | 3.12 | [3-cyanophenyl] | H |
| [structure: 1,4-bis(2-cyanoanilino)-2,5-dicyanobenzene] | 3.13 | [2-cyanophenyl] | H |
| [structure: 1,4-bis(4-methoxyanilino)-2,5-dicyanobenzene] | 3.14 | [4-methoxyphenyl] | H |
| [structure: 1,4-bis(2,4-dimethoxyanilino)-2,5-dicyanobenzene] | 3.15 | [2,4-dimethoxyphenyl] | H |
| [structure: 1,4-dianilino-2,5-dicyanobenzene] | 3.16 | [phenyl] | H |

TABLE 3-continued

| Structure | # | R | R' |
|---|---|---|---|
| (structure with two CN, two N(CH₃)(phenyl) groups) | 3.17 | (phenyl) | —CH₃ |
| (structure with two CN, two NH-pyrenyl groups) | 3.18 | (pyrenyl) | H |
| (structure with two CN, two NH-C₆H₄-N(CH₃)₂ groups) | 3.19 | (4-(dimethylamino)phenyl) | H |
| (structure with two CN, two NH-(2,5-diethoxy-4-morpholinophenyl) groups) | 3.20 | (2,5-diethoxy-4-morpholinophenyl) | H |
| (structure with two CN, two NH-benzodioxolyl groups) | 3.21 | (benzo[1,3]dioxol-5-yl) | H |
| (structure with two CN, two NH-C₄H₉ groups) | 3.22 | —C₄H₉ | H |
| (structure with two CN, two NH-CH₂CH₂OCH₃ groups) | 3.23 | —CH₂CH₂OCH₃ | H |

TABLE 3-continued

| Structure | # | R | R' |
|---|---|---|---|
| (structure) | 3.24 | 3,4,5-trimethoxyphenyl | H |
| (structure) | 3.25 | 2,4,6-trimethylphenyl (mesityl) | H |
| (structure) | 3.26 | 2,5-dimethoxyphenyl | —CH₃ |
| (structure) | 3.27 | cyclohexyl | H |
| (structure) | 3.28 | 3-fluorophenyl | —CH₃ |
| (structure) | 3.29 | 2,4-dimethoxyphenyl | —CH₃ |
| (structure) | 3.30 | 4-fluorophenyl | —CH₃ |

TABLE 3-continued
| | | | | |
|---|---|---|---|---|
| 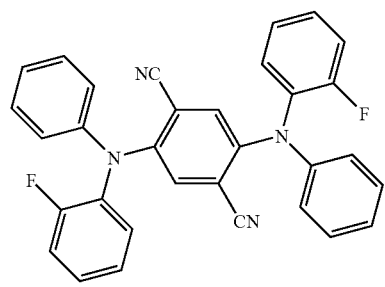 | | 3.31 | 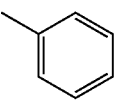 | 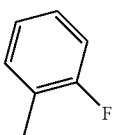 |
| 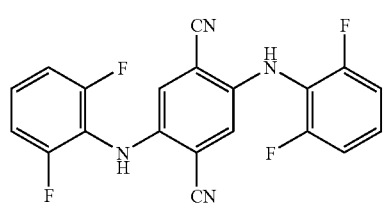 | | 3.32 | 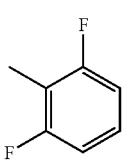 | H |
| 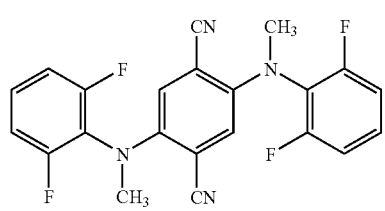 | | 3.33 | 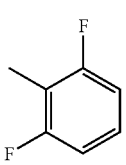 | —CH₃ |
| 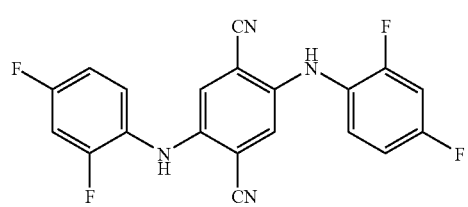 | | 3.34 |  | H |
| 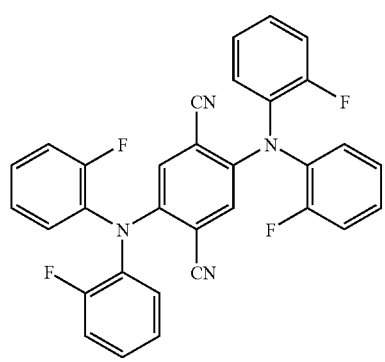 | | 3.35 | 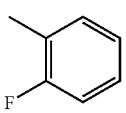 | 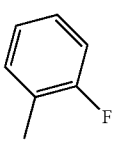 |
| 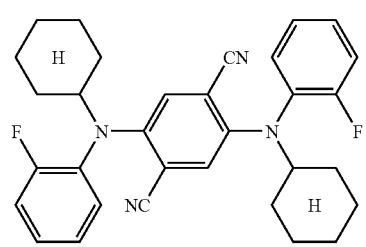 | | 3.36 | 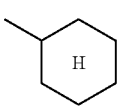 | 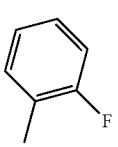 |

TABLE 3-continued
| | | | |
|---|---|---|---|
| | 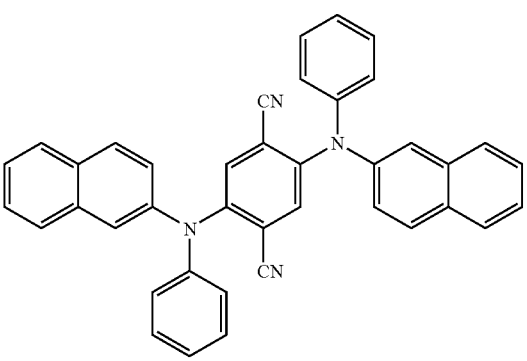 | 3.37 | 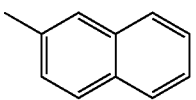 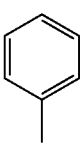 |
| | 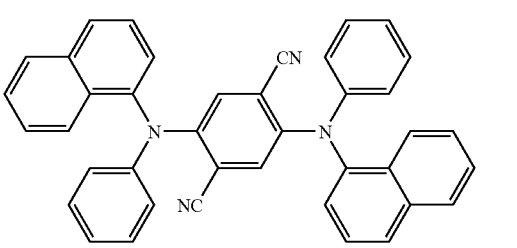 | 3.38 | 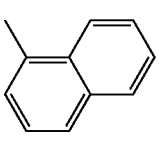 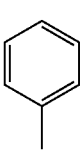 |
| | 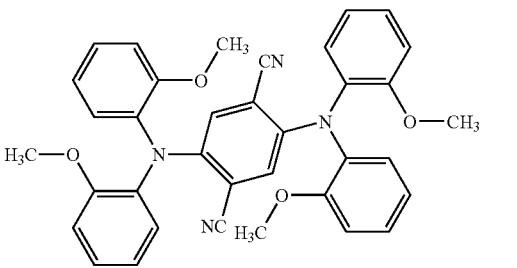 | 3.39 | 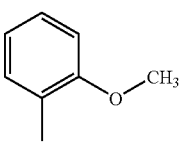 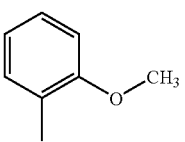 |
| | 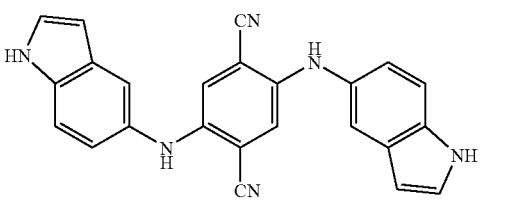 | 3.40 | 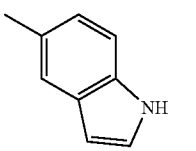 H |
| | | 3.41 |  —CH$_3$ |
| | | 3.42 | 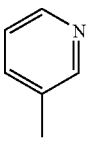 —CH$_3$ |

TABLE 3-continued
| | | |
|---|---|---|
| 3.43 | 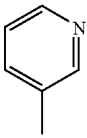 | —CH₃ |
| 3.44 | 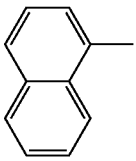 | —CH₃ |
| 3.45 |  | —CH₃ |
| 3.46 | 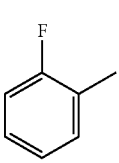 | —CH₃ |
| 3.47 | 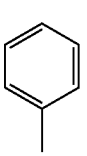 | —CF₃ |
| 3.48 | 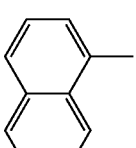 | —CF₃ |
| 3.49 |  | —CF₃ |
| 3.50 | 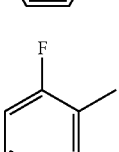 | —CF₃ |
| 3.51 | 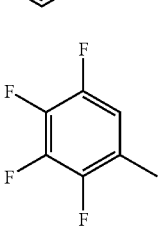 | —CF₃ |

TABLE 3-continued
| | | |
|---|---|---|
| 3.52 | 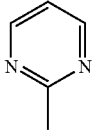 | —CF$_3$ |
| 3.53 | 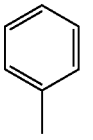 | 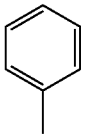 |
| 3.54 | 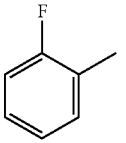 | 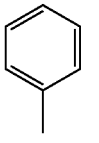 |
| 3.55 | 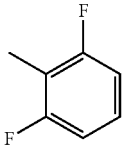 | 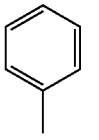 |
| 3.56 | 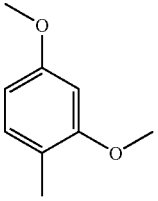 | 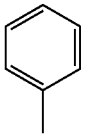 |
| 3.57 | 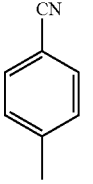 | 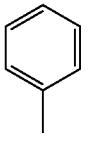 |
| 3.58 |  | 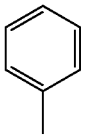 |
| 3.59 | 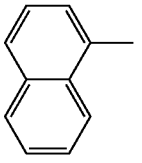 | 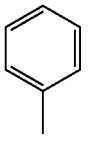 |
| 3.60 |  | 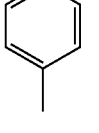 |

TABLE 3-continued
| | | |
|---|---|---|
| 3.61 | 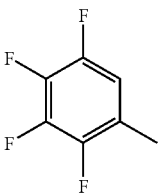 | 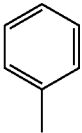 |
| 3.62 | 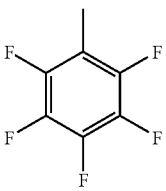 | —CH₃ |
| 3.63 | 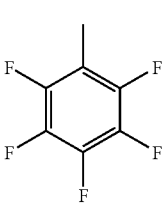 | 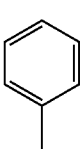 |
| 3.64 | 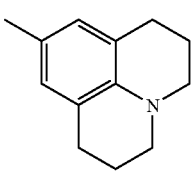 | 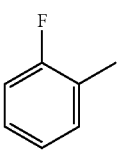 |
| 3.65 | 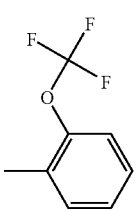 | 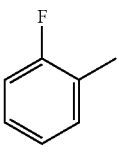 |
| 3.66 | 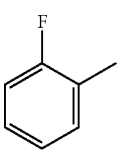 | 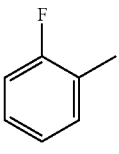 |
| 3.67 | 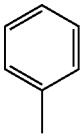 | H |
| 3.68 | 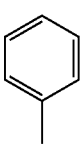 | 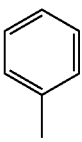 |
| 3.69 | 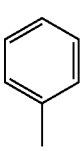 | —CH₃ |

TABLE 3-continued

| | | R⁴ | R⁸ | R⁶ |
|---|---|---|---|---|
| 3.70 | (phenyl, phenyl) | | | |
| 3.71 | (phenyl, 2-fluorophenyl) | | | |
| 3.0 (core structure) | | | | |
| 3.1 | | H | H | H |
| 3.2 | | H | H | —CH₃ |
| 3.3 | | H | H | H |
| 3.4 | | H | H | H |

TABLE 3-continued
| Structure | # | | | |
|---|---|---|---|---|
| 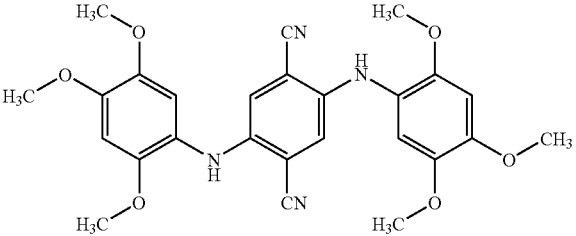 | 3.5 | H | H | H |
| 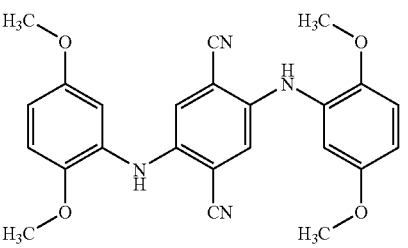 | 3.6 | H | H | H |
| 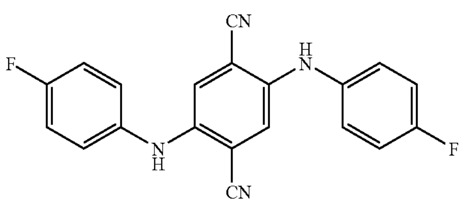 | 3.7 | H | H | H |
| 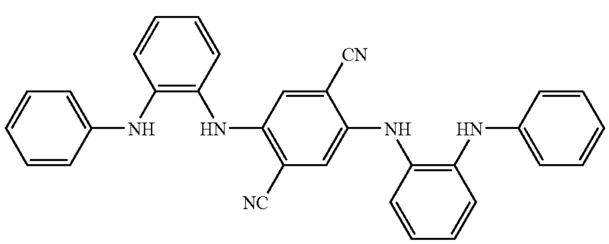 | 3.8 | H | H | H |
| 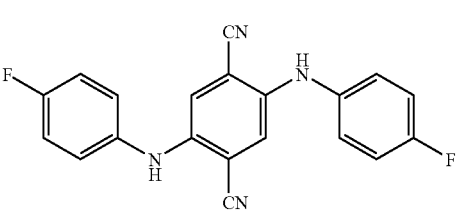 | 3.9 | H | H | H |
| 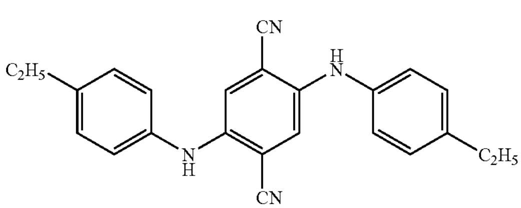 | 3.10 | H | H | H |
| 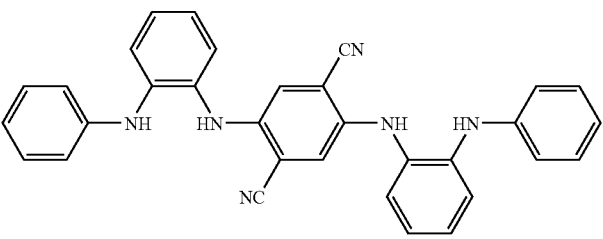 | 3.11 | H | H | H |

TABLE 3-continued

| Structure | # | | | |
|---|---|---|---|---|
| [structure with two 3-cyanophenylamino groups on dicyanobenzene] | 3.12 | H | H | H |
| [structure with two 2-cyanophenylamino groups on dicyanobenzene] | 3.13 | H | H | H |
| [structure with two 4-methoxyphenylamino groups on dicyanobenzene] | 3.14 | H | H | H |
| [structure with two 2,4-dimethoxyphenylamino groups on dicyanobenzene] | 3.15 | H | H | H |
| [structure with two phenylamino groups on dicyanobenzene] | 3.16 | H | H | H |
| [structure with two N-methyl-N-phenylamino groups on dicyanobenzene] | 3.17 | H | H | —CH₃ |
| [structure with two pyrenylamino groups on dicyanobenzene] | 3.18 | H | H | H |

TABLE 3-continued
| Structure | # | | | |
|---|---|---|---|---|
| 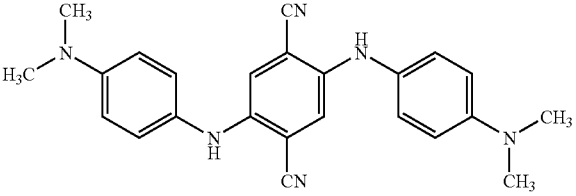 | 3.19 | H | H | H |
| 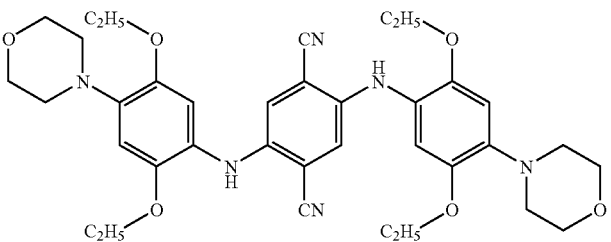 | 3.20 | H | H | H |
| 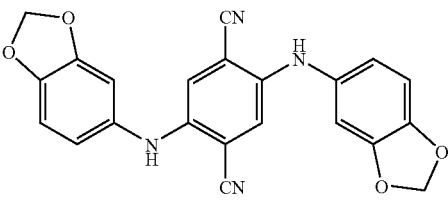 | 3.21 | H | H | H |
| 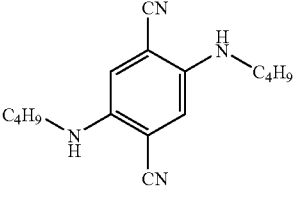 | 3.22 | H | H | H |
| 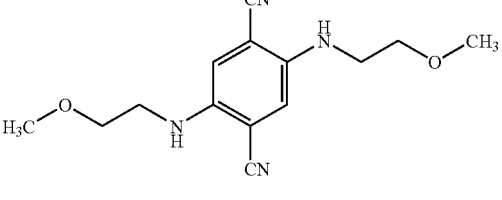 | 3.23 | H | H | H |
| 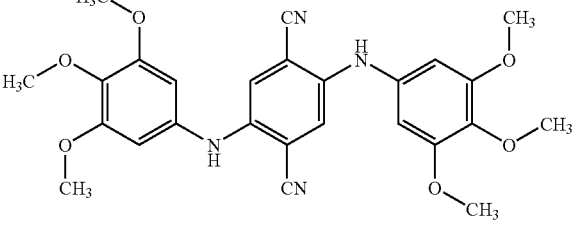 | 3.24 | H | H | H |
| 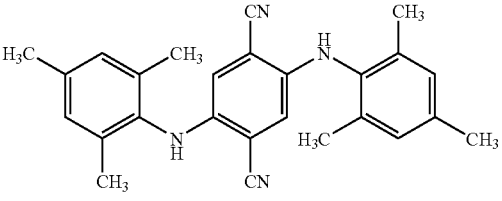 | 3.25 | H | H | H |

TABLE 3-continued

| Structure | # | | | |
|---|---|---|---|---|
| (2,5-dimethoxyphenyl-N-methyl)... dicyano benzene | 3.26 | H | H | —CH₃ |
| dicyclohexylamino dicyano benzene | 3.27 | H | H | H |
| bis(3-fluorophenyl-N-methyl) dicyano benzene | 3.28 | H | H | —CH₃ |
| bis(2,4-dimethoxyphenyl-N-methyl) dicyano benzene | 3.29 | H | H | —CH₃ |
| bis(4-fluorophenyl-N-methyl) dicyano benzene | 3.30 | H | H | —CH₃ |
| bis(phenyl-2-fluorophenyl-amino) dicyano benzene | 3.31 | H | H | 2-fluorotoluene |
| bis(2,6-difluorophenylamino) dicyano benzene | 3.32 | H | H | H |

TABLE 3-continued
| Structure | No. | | | |
|---|---|---|---|---|
| 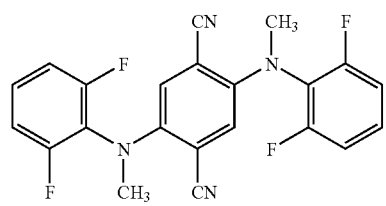 | 3.33 | H | H | —CH₃ |
| 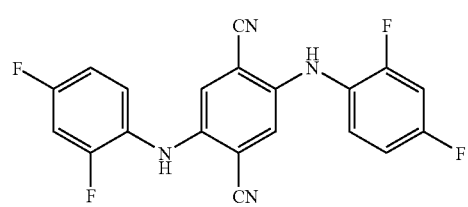 | 3.34 | H | H | H |
| 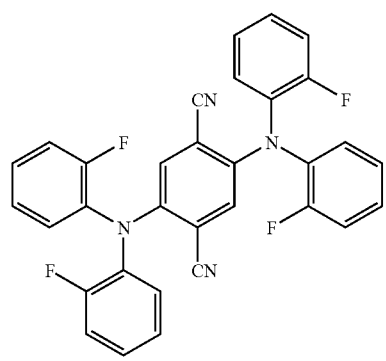 | 3.35 | H | H |  |
| 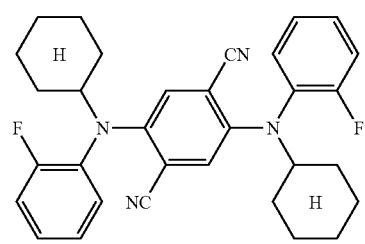 | 3.36 | H | H |  |
| 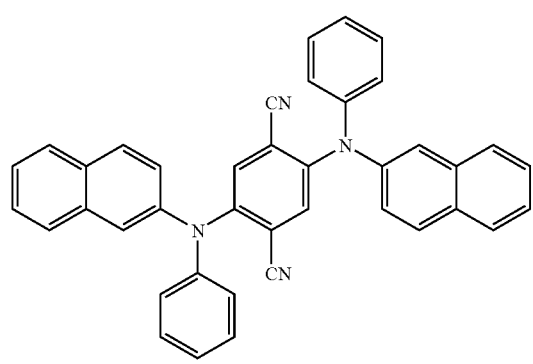 | 3.37 | H | H | 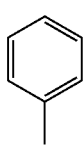 |

TABLE 3-continued

| | | | |
|---|---|---|---|
| | 3.38 | H | H | (phenyl) |
| | 3.39 | H | H | (2-methoxyphenyl) |
| | 3.40 | H | H | H |
| | 3.41 | H | H | —CH₃ |
| | 3.42 | H | H | —CH₃ |
| | 3.43 | H | H | —CH₃ |
| | 3.44 | H | H | —CH₃ |
| | 3.45 | H | H | —CH₃ |
| | 3.46 | H | H | —CH₃ |
| | 3.47 | H | H | —CF₃ |
| | 3.48 | H | H | —CF₃ |
| | 3.49 | H | H | —CF₃ |
| | 3.50 | H | H | —CF₃ |
| | 3.51 | H | H | —CF₃ |
| | 3.52 | H | H | —CF₃ |
| | 3.53 | H | H | (phenyl) |
| | 3.54 | H | H | (phenyl) |
| | 3.55 | H | H | (phenyl) |
| | 3.56 | H | H | (phenyl) |

TABLE 3-continued

| | | | |
|---|---|---|---|
| 3.57 | H | H | phenyl |
| 3.58 | H | H | phenyl |
| 3.59 | H | H | phenyl |
| 3.60 | H | H | phenyl |
| 3.61 | H | H | phenyl |
| 3.62 | H | H | —CH₃ |
| 3.63 | H | H | phenyl |
| 3.64 | H | H | 2-fluorophenyl |
| 3.65 | H | H | 2-fluorophenyl |
| 3.66 | H | H | 2-fluorophenyl |
| 3.67 | H | H | H |
| 3.68 | H | H | phenyl |

TABLE 3-continued
| | | | R7 |
|---|---|---|---|
| 3.69 | 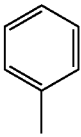 | 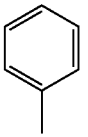 | —CH3 |
| 3.70 | 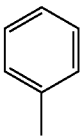 | 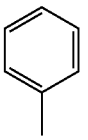 | 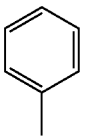 |
| 3.71 | 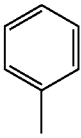 | 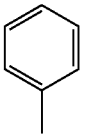 | 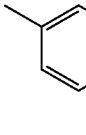 |
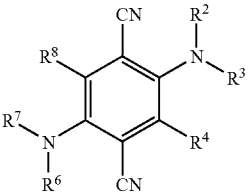
| | | R7 |
|---|---|---|
| 3.0 | | |
| 3.1 | 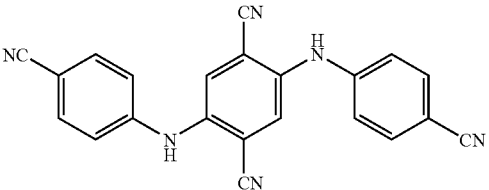 | 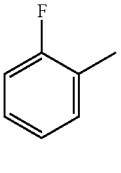 |
| 3.2 | 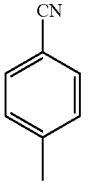 | 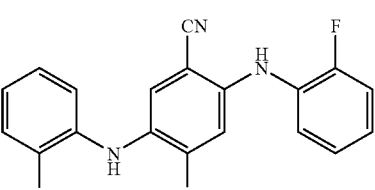 |
| 3.3 | 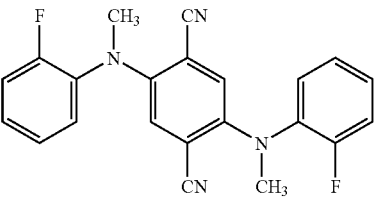 | 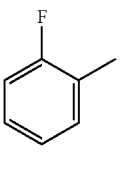 |
| 3.4 | 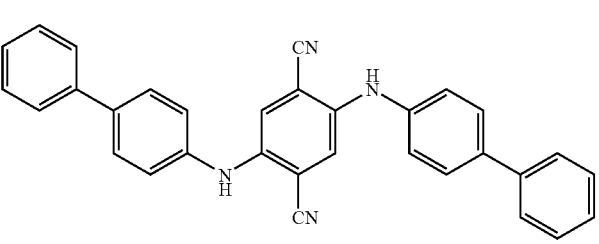 | 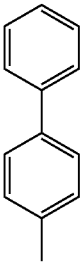 |

TABLE 3-continued
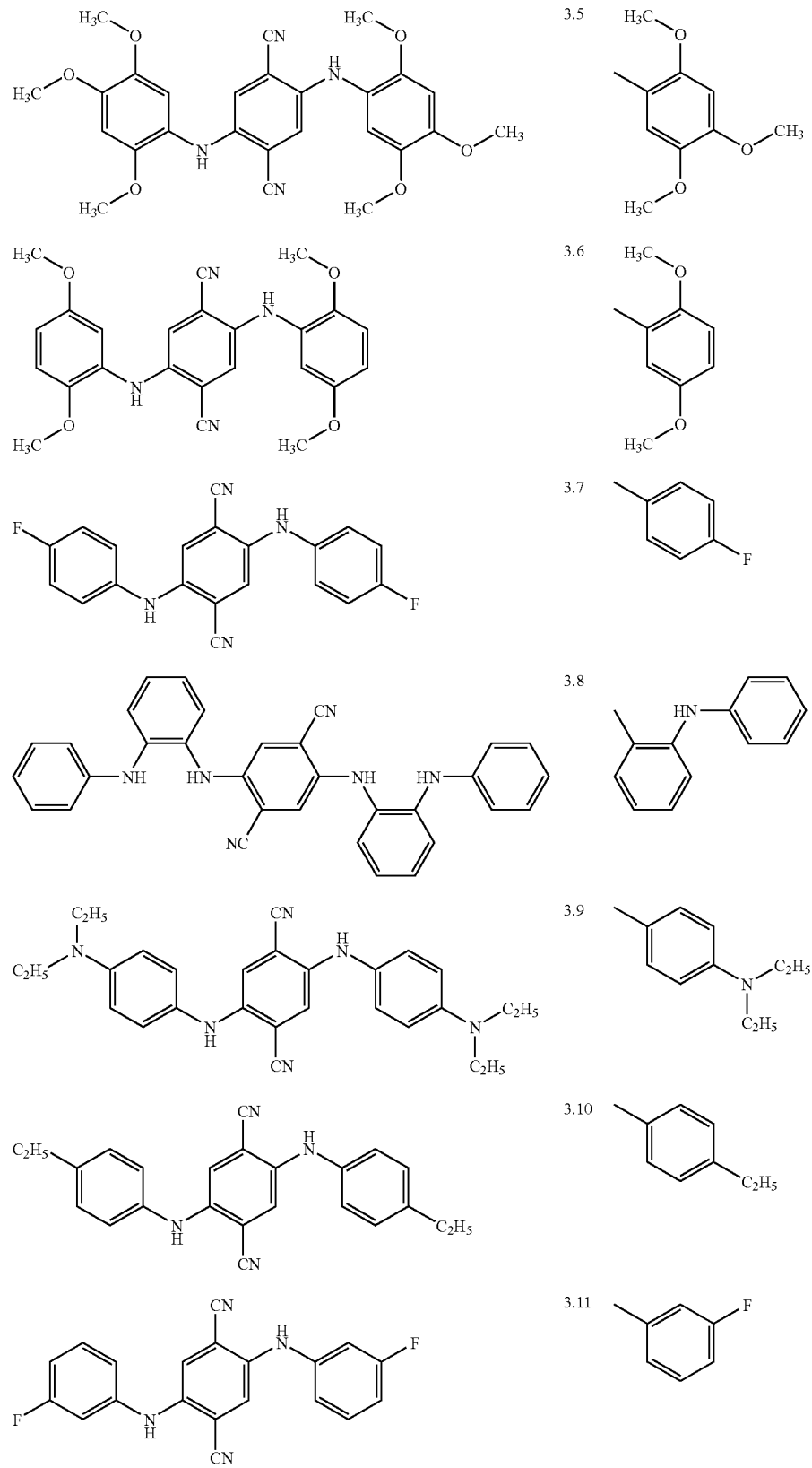

TABLE 3-continued
| | |
|---|---|
| 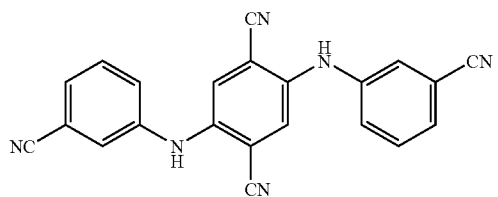 | 3.12 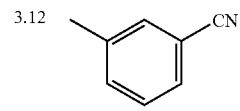 |
| 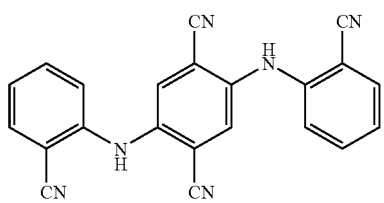 | 3.13 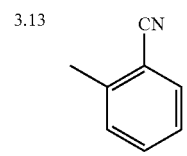 |
| 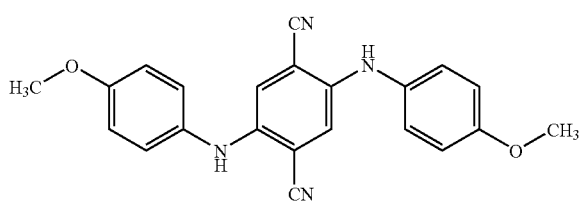 | 3.14 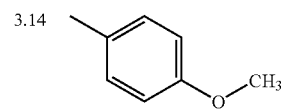 |
| 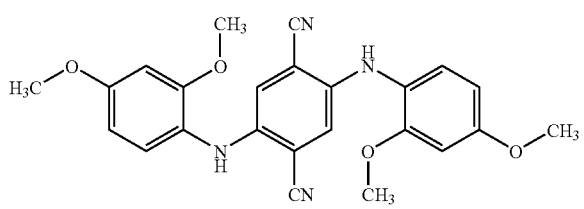 | 3.15 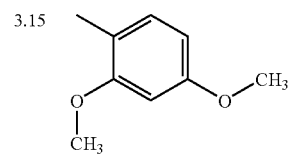 |
| 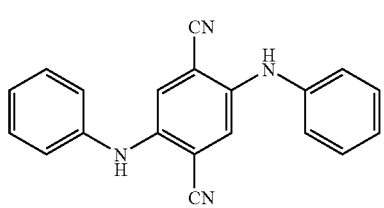 | 3.16 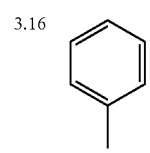 |
| 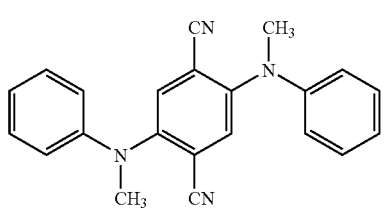 | 3.17 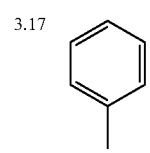 |
| 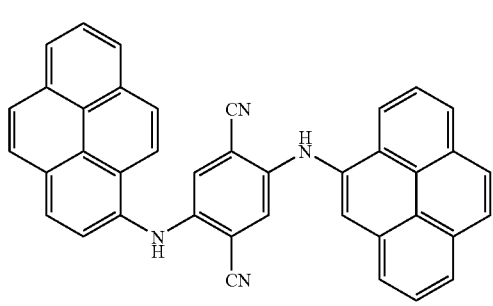 | 3.18 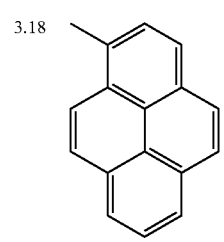 |

TABLE 3-continued
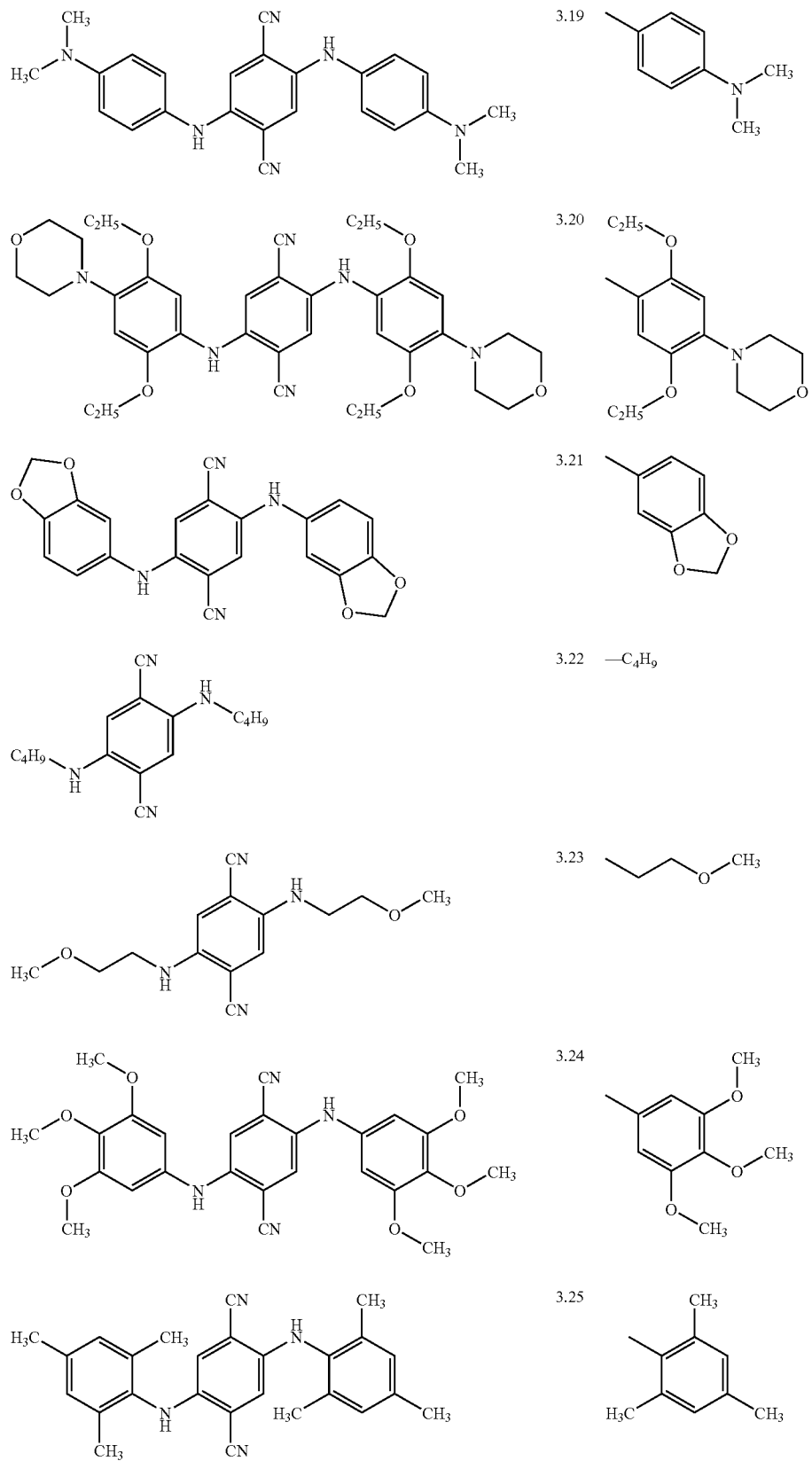

TABLE 3-continued
| | |
|---|---|
| 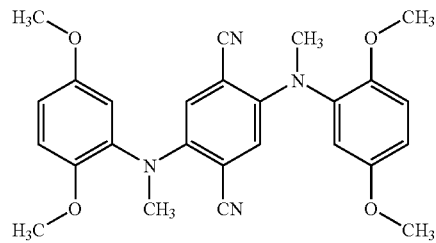 | 3.26 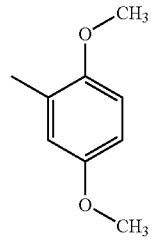 |
| 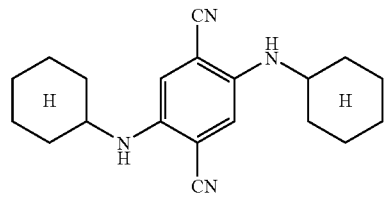 | 3.27 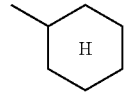 |
| 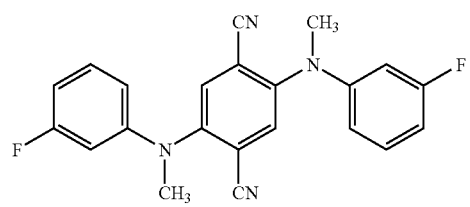 | 3.28 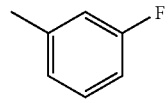 |
| 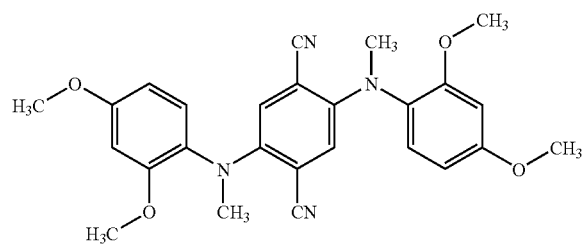 | 3.29 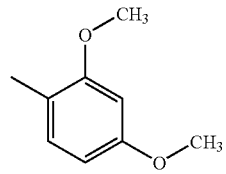 |
| 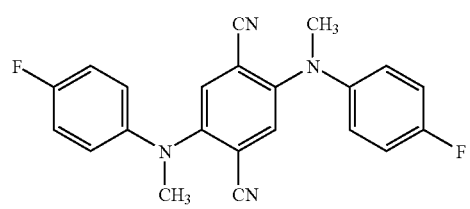 | 3.30 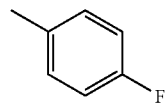 |
| 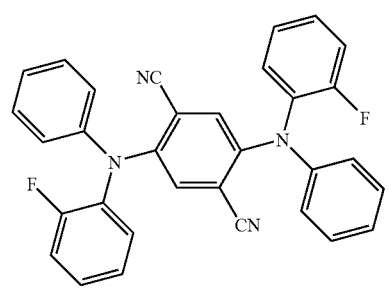 | 3.31 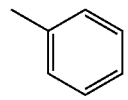 |
| 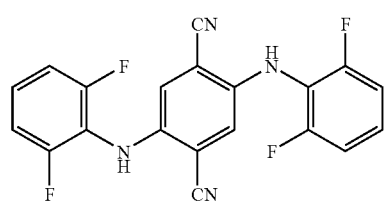 | 3.32 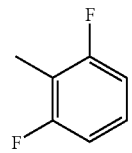 |

TABLE 3-continued
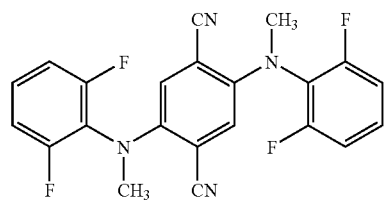 | 3.33 | 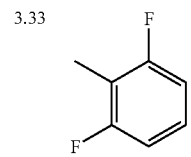
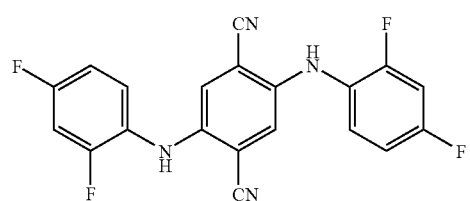 | 3.34 | 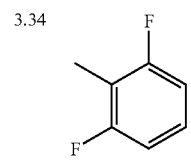
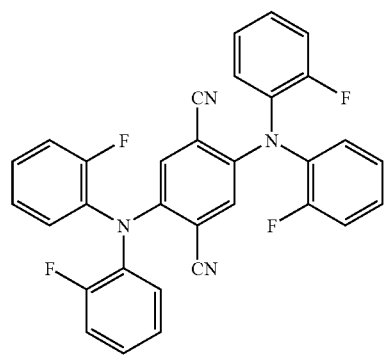 | 3.35 | 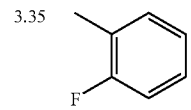
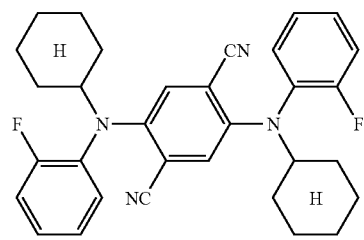 | 3.36 | 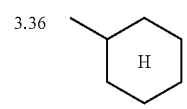
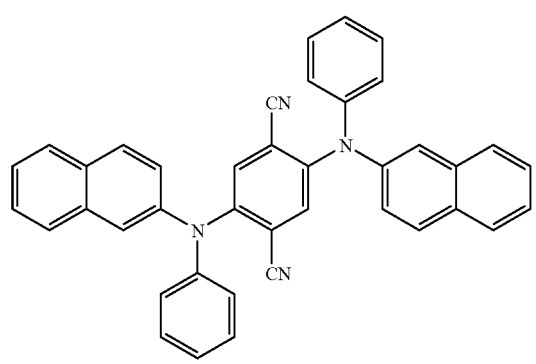 | 3.37 | 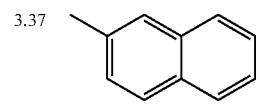

TABLE 3-continued
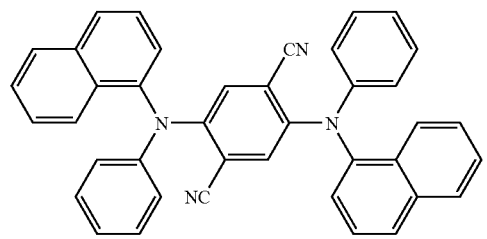 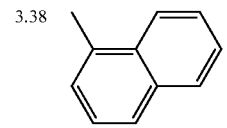
3.38
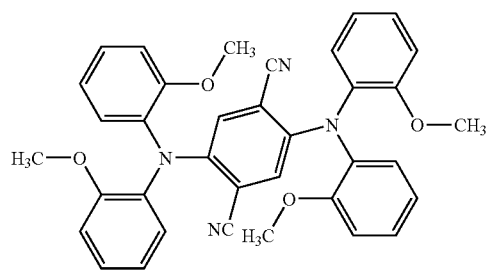 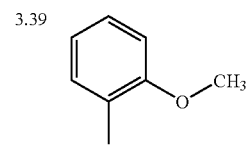
3.39
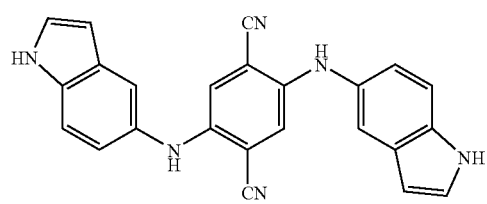 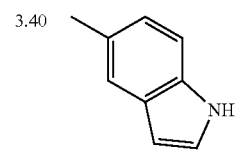
3.40
3.41 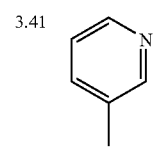
3.42 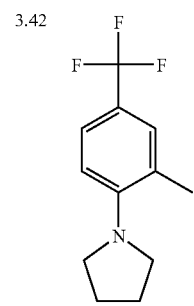
3.43 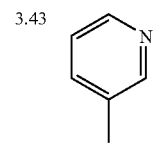
3.44 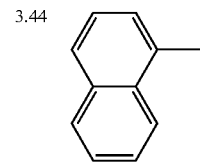

TABLE 3-continued

| | |
|---|---|
| 3.45 | 2-methylnaphthalene |
| 3.46 | 2-fluoro-6-methylbenzene |
| 3.47 | methylbenzene |
| 3.48 | 1-methylnaphthalene |
| 3.49 | 2-methylnaphthalene |
| 3.50 | 2-fluoro-methylbenzene |
| 3.51 | 2,3,4,5-tetrafluoro-6-methylbenzene |
| 3.52 | 2-methylpyrimidine |
| 3.53 | methylbenzene |

TABLE 3-continued
| | |
|---|---|
| 3.54 | 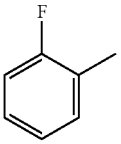 |
| 3.55 | 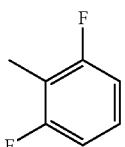 |
| 3.56 | 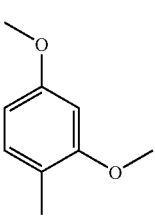 |
| 3.57 | 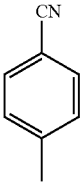 |
| 3.58 | 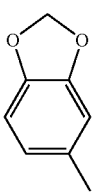 |
| 3.59 | 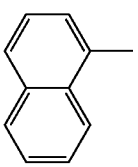 |
| 3.60 | 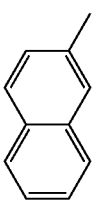 |
| 3.61 | 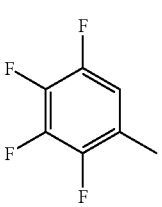 |

TABLE 3-continued
3.62 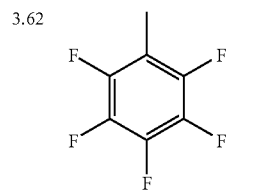
3.63 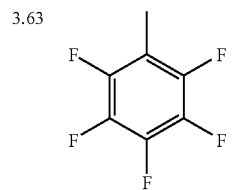
3.64 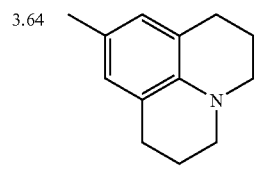
3.65 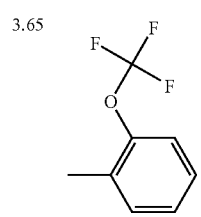
3.66 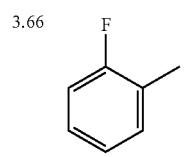
3.67 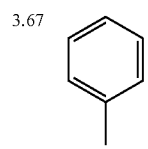
3.68 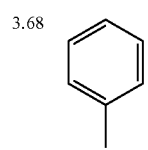
3.69 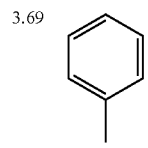
3.70 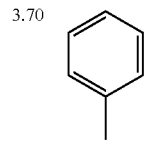

TABLE 3-continued
| | | | | | 3.71 | 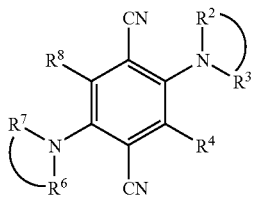 |
| Substance | | R² | R³ | R⁴ | R⁶ | R⁷ | R⁸ |
|---|---|---|---|---|---|---|---|
| 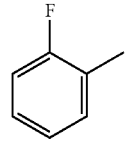 | 48.0 | | | | | | |
| | 48.1 | 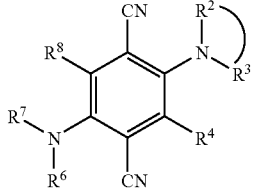 | H | | | 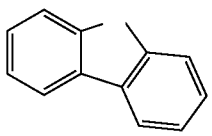 | H |
| | 48.2 | 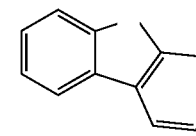 | H | | | 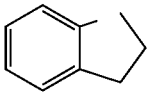 | H |
| | 48.3 | 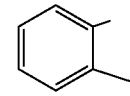 | H | | | 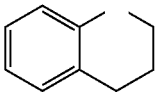 | H |
| | 48.4 | 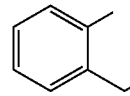 | H | | | 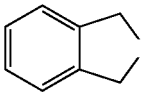 | H |
| 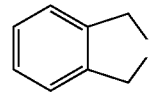 | 44.0 | | | | | | |
| | 44.1 | 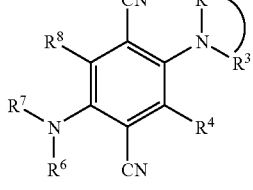 | H | | —CH₃ | 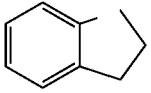 | H |
| | 44.2 |  | H | | 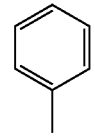 | 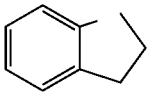 | H |
| | 44.3 | 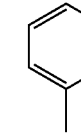 | 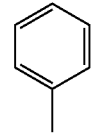 | | 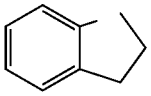 | 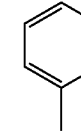 | H |

TABLE 3-continued
| Substance | | R⁸ | R² | R³ | R⁶ | R⁷ | R⁴ |
|---|---|---|---|---|---|---|---|
| 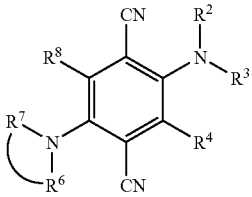 | 46.0 | | | | | | |
| | 46.1 | H | —CH₃ | 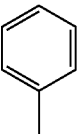 | | 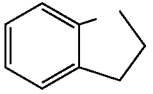 | H |
| | 46.2 | H | 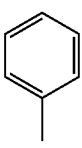 | 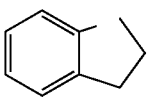 | | 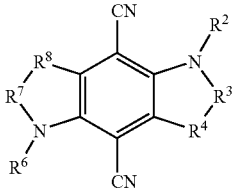 | H |
| Substance | | R⁴ | R³ | R² | R⁸ | R⁷ | R⁶ |
|---|---|---|---|---|---|---|---|
| 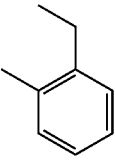 | 49.0 | | | | | | |
| | 49.1 | 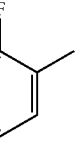 | 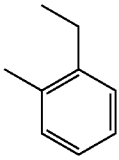 | | 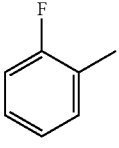 | 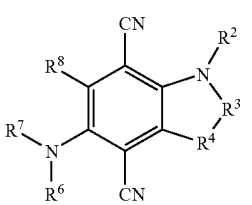 | |
| 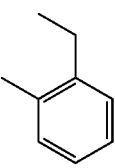 | 45.0 | | | | | | |
| | 45.1 | 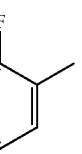 | 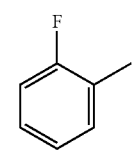 | H | 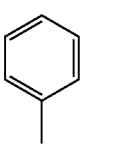 | 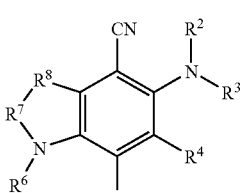 | |
| | 47.0 | | | | | | |

TABLE 3-continued

| 47.1 | H | [2-fluorophenyl] | [2-fluorophenyl] | [2-ethylphenyl] |

TABLE 4

Substituted 2,5-diamino-3,6-dihydroterephthalic acid dinitriles

| Substance | | R³ | R² | R⁴ | R⁴' | R⁸ | R⁸' | R⁶ |
|---|---|---|---|---|---|---|---|---|
| [structure with R², R³, R⁴, R⁴', R⁶, R⁷, R⁸, R⁸' substituents on dihydroterephthalic dinitrile core] | 4.0 | | | —CH₃ | —CH₃ | —CH₃ | —CH₃ | |
| [structure with 4-cyanophenylamino groups] | 4.1 | [4-cyanophenyl] | H | —CH₃ | —CH₃ | —CH₃ | —CH₃ | H |
| [structure with N-methyl-2-fluoroanilino groups] | 4.2 | [2-fluorophenyl] | —CH₃ | —CH₃ | —CH₃ | —CH₃ | —CH₃ | —CH₃ |
| [structure with 2-fluoroanilino groups] | 4.3 | [2-fluorophenyl] | H | —CH₃ | —CH₃ | —CH₃ | —CH₃ | H |

| Substance | | R⁷ |
|---|---|---|
| [structure with R², R³, R⁴, R⁴', R⁶, R⁷, R⁸, R⁸' substituents on dihydroterephthalic dinitrile core] | 4.0 | |
| [structure with 4-cyanophenylamino groups] | 4.1 | [4-cyanophenyl] |

TABLE 4-continued
| | | | |
|---|---|---|---|
| | 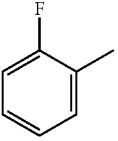 | 4.2 | 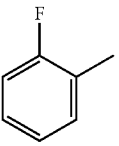 |
| | 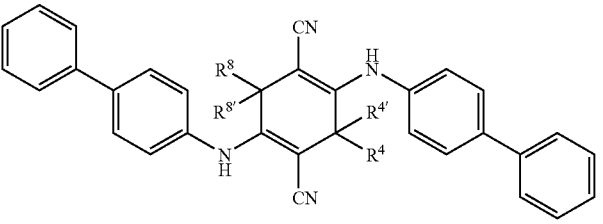 | 4.3 | 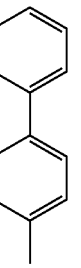 |
| Substance | | R³ | R² |
|---|---|---|---|
| 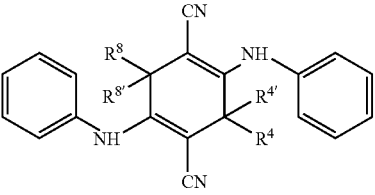 | 4.4 | 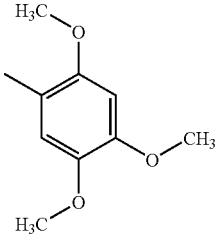 | H |
| 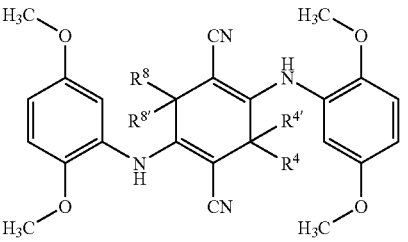 | 4.5 | 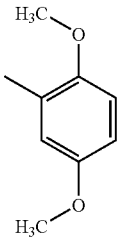 | H |
| 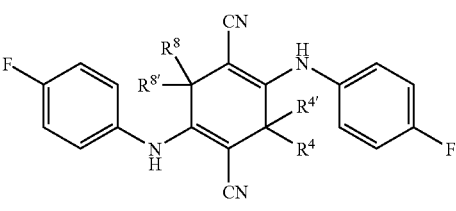 | 4.6 | 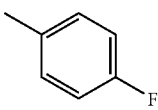 | H |
| | 4.7 | | H |

TABLE 4-continued
| Structure | # | R group | H |
|---|---|---|---|
| 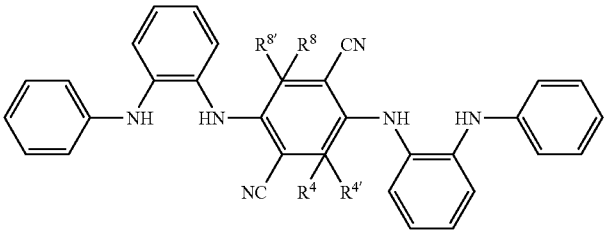 | 4.8 | 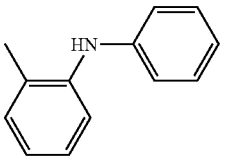 | H |
| 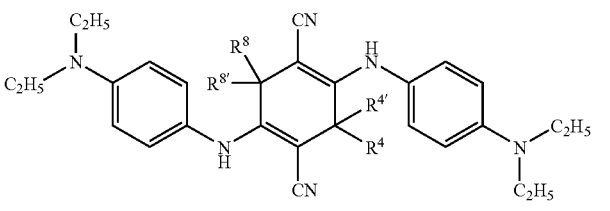 | 4.9 | 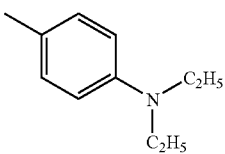 | H |
| 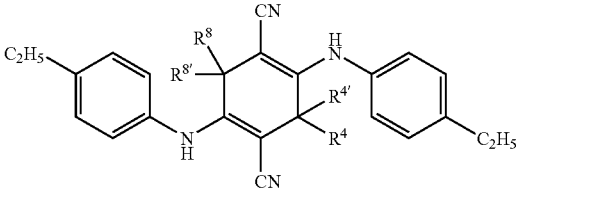 | 4.10 | 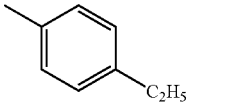 | H |
| 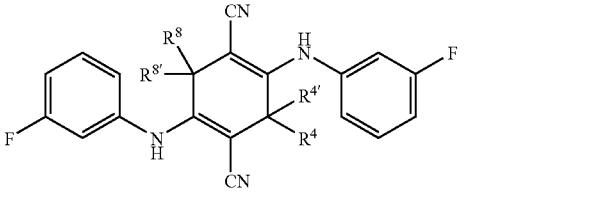 | 4.11 | 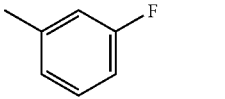 | H |
| 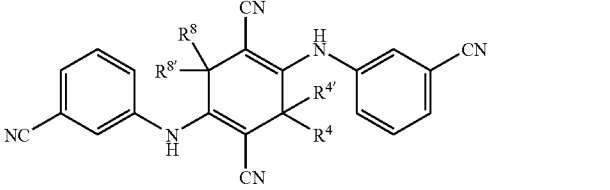 | 4.12 | 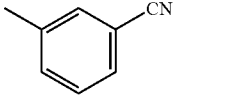 | H |
| 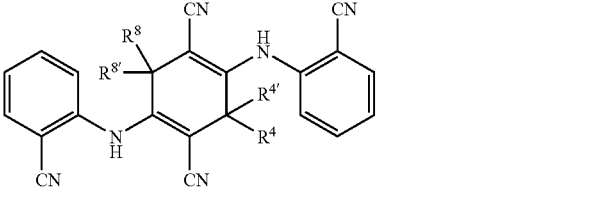 | 4.13 | 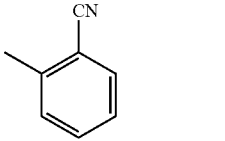 | H |
| 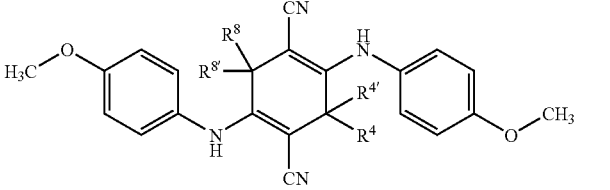 | 4.14 | 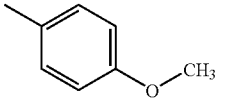 | H |

TABLE 4-continued

| | | | |
|---|---|---|---|
| (structure) | 4.15 | (2,4-dimethoxyphenyl-methyl) | H |
| (structure) | 4.16 | (phenyl) | H |
| (structure) | 4.17 | (phenyl) | —CH₃ |
| (structure) | 4.18 | (pyrenyl) | H |
| (structure) | 4.19 | (4-dimethylaminophenyl-methyl) | H |
| (structure) | 4.20 | (ethoxy-methyl-morpholinophenyl) | H |

TABLE 4-continued

| Structure | # | R | R' |
|---|---|---|---|
| (benzodioxole-NH substituted cyclohexadiene with CN, R8, R8', R4, R4' groups) | 4.21 | (methyl-benzodioxole) | H |
| (C4H9-NH substituted cyclohexadiene with CN, R8, R8', R4, R4' groups) | 4.22 | —C4H9 | H |
| (methoxyethyl-NH substituted cyclohexadiene with CN, R8, R8', R4, R4' groups) | 4.23 | (CH2CH2OCH3) | H |
| (trimethoxyphenyl-NH substituted cyclohexadiene with CN, R8, R8', R4, R4' groups) | 4.24 | (3,4,5-trimethoxyphenyl) | H |
| (trimethylphenyl-NH substituted cyclohexadiene with CN, R8, R8', R4, R4' groups) | 4.25 | (2,4,6-trimethylphenyl) | H |
| (dimethoxyphenyl-N(CH3) substituted cyclohexadiene with CN, R8, R8', R4, R4' groups) | 4.26 | (2,5-dimethoxyphenyl) | —CH3 |
| (cyclohexyl-NH substituted cyclohexadiene with CN, R8, R8', R4, R4' groups) | 4.27 | (cyclohexyl) | H |

TABLE 4-continued

| Structure | # | Ar | R |
|---|---|---|---|
| (structure with two 3-fluorophenyl N-CH3 groups, CN, R8, R8', R4, R4') | 4.28 | 3-fluorotolyl | —CH3 |
| (structure with two 2,4-dimethoxyphenyl N-CH3 groups, CN, R8, R8', R4, R4') | 4.29 | 2,4-dimethoxytolyl | —CH3 |
| (structure with two 4-fluorophenyl N-CH3 groups, CN, R8, R8', R4, R4') | 4.30 | 4-fluorotolyl | —CH3 |
| (structure with two N(2-fluorophenyl)(phenyl) groups, CN, R8, R8', R4, R4') | 4.31 | tolyl | 2-fluorotolyl |
| (structure with two 2,6-difluorophenyl NH groups, CN, R8, R8', R4, R4') | | 2,6-difluorotolyl | H |
| (structure with two 2,6-difluorophenyl N-CH3 groups, CN, R8, R8', R4, R4') | 4.32 | 2,6-difluorotolyl | —CH3 |

TABLE 4-continued
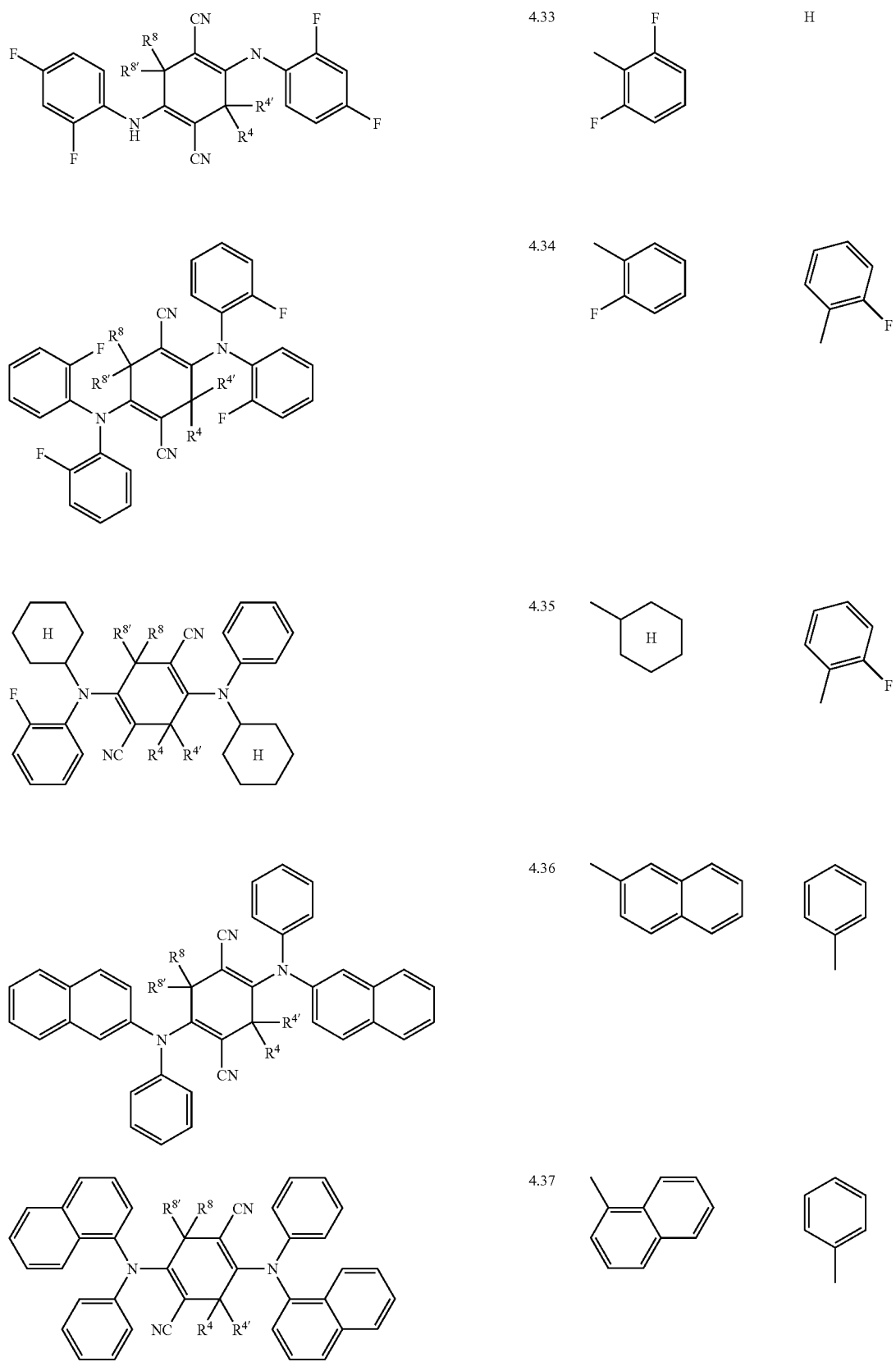

TABLE 4-continued
| | | | |
|---|---|---|---|
| | 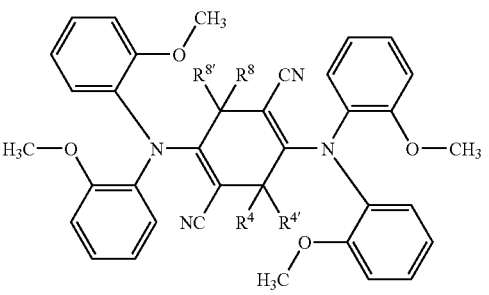 | 4.38 | 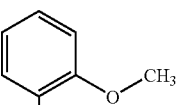 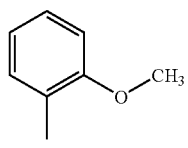 |
| | 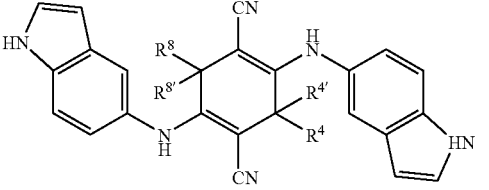 | 4.38 | 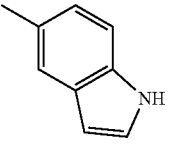 H |
| | | 4.40 | 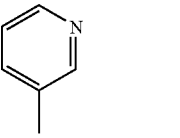 —CH₃ |
| | | 4.41 | 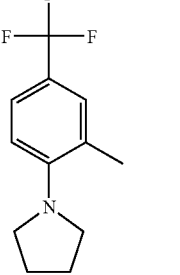 —CH₃ |
| | | 4.42 | 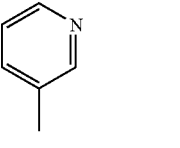 —CH₃ |
| | | 4.43 | 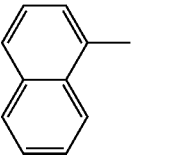 —CH₃ |
| | | 4.44 | 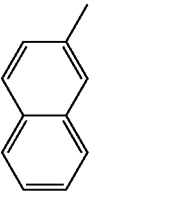 —CH₃ |

TABLE 4-continued
| | | |
|---|---|---|
| 4.45 | 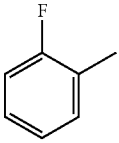 | —CH₃ |
| 4.46 | 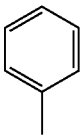 | —CF₃ |
| 4.47 | 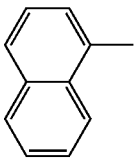 | —CF₃ |
| 4.48 | 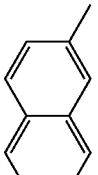 | —CF₃ |
| 4.49 | 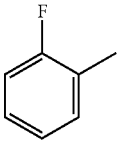 | —CF₃ |
| 4.50 | 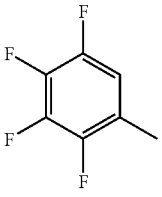 | —CF₃ |
| 4.51 | 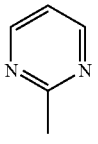 | —CF₃ |
| 4.52 | 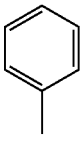 | 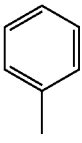 |
| 4.53 | 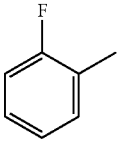 | 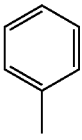 |

TABLE 4-continued

| | | |
|---|---|---|
| 4.54 | 2-fluorotoluene | phenyl |
| 4.55 | 2,5-dimethoxytoluene | phenyl |
| 4.56 | 4-cyanotoluene | phenyl |
| 4.57 | 5-methyl-benzo[1,3]dioxole | phenyl |
| 4.58 | 1-methylnaphthalene | phenyl |
| 4.59 | 2-methylnaphthalene | phenyl |
| 4.60 | 2,3,4,5-tetrafluorotoluene | phenyl |
| 4.61 | pentafluorotoluene | —CH₃ |

TABLE 4-continued
| | | | |
|---|---|---|---|
| | 4.62 | 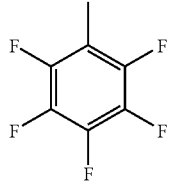 | 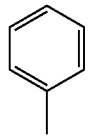 |
| | 4.63 | 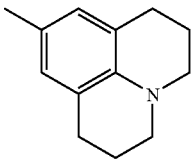 | 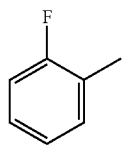 |
| | 4.64 | 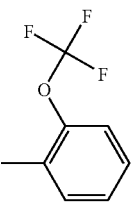 | 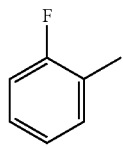 |
| | 4.65 | 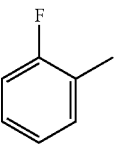 | 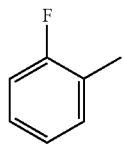 |
| | 4.66 | 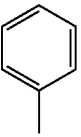 | H |
| | 4.67 | 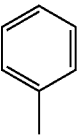 | 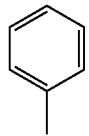 |
| | 4.68 | 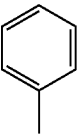 | —CH$_3$ |
| | 4.69 | 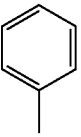 | 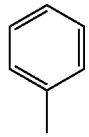 |
| | 4.70 | 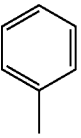 | 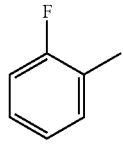 |

TABLE 4-continued

| Structure | # | R⁴ | R⁸ | R⁶ |
|---|---|---|---|---|
| (biphenyl-substituted structure) | 4.4 | —CH₃ | —CH₃ | H |
| (phenyl-substituted structure) | 4.5 | —CH₃ | —CH₃ | H |
| (2,5-dimethoxyphenyl-substituted structure) | 4.6 | —CH₃ | —CH₃ | H |
| (4-fluorophenyl-substituted structure) | 4.7 | —CH₃ | —CH₃ | H |
| (2-(phenylamino)phenyl-substituted structure) | 4.8 | —CH₃ | —CH₃ | H |
| (4-(diethylamino)phenyl-substituted structure) | 4.9 | —CH₃ | —CH₃ | H |
| (4-ethylphenyl-substituted structure) | 4.10 | —CH₃ | —CH₃ | H |

TABLE 4-continued
| Structure | # | | | |
|---|---|---|---|---|
| 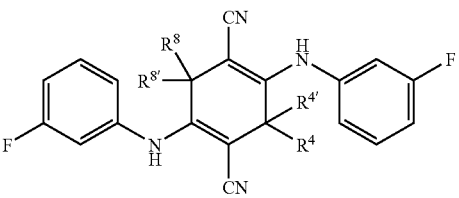 | 4.11 | —CH₃ | —CH₃ | H |
| 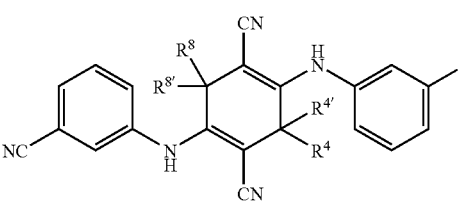 | 4.12 | —CH₃ | —CH₃ | H |
| 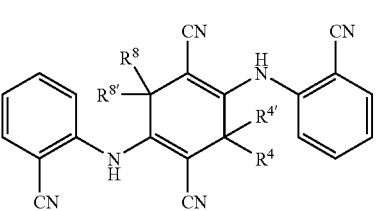 | 4.13 | —CH₃ | —CH₃ | H |
| 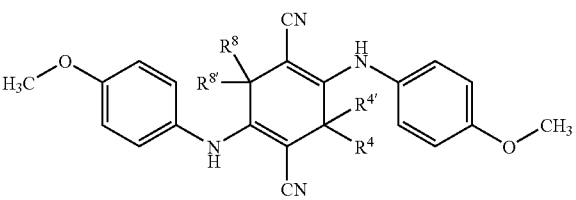 | 4.14 | —CH₃ | —CH₃ | H |
| 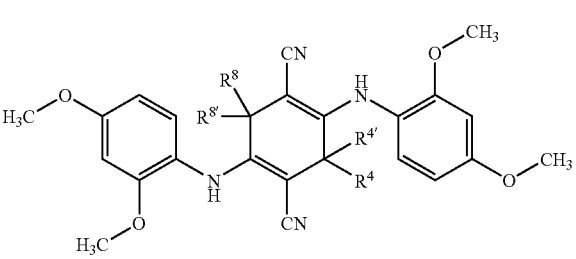 | 4.15 | —CH₃ | —CH₃ | H |
| 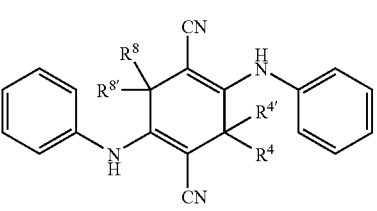 | 4.16 | —CH₃ | —CH₃ | H |
| 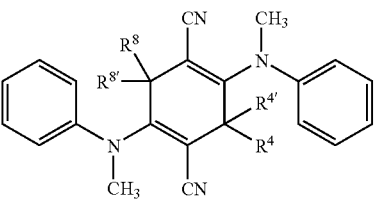 | 4.17 | —CH₃ | —CH₃ | —CH₃ |

TABLE 4-continued

| Structure | No. | | | |
|---|---|---|---|---|
| 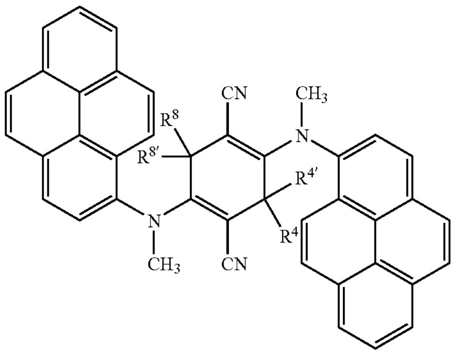 | 4.18 | —CH$_3$ | —CH$_3$ | H |
| 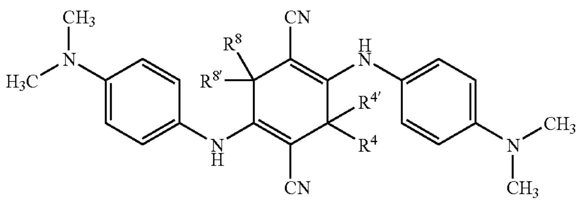 | 4.19 | —CH$_3$ | —CH$_3$ | H |
| 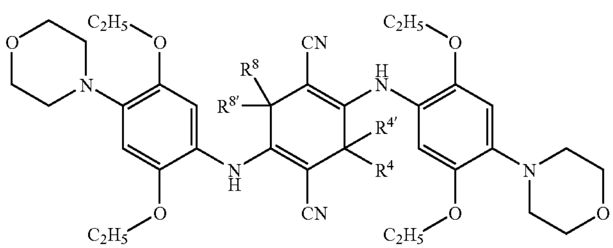 | 4.20 | —CH$_3$ | —CH$_3$ | H |
| 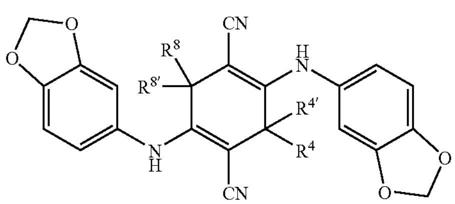 | 4.21 | —CH$_3$ | —CH$_3$ | H |
| 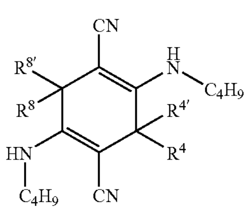 | 4.22 | —CH$_3$ | —CH$_3$ | H |
| 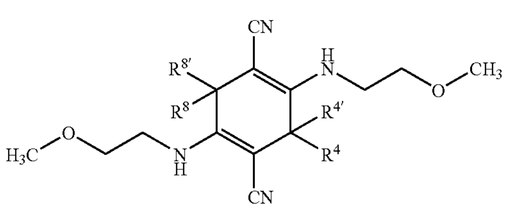 | 4.23 | —CH$_3$ | —CH$_3$ | H |

TABLE 4-continued

| Structure | # | | | |
|---|---|---|---|---|
| (4.24 structure) | 4.24 | —CH₃ | —CH₃ | H |
| (4.25 structure) | 4.25 | —CH₃ | —CH₃ | H |
| (4.26 structure) | 4.26 | —CH₃ | —CH₃ | —CH₃ |
| (4.27 structure) | 4.27 | —CH₃ | —CH₃ | H |
| (4.28 structure) | 4.28 | —CH₃ | —CH₃ | —CH₃ |
| (4.29 structure) | 4.29 | —CH₃ | —CH₃ | —CH₃ |
| (4.30 structure) | 4.30 | —CH₃ | —CH₃ | —CH₃ |

TABLE 4-continued
| | | | | |
|---|---|---|---|---|
| 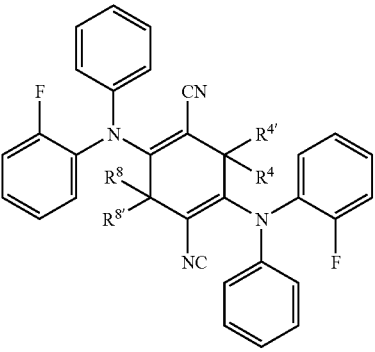 | 4.31 | —CH₃ | —CH₃ | 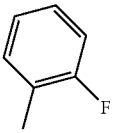 |
| 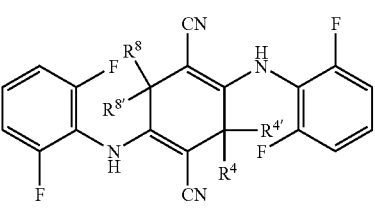 | | —CH₃ | —CH₃ | H |
| 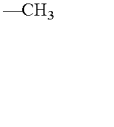 | 4.32 | —CH₃ | —CH₃ | —CH₃ |
| 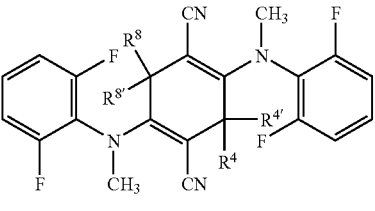 | 4.33 | —CH₃ | —CH₃ | H |
|  | 4.34 | —CH₃ | —CH₃ | 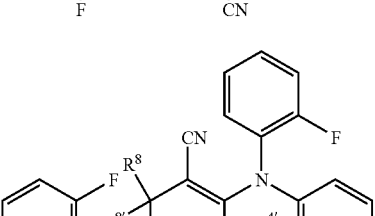 |
| 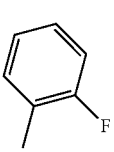 | 4.35 | —CH₃ | —CH₃ | 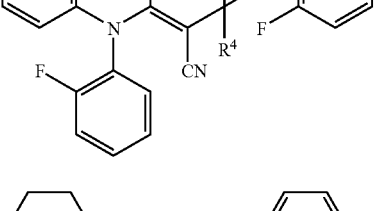 |

TABLE 4-continued

| | | | |
|---|---|---|---|
| 4.36 | —CH₃ | —CH₃ | (phenyl) |
| 4.37 | —CH₃ | —CH₃ | (phenyl) |
| 4.38 | —CH₃ | —CH₃ | (2-methoxyphenyl) |
| 4.39 | —CH₃ | —CH₃ | H |
| 4.40 | —CH₃ | —CH₃ | —CH₃ |
| 4.41 | —CH₃ | —CH₃ | —CH₃ |
| 4.42 | —CH₃ | —CH₃ | —CH₃ |
| 4.43 | —CH₃ | —CH₃ | —CH₃ |
| 4.44 | —CH₃ | —CH₃ | —CH₃ |
| 4.45 | —CH₃ | —CH₃ | —CH₃ |
| 4.46 | —CH₃ | —CH₃ | —CF₃ |
| 4.47 | —CH₃ | —CH₃ | —CF₃ |
| 4.48 | —CH₃ | —CH₃ | —CF₃ |
| 4.49 | —CH₃ | —CH₃ | —CF₃ |
| 4.50 | —CH₃ | —CH₃ | —CF₃ |
| 4.51 | —CH₃ | —CH₃ | —CF₃ |
| 4.52 | —CH₃ | —CH₃ | (phenyl) |

TABLE 4-continued
| | | | |
|---|---|---|---|
| 4.53 | —CH₃ | —CH₃ | 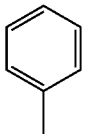 |
| 4.54 | —CH₃ | —CH₃ | 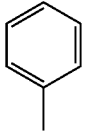 |
| 4.55 | —CH₃ | —CH₃ | 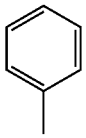 |
| 4.56 | —CH₃ | —CH₃ | 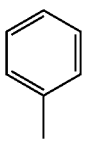 |
| 4.57 | —CH₃ | —CH₃ | 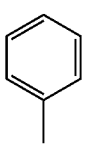 |
| 4.58 | —CH₃ | —CH₃ | 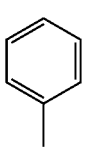 |
| 4.59 | —CH₃ | —CH₃ | 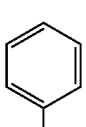 |
| 4.60 | —CH₃ | —CH₃ | 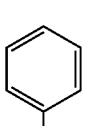 |
| 4.61 | —CH₃ | H | —CH₃ |
| 4.62 | —CH₃ | H | 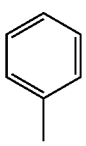 |
| 4.63 | —CH₃ | H | 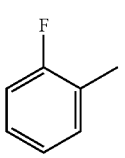 |

TABLE 4-continued

| | | | | |
|---|---|---|---|---|
| 4.64 | —CH₃ | H | 2-fluorophenyl | |
| 4.65 | —CH₃ | H | 2-fluorophenyl | |
| 4.66 | —CH₃ | H | H | |
| 4.67 | —CH₃ | H | phenyl | |
| 4.68 | phenyl | phenyl | —CH₃ | |
| 4.69 | phenyl | phenyl | phenyl | |
| 4.70 | phenyl | phenyl | phenyl | |

| Substance | | R⁷ | R⁴' | R⁸' |
|---|---|---|---|---|
| biphenyl-substituted diaminodicyanobenzene structure | 4.4 | 4-biphenyl | —CH₃ | —CH₃ |
| phenyl-substituted diaminodicyanobenzene structure | 4.5 | 2,4,5-trimethoxyphenyl | —CH₃ | —CH₃ |

TABLE 4-continued

| Structure | # | R | | |
|---|---|---|---|---|
| (2,5-dimethoxyphenyl-NH)₂ cyclohexadiene with CN, R⁸, R⁸', R⁴, R⁴' | 4.6 | 2,5-dimethoxy-methylphenyl | —CH₃ | —CH₃ |
| (4-fluorophenyl-NH)₂ cyclohexadiene with CN, R⁸, R⁸', R⁴, R⁴' | 4.7 | 4-fluorophenyl | —CH₃ | —CH₃ |
| bis(2-(phenylamino)phenyl-NH) cyclohexadiene with CN, R⁸, R⁸', R⁴, R⁴' | 4.8 | 2-(phenylamino)phenyl | —CH₃ | —CH₃ |
| bis(4-(diethylamino)phenyl-NH) cyclohexadiene with CN, R⁸, R⁸', R⁴, R⁴' | 4.9 | 4-(diethylamino)phenyl | —CH₃ | —CH₃ |
| bis(4-ethylphenyl-NH) cyclohexadiene with CN, R⁸, R⁸', R⁴, R⁴' | 4.10 | 4-ethylphenyl | —CH₃ | —CH₃ |
| bis(3-fluorophenyl-NH) cyclohexadiene with CN, R⁸, R⁸', R⁴, R⁴' | 4.11 | 3-fluorophenyl | —CH₃ | —CH₃ |
| bis(3-cyanophenyl-NH) cyclohexadiene with CN, R⁸, R⁸', R⁴, R⁴' | 4.12 | 3-cyanophenyl | —CH₃ | —CH₃ |

TABLE 4-continued
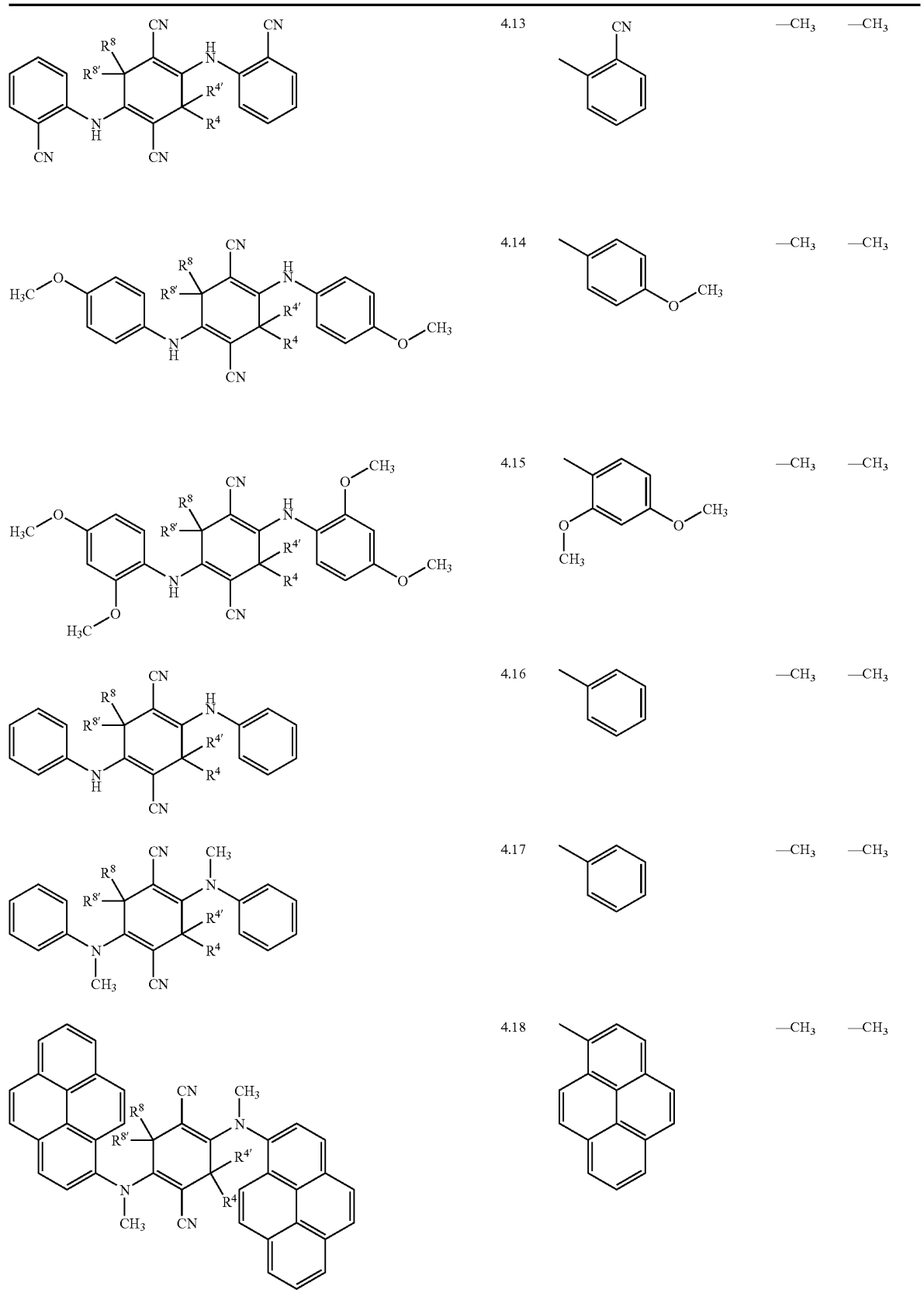

TABLE 4-continued

| | Structure (left) | # | R group | | |
|---|---|---|---|---|---|
| | | 4.19 | 4-(dimethylamino)phenyl | —CH₃ | —CH₃ |
| | | 4.20 | 2,5-diethoxy-4-morpholinophenyl | —CH₃ | —CH₃ |
| | | 4.21 | benzo[1,3]dioxol-5-yl | —CH₃ | —CH₃ |
| | | 4.22 | —C₄H₉ | —CH₃ | —CH₃ |
| | | 4.23 | —CH₂CH₂OCH₃ | —CH₃ | —CH₃ |
| | | 4.24 | 3,4,5-trimethoxyphenyl | —CH₃ | —CH₃ |
| | | 4.25 | 2,4,6-trimethylphenyl (mesityl) | —CH₃ | —CH₃ |

TABLE 4-continued
| Structure | # | R group 1 | R group 2 | R group 3 |
|---|---|---|---|---|
| 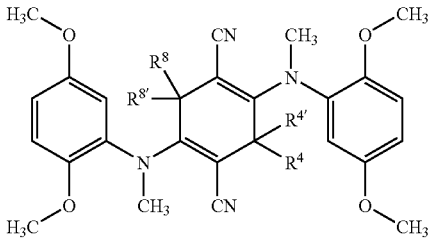 | 4.26 | 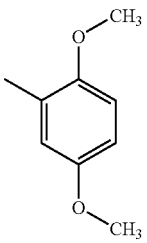 | —CH₃ | —CH₃ |
| 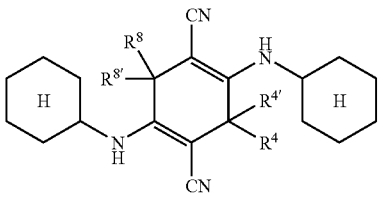 | 4.27 | 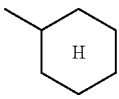 | —CH₃ | —CH₃ |
| 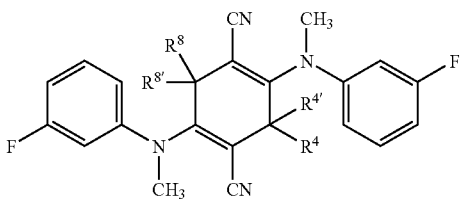 | 4.28 | 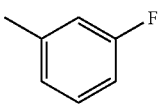 | —CH₃ | —CH₃ |
| 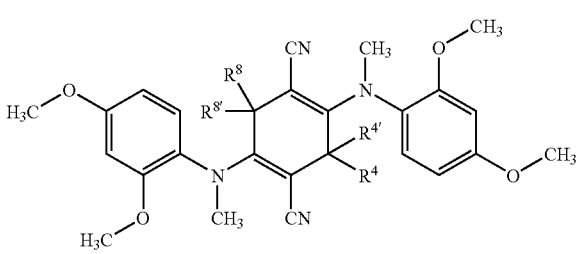 | 4.29 | 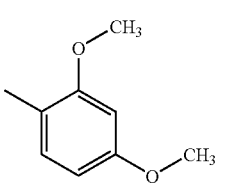 | —CH₃ | —CH₃ |
| 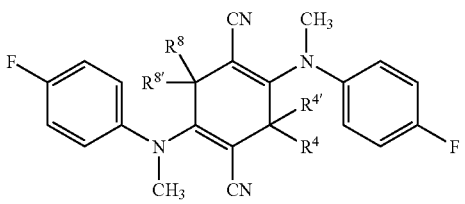 | 4.30 | 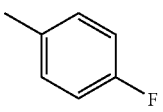 | —CH₃ | —CH₃ |
| 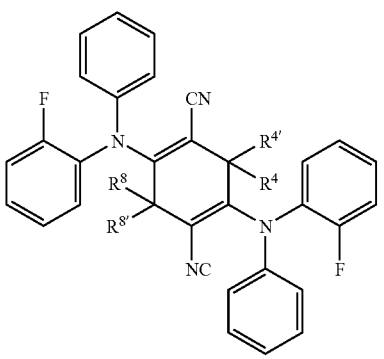 | 4.31 | 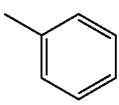 | —CH₃ | —CH₃ |

TABLE 4-continued

| Structure | # | Ar | R | R' |
|---|---|---|---|---|
| (structure) | | 2,6-difluorophenyl | —CH₃ | —CH₃ |
| (structure) | 4.32 | 2,6-difluorophenyl | —CH₃ | —CH₃ |
| (structure) | 4.33 | 2,6-difluorophenyl | —CH₃ | —CH₃ |
| (structure) | 4.34 | 2-fluorophenyl | —CH₃ | —CH₃ |
| (structure) | 4.35 | cyclohexyl | —CH₃ | —CH₃ |
| (structure) | 4.36 | 2-naphthyl | —CH₃ | —CH₃ |

TABLE 4-continued

| Structure | # | Group | R | R' |
|---|---|---|---|---|
| (naphthyl/phenyl diamine dicyano cyclohexene structure with R⁸, R⁸', R⁴, R⁴') | 4.37 | 1-methylnaphthyl | —CH₃ | —CH₃ |
| (methoxyphenyl triamine dicyano structure with R⁸, R⁸', R⁴, R⁴') | 4.38 | 2-methoxy-methylphenyl | —CH₃ | —CH₃ |
| (indolyl diamine dicyano structure with R⁸, R⁸', R⁴, R⁴') | 4.39 | 5-methyl-1H-indolyl | —CH₃ | —CH₃ |
| | 4.40 | 3-methylpyridyl | —CH₃ | 1'CH₃ |
| | 4.41 | 4-trifluoromethyl-2-methyl-pyrrolidinylphenyl | —CH₃ | —CH₃ |
| | 4.42 | 3-methylpyridyl | —CH₃ | —CH₃ |
| | 4.43 | 1-methylnaphthyl | —CH₃ | —CH₃ |

TABLE 4-continued

| | | | | |
|---|---|---|---|---|
| 4.44 | 2-methylnaphthalene | —CH₃ | —CH₃ |
| 4.45 | 2-fluoro-6-methylphenyl | —CH₃ | —CH₃ |
| 4.46 | phenyl | —CH₃ | —CH₃ |
| 4.47 | 1-methylnaphthalene | —CH₃ | —CH₃ |
| 4.48 | 2-methylnaphthalene | —CH₃ | —CH₃ |
| 4.49 | 2-fluorophenyl | —CH₃ | —CH₃ |
| 4.50 | 2,3,4,5-tetrafluoro-6-methylphenyl | —CH₃ | —CH₃ |
| 4.51 | 2-pyrimidinyl | —CH₃ | —CH₃ |
| 4.52 | 2-fluorophenyl | —CH₃ | —CH₃ |

TABLE 4-continued

| | | | | |
|---|---|---|---|---|
| 4.53 | 2-fluorophenyl | —CH₃ | —CH₃ |
| 4.54 | 3-fluorophenyl | —CH₃ | —CH₃ |
| 4.55 | 2,4-dimethoxyphenyl | —CH₃ | —CH₃ |
| 4.56 | 4-cyanophenyl | —CH₃ | —CH₃ |
| 4.57 | benzo[1,3]dioxol-5-yl | —CH₃ | —CH₃ |
| 4.58 | naphthalen-1-yl | —CH₃ | —CH₃ |
| 4.59 | naphthalen-2-yl | —CH₃ | —CH₃ |
| 4.60 | 2,3,4-trifluorophenyl | —CH₃ | —CH₃ |

TABLE 4-continued

| | | | | |
|---|---|---|---|---|
| 4.61 | pentafluorophenyl | —CH₃ | —CH₃ | |
| 4.62 | pentafluorophenyl | —CH₃ | —CH₃ | |
| 4.63 | julolidinyl | —CH₃ | —CH₃ | |
| 4.64 | 2-(trifluoromethoxy)phenyl | —CH₃ | —CH₃ | |
| 4.65 | 2-fluorophenyl | —CH₃ | —CH₃ | |
| 4.66 | phenyl | —CH₃ | —CH₃ | |
| 4.67 | phenyl | —CH₃ | —CH₃ | |
| 4.68 | phenyl | —CH₃ | —CH₃ | |
| 4.69 | phenyl | —CH₃ | —CH₃ | |

TABLE 4-continued
| | | | | | | | | |
|---|---|---|---|---|---|---|---|---|
| | | 4.70 | 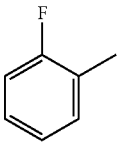 | | | —CH₃ | —CH₃ | |
| Substance | R² | R³ | R⁴ | R⁶ | R⁷ | R⁸ | R⁸' | R⁴' |
|---|---|---|---|---|---|---|---|---|
| 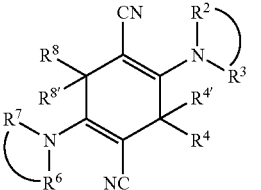 | 56.0 | | | | | | | |
| 56.1 | 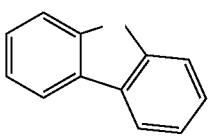 | —CH₃ | | 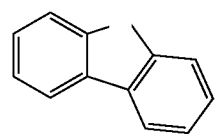 | | —CH₃ | —CH₃ | —CH₃ |
| 56.2 | 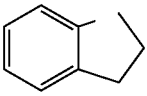 | —CH₃ | | 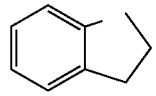 | | —CH₃ | —CH₃ | —CH₃ |
| 56.3 | 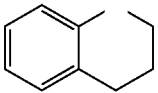 | —CH₃ | | 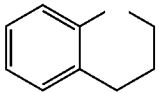 | | —CH₃ | —CH₃ | —CH₃ |
| 56.4 | 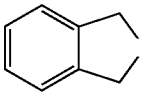 | —CH₃ | | 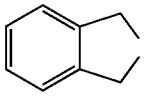 | | —CH₃ | —CH₃ | —CH₃ |
| Substance | R² | R³ | R⁶ | R⁷ | R⁸ | R⁸' | R⁴ | R⁴' |
|---|---|---|---|---|---|---|---|---|
| 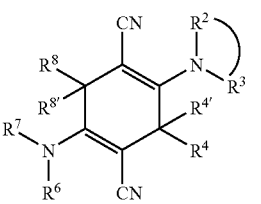 | 50.0 | | | | | | | |
| 50.1 | 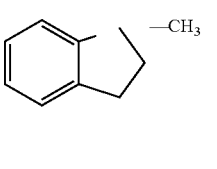 | —CH₃ | | 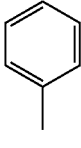 | —CH₃ | —CH₃ | —CH₃ | —CH₃ |
| 50.2 | 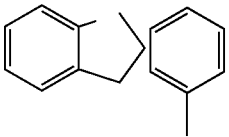 | | 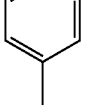 | —CH₃ | —CH₃ | —CH₃ | —CH₃ | |
| 50.3 | 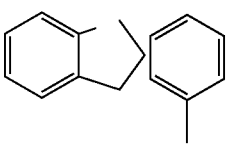 | | 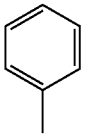 | 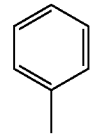 | | —CH₃ | 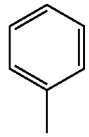 | —CH₃ |

TABLE 4-continued

| SUBSTANCE | | R⁸ | R⁸' | R³ | R⁶ | R⁷ | R⁴ | R⁴' | R² |
|---|---|---|---|---|---|---|---|---|---|
| *[structure 53.0]* | 53.0 | | | | | | | | |
| | 53.1 | —CH₃ | —CH₃ | phenyl | 2-ethylphenyl | | —CH₃ | —CH₃ | —CH₃ |
| | 53.2 | —CH₃ | —CH₃ | phenyl | 2-ethylphenyl | | —CH₃ | —CH₃ | phenyl |

| Substance | | R⁴' | R³ | R² | R⁸' | R⁷ | R⁶ | R⁴ | R⁸ |
|---|---|---|---|---|---|---|---|---|---|
| *[structure 57.0]* | 57.0 | | | | | | | | |
| | 57.1 | 2-ethylphenyl | 2-fluorophenyl | | 2-ethylphenyl | 2-fluorophenyl | | —CH₃ | —CH₃ |
| *[structure 51.0]* | 51.0 | | | | | | | | |
| | 51.1 | 2-ethylphenyl | 2-fluorophenyl | H | 2-fluorophenyl | phenyl | | —CH₃ | —CH₃ |

| Substance | | R⁴ | R⁴' | R³ | R² | R⁶ | R⁷ | R⁸' | R⁸ |
|---|---|---|---|---|---|---|---|---|---|
| *[structure 54.0]* | 54.0 | | | | | | | | |

TABLE 4-continued
| | | | | | | | |
|---|---|---|---|---|---|---|---|
| 54.1 | —CH$_3$ | —CH$_3$ | 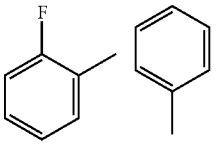 | 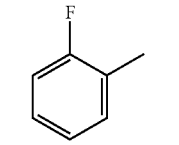 | 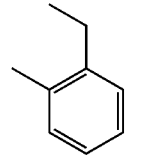 |  | —CH$_3$ |
| 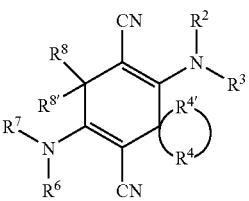 | 52.0 | | | | | | |
| 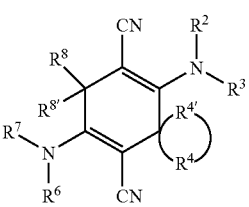 | 52.1 | 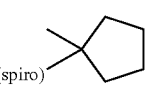 (spiro) | 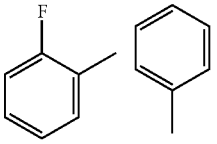 | 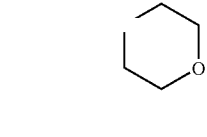 | 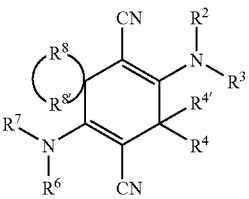 | —CH$_3$ | —CH$_3$ |
| 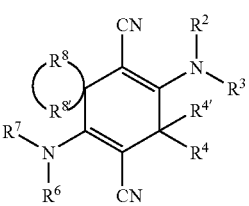 | 55.0 | | | | | | |
| 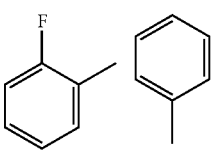 | 55.1 | —CH$_3$ | —CH$_3$ | 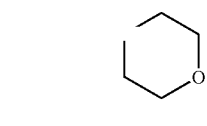 | 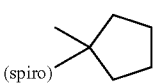 | 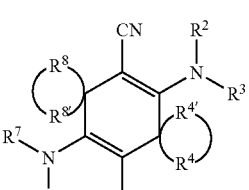 | 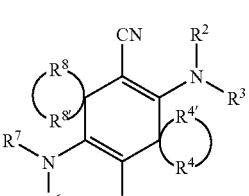 (spiro) |
|  | 58.0 | | | | | | |
| 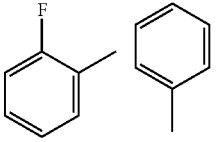 | 58.1 | 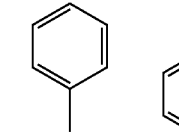 (spiro) | 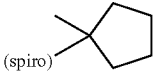 | | | | (spiro) |

What is claimed is:

1. An organic electroluminescent device comprising at least one emitter layer which includes at least one 2,5-diaminoterephthalic acid derivative having formula 20a:

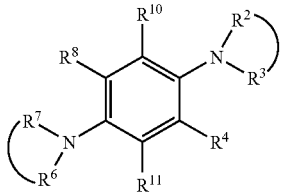

wherein $R^{10}$ is —CN or —C(=$X^1$)—$X^2R^1$;
$R^{11}$ is —CN or —C(=$X^3$)—$X^4R^5$;
$X^1$ and $X^3$, which are the same or different, are oxygen, sulphur or imino;
$X^2$ and $X^4$, which are the same or different, are oxygen, sulphur or substituted or unsubstituted amino;
$R^1$, $R^4$, $R^5$ and $R^8$ are the same or different and are hydrogen, C1–C20 alkyl, aryl, heteroaryl, wherein aryl and heteroaryl can be substituted singly or multiply with the same or different radicals di-C1–C3-amino, C1–C10 alkoxy, C1–C4 alkyl, cyano, fluorine, chlorine and bromine as well as phenyl;
$R^4$ and $R^8$ can also be halogen, nitro, cyano or amino and trifluoromethyl;
$R^2$ and $R^3$ are members of a 5- or 6-membered ring, forming a saturated or unsaturated heterocycle;
$R^6$ and $R^7$ are members of a 5- or 6-membered ring, forming a saturated or unsaturated heterocycle; and
wherein the following radicals can form a saturated or unsaturated ring $X^1$ and $X^2$, $R^4$ and $X^3$, $X^3$ and $X^4$, $R^5$ and $X^4$, $R^8$ and $X^1$, to which further rings can be fused.

2. The device of claim 1, wherein $X^1$ is oxygen when $R^{10}$ is —C(=$X^1$)—$X^2R^1$ and $X^3$ is oxygen when $R^{11}$ is —C(=$X^3$)—$X^4R^5$.

3. The device of claim 1, wherein $R^{10}$ and $R^{11}$ are —CN.

4. The device of claim 1, wherein
$R^{10}$ is —C(=$X^1$)—$X^2R^1$;
$R^{11}$ is —C(=$X^3$)—$X^4R^5$;
$X^2$ and $X^4$ are the same or different atoms or groups and are, oxygen, sulphur or substituted amino;
$R^1$ and $R^5$ are the same or different and are hydrogen, C1–C20 alkyl; aryl, substituted aryl, heteroaryl, or substituted heteroaryl; and
$R^4$ and $R^8$ are the same or different and are hydrogen, C1–C20 alkyl, halogen, nitro, cyano, amino, aryl, substituted aryl, heteroaryl, or substituted heteroaryl.

5. The device of claim 1, wherein $R^2$ and $R^3$ are members of a 5- or 6-membered ring, forming a saturated heterocycle; and
$R^6$ and $R^7$ are members of a 5- or 6-membered ring, forming a saturated heterocycle.

6. The organic electroluminescent device of claim 1, wherein $R^4$ and $R^8$ are the same or different and are 2-fluorophenyl, 3-fluorophenyl, 4-fluorophenyl, 2,4-difluorophenyl, 2,6-difluorophenyl, 2,3,4,5-tetrafluorophenyl or pentafluorophenyl.

7. An organic electroluminescent device comprising at least one emitter layer which includes at least one 2,5-diaminoterephthalic acid derivative having formula 1a:

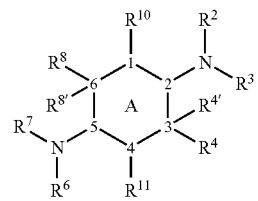

wherein the ring A is a benzene ring wherein $R^{4'}$ and $R^{8'}$ are omitted;
$R^{10}$ is —C(=$X^1$)—$X^2R^1$;
$R^{11}$ is —C(=$X^3$)—$X^4R^5$;
$X^1$, $X^2$, $X^3$ and $X^4$ are oxygen;
$R^1$ and $R^5$, are the same or different and are C1–C20 alkyl;
$R^2$ and $R^6$ are the same or different and are hydrogen, C1–C20 alkyl, trifluoro-methyl, aryl, or heteroaryl, wherein aryl and heteroaryl can be substituted singly or multiply with the same or different radicals, C1–C10 alkoxy, C1–C4 alkyl, cyano, fluorine, chlorine, bromine or phenyl;
$R^4$ and $R^8$ are the same or different and are hydrogen, C1–C20 alkyl, trifluoro-methyl, or phenyl; and
$R^3$ and $R^7$ are the same or different and are 2-fluorophenyl, 3-fluorophenyl, 4-fluorophenyl, 2,4-difluorophenyl, 2,6-difluoro-phenyl, 2,3,4,5-tetrafluorophenyl or pentafluorophenyl.

8. The device of claim 7 wherein $R^1$ and $R^5$ are the same or different and are C1–C4 alkyl.

9. The device of claim 7 wherein $R^4$ and $R^8$ are hydrogen.

10. The device of claim 7 wherein $R^1$ and $R^5$ are the same or different and are C1–C4 alkyl;
$R^4$ and $R^8$ are hydrogen; and
$R^2$ and $R^6$ are the same or different and are hydrogen or methyl.

11. An organic electroluminescent device comprising at least one emitter layer which includes at least one 2,5-diaminoterephthalic acid derivative having formula 1a:

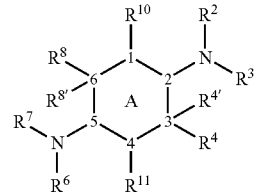

wherein the ring A is a benzene ring wherein $R^{4'}$ and $R^{8'}$ are omitted;
$R^{10}$ is —C(=$X^1$)—$X^2R^1$;
$R^{11}$ is —C(=$X^3$)—$X^4R^5$;
$X^1$, $X^2$, $X^3$ and $X^4$ are oxygen;
$R^1$ and $R^5$, are the same or different and are C1–C20 alkyl;
$R^2$ and $R^6$ are the same or different and are hydrogen, C1–C20 alkyl, trifluoro-methyl, aryl, or heteroaryl, wherein aryl and heteroaryl can be substituted singly or multiply with the same or different radicals, C1–C10 alkoxy, C1–C4 alkyl, cyano, fluorine, chlorine, bromine or phenyl;
$R^4$ and $R^8$ are the same or different and are hydrogen, C1–C20 alkyl, trifluoro-methyl, or phenyl; and
$R^3$ and $R^7$ are the same or different and are C1–C20 alkyl.

12. The device of claim 11 wherein $R^1$ and $R^5$ are the same or different and are C1–C4 alkyl.

13. The device of claim 11 wherein $R^4$ and $R^8$ are hydrogen.

14. The device of claim 11 wherein $R^1$ and $R^5$ are the same or different and are C1–C4 alkyl;
$R^4$ and $R^8$ are hydrogen; and
$R^2$ and $R^6$ are the same or different and are hydrogen or methyl.

15. The device of claim 11 wherein $R^3$ and $R^7$ are each cyclohexyl.

16. An organic electroluminescent device comprising at least one emitter layer which includes at least one 2,5-diaminoterephthalic acid derivative having formula 1a:

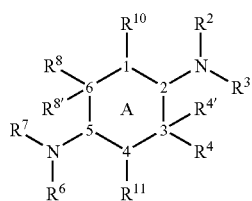

1a wherein the ring A is a benzene ring wherein $R^{4'}$ and $R^{8'}$ are omitted;
$R^{10}$ is —C(=$X^1$)—$X^2R^1$;
$R^{11}$ is —C(=$X^3$)—$X^4R^5$;
$X^1$, $X^2$, $X^3$ and $X^4$ are oxygen;
$R^2$ and $R^6$ are the same or different and are hydrogen, C1–C20 alkyl, trifluoro-methyl, aryl, or heteroaryl, wherein aryl and heteroaryl can be substituted singly or multiply with the same or different radicals, C1–C10 alkoxy, C1–C4 alkyl, cyano, fluorine, chlorine, bromine or phenyl;

$R^4$ and $R^8$ are hydrogen;
$R^1$ and $R^5$ are the same or different and are C1–C4 alkyl; and
$R^3$ and $R^7$ are the same or different and are C1–C20 alkyl.

17. The device of claim 16 wherein $R^3$ and $R^7$ are each cyclohexyl.

18. An organic electroluminescent device comprising at least one emitter layer which includes at least one 2,5-diaminoterephthalic acid derivative having formula 1a:

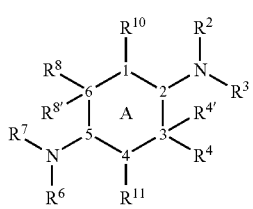

1a wherein the ring A is a benzene ring wherein $R^{4'}$ and $R^{8'}$ are omitted;
$R^{10}$ is —C(=$X^1$)—$X^2R^1$;
$R^{11}$ is —C(=$X^3$)—$X^4R^5$;
$X^1$, $X^2$, $X^3$ and $X^4$ are oxygen;
$R^1$ and $R^5$ are methyl;
$R^4$ and $R^8$ are hydrogen;
$R^2$ and $R^6$ are hydrogen; and
$R^3$ and $R^7$ are cyclohexyl.

* * * * *